US006348573B1

(12) United States Patent
Nunez et al.

(10) Patent No.: US 6,348,573 B1
(45) Date of Patent: Feb. 19, 2002

(54) COMPOSITIONS AND METHODS FOR IDENTIFYING APOPTOSIS SIGNALING PATHWAY INHIBITORS AND ACTIVATORS

(75) Inventors: Gabriel Nunez; Naohiro Inohara; Takeyoshi Koseki, all of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/069,023

(22) Filed: Apr. 27, 1998

(51) Int. Cl.[7] .................. C07K 17/00; G01N 33/53; G01N 33/567; A61K 38/00
(52) U.S. Cl. ............... 530/350; 530/324; 530/399; 435/7.1; 435/7.21; 435/7.2; 514/2
(58) Field of Search .................. 530/324, 399, 530/350; 435/7.1, 7.21, 7.2; 514/2

(56) References Cited

U.S. PATENT DOCUMENTS

| 4,366,241 A | 12/1982 | Tom et al. ................ 435/7 |
| 4,435,504 A | 3/1984 | Zuk et al. ................ 435/7 |
| 4,683,195 A | 7/1987 | Mullis et al. ............. 435/6 |
| 4,683,202 A | 7/1987 | Mullis .................... 435/91 |
| 5,652,096 A | 7/1997 | Cimino ................... 435/6 |

FOREIGN PATENT DOCUMENTS

| WO | WO 93/03176 | 2/1993 | ............ C12Q/1/00 |

OTHER PUBLICATIONS

Rudin and Thompson, "Apoptosis and Disease: Regulation and Clinical Relevance of Programmed Cell Death," *Ann. Rev. Med.* 48:267–81 (1997).
Cohen et al., "Glucocorticoid Activation of a Calcium–Dependent Endonuclease in Thymocyte Nuclei Leads to Cell Death," *J. Immunol.* 132:38–42 (1984).
Marmur and Lane, "Strand Separation and Specific Recombination in Deoxyribonucleic Acids: Biological Studies," *Proc. Natl. Acad. Sci. USA* 46:453–461 (1960).
Doty et al., "Strand Separation and Specific Recombination in Deoxyribonucleic Acids: Physical Chemical Studies," *Proc. Natl. Acad. Sci. USA* 46:461–476 (1960).
Wallace et al., "Application of Synthetic Oligonucleotides to the Diagnosis of Human Genetic Diseases" *Biochimie* 67:755–762 (1985).
Studencki and Wallace, "Allele–Specific Hybridization Using Oligonucleotide Probes of Very High Specific Activity: Discriminaation of the Human $\beta^A$– and $\beta^A$–Globin Genes," *DNA* 7–14 (1984).
Studencki et al., "Discrimination Among the Human $\beta^A$, $\beta^S$, and $\beta^C$–Globin Genes Using Allele–Specific Oligonucleotide Hybridization Probes," *Human Genetics* 37:42–51 (1985).
Smith and Waterman, "Comparison of Biosequences," *Adv. Appl. Math.* 2: 482–489 (1981).

Needleman and Wunsch, "A General Method Applicable too the Search for Similarities in the Amino Acid Sequence of Two Proteins," *J. Mol. Biol.* 48:443–453 (1970).
Pearson and Lipman, "Improved Tools for Biological Sequence Comparison," *Proc. Natl. Acad. Sci. (U.S.A.)* 85:2444–2448 (1988).
Kidd, V., "Proteolytic Activities That Mediate Apoptosis," *Ann. Rev. Physiol.* 60:533–573 (1998).
Boldin et al., "Involvement of MACH, a Novel MORT1/FADD–Interacting Protease, in Fas/APO–1 and TNF Receptor–Induced Cell Death," *Cell* 85:803–815 (1996).
Wu et al., "Interaction and Regulation of the *Caenorhabditis elegans* Death Protease CED–3 and CED–9," *J. Biol. Chem.* 272:21449–21454 (1997).
Zou et al., "Apaf–1, a Human Protein Homologous to *C. elegans* CED–4, Participants in Cytochrome c–Dependent Activation of Caspase–3," *Cell* 90:405–413 (1997).
Zhou et al., "Targeting Protease Specificity of the Viral Serpin CrmA," *J. Biol. Chem.* 272:7797–7800 (1997).
Duckett et al., "A Conserved Family of Cellular Genes Related to the Baculovirus iap Gene and Encoding Apoptosis Inhibitors," *EMBO J.* 15:2695–2694 (1996).
Devereaux et al., "X–linked IAP is a Direct Inhibitor of Cell–Death Proteases," *Nature* 388:300–304 (1997).
Chinnaiyan et al., "FADD, a Novel Death Domain–Containing Protein, Interacts with the Death Domain of Fas And Initiates Apoptosis," *Cell* 81:505–512 (1995).
Hsu et al., "The TNF receptor 1–Associated Protein TRADD Signals Cell Death and NF–kB Activation," *Cell* 19:495–504 (1995).
Chinnaiyan et al., "FADD/MORT1 Is a Common Mediator of CD95 (Fas/APO–1) and Tumor Necrosis Factor Receptor–Induced Apoptosis," *J. Biol. Chem.* 271:4961–4965 (1996).
Bump et al., "Inhibition of ICE Family Proteases by Baculovirus Antiapoptic Protein p35," *Science* 269:1885–1888 (1995.
Irmler et al., "Inhibition of Death Receptor Signals by Cellular FLIP," *Nature* 388:190–195 (1997).
Duan, H. and Dixit V. M., "RAIDD Is a New 'Death' Adaptor Molecule," *Nature* 385:86–89 (1977).
Matsuda et al., "Visualization of Dystrophic Muscle Fibers in Mdx Mouse by Vital Staining with Evans Blue: Evidence of Apoptosis in Dystrophin–Deficient Muscle," *J. Biochem.* 118:959–964 (1995).
Teiger et al., "Apoptosis in Pressure Overload–Induced Heart Hypertrophy in the Rat," *J. Clin. Invest.* 97:2891–2897 (1996).
Nicholson et al., "Identification and inhibition of the ICE/CED–3 protease necessary for mammalian apoptosis," *Nature* 376:37–43 (1995).

(List continued on next page.)

*Primary Examiner*—Yvonne Eyler
*Assistant Examiner*—Janet Andres
(74) *Attorney, Agent, or Firm*—Medlen & Carroll, LLP

(57) ABSTRACT

The invention generally relates to compositions and methods for identifying Apoptosis signaling pathway inhibitors and activators.

5 Claims, 44 Drawing Sheets

OTHER PUBLICATIONS

Wang et al., "Purification of an Interleukin–1β Converting Enzyme–related Cysteine Protease That Cleaves Sterol Regulatory Element–binding Proteins between the Leucine Zipper and Transmembrane Domains," *J. Biol. Chem.* 270(30):18044–18050 (1995).

Casciola–Rosen et al., "Specific Cleavage of the 70–kDA Protein Component of th U1 Small Nuclear Ribonucleoprotein Is a Characteristic Biochemical Feature of Apoptotic Cell Death," *J. Biol. Chem.* 269:30757–30760 (1994).

Song et al., "DNA–dependant protein kinase catalytic subunit: a target for an ICE–like protease in apoptosis," *EMBO J.* 15:3238–3246 (1996).

An, B. and Dou Q. P., "Cleavage of Retinoblastoma Protein during Apoptosis: An Interleukin 1β–converting Enzyme–like Protease as Candidate," *Cancer Res.* 56:438–442 (1996).

Danesch et al., "Cloning and Transcriptional Regulation of a Novel Adipocyte–specific Gene FSP27," *J. Biol. Chem.* 267:7185–7193 (1992).

Williams et al., "CCAAT/Enhancer binding Protein Expression is rapidly Extinguished in TA1 Adipocyte cells Treated with Tumor Necrosis Factor," *Mol. Endocrinol.* 6:1135–1141 (1992).

Enari et al., "A caspase–activated DNase that degrades DNA during apoptosis, and its inhibitor ICAD," *Nature* 391:43–50 (1998).

Sakahira et al., "Cleavage of CAD inhibitor in CAD activation and DNA degradation during apoptosis," *Nature* 391:96–99 (1998).

Trauth et al., "Monoclonal Antibody–Mediated Tumor Regression by Induction of Apoptosis," *Science* 245:301–305 (1989).

Yonehara et al., "A Cell–Killing Monoclonal Antibody (ANTI–Fas) To a Cell Surface Antigen Co–Downregulated With The Receptor Of Tumor Necrosis Factor," *J. Exp. Med.* 169:1747–1756 (1989).

Watanabe–Fukanaga et al., "The cDNA Structure, Expression, and Chromosomal Assignment of the Mouse Fas Antigen," *J. Immunol.* 148:1274–1279 (1992).

Oehm et al., Purification and Molecular Cloning of the APO–1 cell Surface Antigen, a Member of the Tumor Necrosis Factor/Nerve Growth Factor Receptor Superfamily, *J. Biol.Chem.* 267:10709–10715 (1992).

Smith et al., "The TNF Receptor Superfamily of Cellular and Viral Proteins: Activation, Constimulation, and Death," *Cell* 76:959–962 (1994).

Tartaglia et al., "The Two Different Receptors for Tumor Necrosis factor Mediate Distinct cellular responses," *Proc. Natl. Acad. Sci.* 88:9292–9296 (1991).

Tartaglia et al., "Tumor Necrosis Factor's Cytotoxic Activity is Signaled by the p55 TNF Receptor," *Cell* 73:213–216 (1993b).

Heller et al., "The p70 Tumor Necrosis Factor Receptor mediates Cytotoxicity," *Cell* 70:47–56 (1992).

Heller et al., "Cytotoxity by Tumor Necrosis Factor is Mediated by both p55 and p70 Receptors," *Cell* 73:216 (1993).

Clement and Stamenkovic, "Fas and Tumor Necrosis Factor Receptor–mediated Cell Death: Similarities and Distinctions," *J. Exp. Med.* 180:557–567 (1994).

Nagata, S., "Apoptosis by Death Factor," *Cell* 88:355–365 (1997).

Boldin et al., "A Novel Protein That Interacts with the Death Domain of Fas/APO1 Contains a Sequence Motif Related to the Death Domain," *J. Biol. Chem.* 270:7795–7798 (1995).

Muzio et al., "FLICE, A Novel FADD–Homologous ICE/CED–3–like Protease, Is Recruited to the CD95 (Fas/APO–1) Death–Inducing Signaling Complex," *Cell* 85:817–827 (1996).

Medema et al., "FLICE is activated by association with the CD95 death–inducing signaling complex (DISC)," *EMBO J.* 16:2794–2804 (1997).

Stanger et al., "RIP: A Novel Protein Containing a Death Domain That Interacts with Fas/APO–1 (CD95) in Yeast and Causes Cell Death," *Cell* 81:513–523 (1995).

Ting et al., "RIP mediates tumor necrosis factor receptor 1 activation of NF–kB but not Fas/APO–1–initiated apoptosis," *EMBO J.* 15:6189–6196 (1996).

Wurm et al., "Incudible overproduction of the mouse c–myc protein in mammalian cells," *Proc. Natl. Acad. Sci. U.S.A.* 83:5414–5418 (1986).

Wallach, "Preparations of Lymphotoxin Induce Resistance to Their Own Cytotoxic Effect," *J. Immunol.* 132:2464–2469 (1984).

Makarov et al., "Hyperinducible human metallothionen promoter with a low level basal activity," *Nucleic Acids Res.* 22:1504–1505 (1994).

Gossen et al., "Tight control of gene expression in mammalian cells by tetracycline–responsive promoters," *Proc. Natl. Acad. Sci. U.S.A.* 89:5547–5551 (1992).

Christopherson et al., "Ecdysteroid–dependent regulation of genes in mammalian cells by a Drosophila ecdoysone receptor and chimeric transactivators," *Proc. Natl. Acad. Sci. U.S.A.* 89:6314–6318 (1992).

Wang et al., "A regulatory system for use in gene transfer," *Proc. Natl. Acad. Sci. U.S.A.* 91:8180–8184 (1994).

Dafforn et al., "Rapid, Simple and reliable Doctor's Office Test for Antibodies to Human Immunodeficiency Virus 1 in Serum," *Clin. Chem.* 36:1312–1316 (1990).

Li et al., "One–step Enzyme Immunochromatographic Assay for Theophylline," *Anal. Biochem.* 166:276–283 (1987).

Zuk et al., "Enzyme Immunochromatography—A Quantitative Immunoassay Requiring No Instrumentation" *Clin. Chem.* 31:1144 1150(1985).

Inohara, "harakiri, a novel regulator of cell death, encodes a protein that activates apoptosis and interacts selectively with survival–promoting proteins Bcl–2 and Bcl–$X_L$," *EMBO J.* 16:1686–1694 (1997).

Oltvai et al., "Bcl–2 Heterodimerizes In Vivo with a Conserved Homolog, Bax, That Accelerates Programmed Cell Death," *Cell* 74:609–619 (1993).

Miura et al., "Induction of Apoptosis in Fibroblasts by IL–1β–Converting Enzyme, a mammalian Homolog of the *C. elegans* Cell Death gene ced–3," *Cell* 75:653–660 (1993).

Inohara et al., "CLARP, a death effector domain–containing protein interacts with caspase–8 and regulates apoptosis," *Proc. Natl. Acad. Sci. USA* 94:10717–10722 (1997).

Merino et al., "Modulation of Anti–IgM–Induced B Cell Apoptosis by Bcl–$x_L$ and CD40 in WEHI–231 Cells," *J. Immunol.* 155:3830–3838 (1995).

del Peso et al., "Interleukin–3–Induced Phosphorylation of BAD Through the Protein Kinase Akt," *Science* 278:687–689 (1997).

Numa et al., "Elevated Levels of Syndecan–1 Expression Confer Potent Serum–dependant Growth in Human 293T Cells," *Cancer Res.* 55:4676–4680 (1995).

Geertman et al., "Cloning and Characterization of cDNAs for Novel proteins with Glutamic Acid–Proline Dipeptide Tandem Repeats," *Biochem. Biophys. Acta* 1306:147–152 (1996).

Chinnaiyan et al., "Signal Transduction by DR3, a Death Domain–containing Receptor Related to TNFR–1 and CD95" *Science* 274:990–992 (1996).

Kischkel, F. C. et al., "Cytoxicity0dependent APO–1 (Fas/CD95)–associated proteins form a death–inducing signaling complex (DISC) with the receptor" *EMBO J.* 14:5579–5588 (1995).

Hofmann, K. et al., "The CARD domain: a new apoptic singaling motif" *Trends. Biochem. Sci.* 22:155–156 (1997).

Fernandes–Alnemri, T. et al., "In Vitro Activation of CPP32 and Mch3 by Mch4, a novel Human Apoptic Cystein protease Containing Two FADD–like Domains" *Proc. Natl. Acad. Sci. USA* 93:7464–7469 (1996).

Goltsev, Y. V. et al., "CASH, a Novel Caspase Homologue with Death Effector Domains" *J. Biol. Chem.* 272:19641–19644 (1997).

Hu, S.et al., "I–FLICE, a Novel Inhibitor of Tumor Necrosis Factor Receptor–1–and CD–95–induced Apoptosis" *J. Biol. Chem.* 272:17255–17257 (1997).

Shu, H. B. et al., "Casper Is a FADD– and Caspase–Related Inducer of Apotosis" *Immunity* 6:751–763 (1997).

Srinivasula, S. M. et al., "FLAME–1, a Novel FADD–like Anti–apoptic molecule That Regulates Fas/TNFR1–induced Apoptosis" *J. Biol. Chem.* 272:18542–18545 (1997).

Han, D. K. M. et al., "MRIT, a novel death–effector domain–containing protein, interacts with caspase and BclX$_L$ and initiates cell death" *Proc. Natl. Acad. Sci. U.S.A.* 94:11333–11338 (1997).

James,T., "Normal and Abnormal Consequences of Apoptosis in the Human Heart," Annu. Rev. Physiol. 60:309–325 (1998).

Inohara et al., "Mtd, a Novel Bcl–2 Family Member Activates Apoptosis is the Absence of Heterodimerization with Bcl–2 and Bcl–X$_L$*," *Journal of Biological Chemistry* 273:8705–8710 (1998).

Wellington et al., "Caspase Cleavage of Gene Products Associated with Triplet Expansion Disorders Generates Truncated Fragments Containing the Polyglutamine Tract," *Journal of Biological Chemistry* 273:9158–9167 (1998).

King and Goodbourn, "STAT1 Is Inactivated by a Caspase," *Journal of Biological Chemistry* 273:8699–8704 (1998).

Shimizu et al., "Lamin B Phosphorylation by Protein Kinase Coc and Proteolysis during Apoptosis in Human Leukemia Hl60 Cells," *Journal of Biological Chemistry* 273:8669–8674 (1998).

Janicke et al., "Caspase–3 Is Required for DNA Fragmentation and Morphological Changes Associated with Apoptosis," *Journal of Biological Chemistry* 273:9357–9360 (1998).

Inohara et al., J. Biol. Chem. vol. 273, p. 18675, 1998.*

McCarthy et al., J. Biol. Chem. vol. 274, pp. 16968–16975, 1998.*

* cited by examiner

FIG. 1C agcctgaggaggagacaggagagcgtctggaactgcaggaggacaccgagttcccgtgttgttggcctccagtcctgtgcttgcggagccgtccggcggctgggat
cgagcccgacaATGGGCAACGCGCAGGAGCGGCCCAGCGAGACGATCGACCGCGAGCGGAAGCGGCTGGT
CGAGACGCTGCAGGCGGACTCGGGCCTGCTGCTGGACGCGCTGCTGGCGCGCGGCGTGCTGACCGGGC
CAGAGTACGAGGCGCTATTGGATGCACTGCCCTGATGCCGAGCGACGCTGCTCCTACTGCTGCTGGTG
CAGGGCAAGGGCGAGGCCGCCCTGCGCCTGTGTGCCCAGGGTGCGCTGCCAGCGTACCGGGCGCCGG
ACCCCGCTTGGGACTGGCAGCCACGTGGGTCCGGGACCACCCGCCAGCTATGACCCTCCATGCCCA
GGCCACTGGACGCCCGGAGGCACCCGGCTCCGAGGCTTGCCCCAGAGCTTCAGACCC
TGACGAGGCCGGAAGCTGAGGCTCTAAAGAGGCGACCCCGGAGCCCAGAGCCCCGGAACCCG
AGGCTGAAGCAACCAGAGCCGGAACTGGAGCCAGAACCGGACCCCAGAGCCCGAGCCCGACTTCGA
GGAAAGGGACGAGTCCGAAGATTCCtgaaggccagagctcttgacaggcgtgccccgccatgctgatagcccctgggatgctgctgag
ctgaatcggatgccaccaagctcggtccgactccccccggccgtccgaagccgagtgtgccgagccttggcctctctccaaaaaaaaaaaaaaaaaa
aaaaaaaaaaaaaaaa

FIG. 1D

MGNAQERPSETIDRERKRLVETLQADSGLLLDALLARGVLTGPEYEALDALPDAERRVR
RLLLVQGKGEAACQELLRCAQRTAGAPDPAWDWQHVGPGYRDRSYDPPCPGHWTPE
APGSGTTCPGLPRASDPDEAGGPEGSEAVQSGTPEEPEPELEAEASKEAEPEPEPELEP
EAEAEPEPELEPEPDPEPEPDFEERDESEDS

FIG. 1E

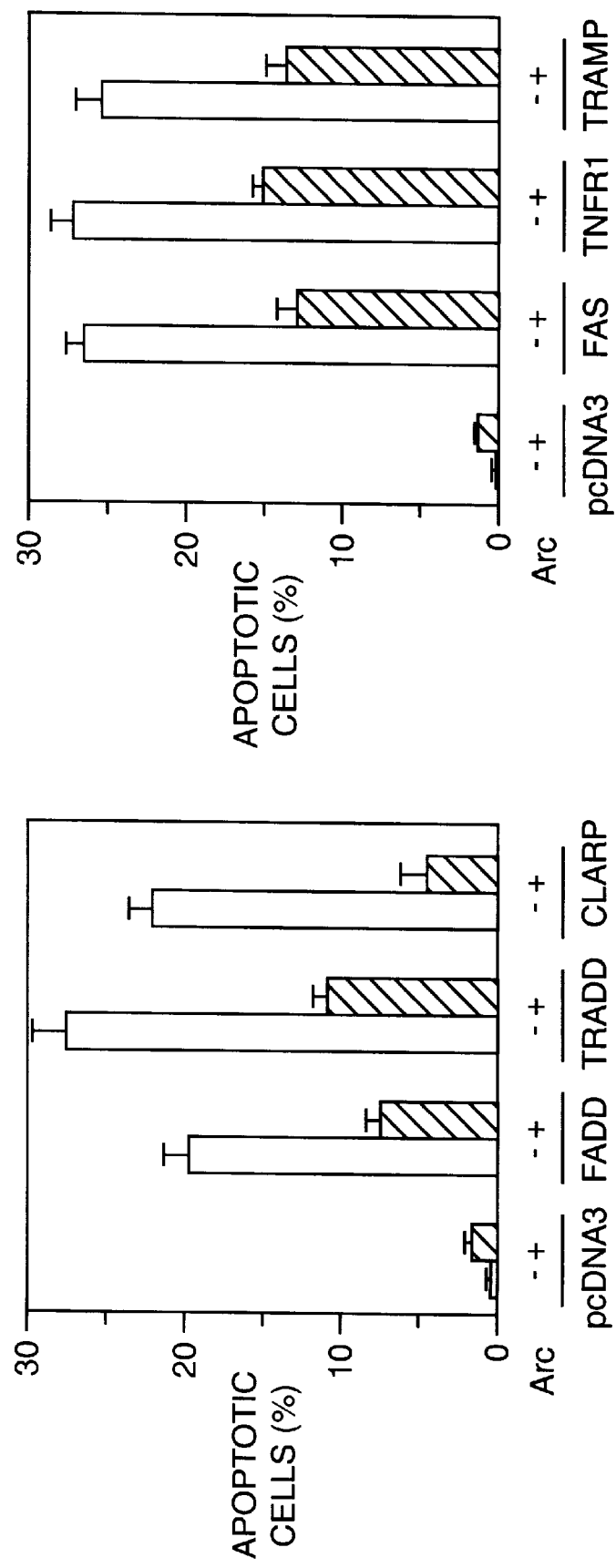

```
MPTIPYHKLADLRYLSRGASGTVSSARHADWRVQVAVKHLHIHTPLLDSE    50
RKDVLREAEILHKARFSYILPILGICNEPEFLGIVTEYMPNGSLNELLHR   100
KTEYPDVAWPLRFRILHEIALGVNYLHNMTPPLLHHDLKTQNILLDNEFH   150
VKIADFGLSKWRMMSLSQSRSSKSAPEGGTIIYMPPENYEPGQKSRASIK   200
HDIYSYAVITWEVLSRKQPFEDVTNPLQIMYSVSQGHRPVINEESLPYDI   250
PHRARMISLIESGWAQNPDERPSFLKCLIELEPVLRTFEEITFLEAVIQL   300
KKTKLQSVSSAIHLCDKKMELSLNIPVNHGPQEESCGSSQLHENSGSPE    350
TSRSLPAPQDNDFLSRKAQDCYFMKLHHCPGNHSWDSTISGSQRAAFCDH   400
KTTPCSSAIINPLSTAGNSERLQPGIAQQWIQSKREDIVNQMTEACLNQS   450
LDALLSRDLIMKEDYELVSTKPTRTSKVRQLLDTTDIQEEFAKVIVQKL    500
KDNKQMGLQPYPEILVVSRSPSLNLLQNKSM                      531
```

FIG. 7A

```
ggcaccagtctctagaaagaagtcagtctcgttcggagaagcagcggctGGCCGTGGGCCatccgggaatgggcgccctcgtgacctagt
gttgcggggcaaaaagggtcttgccggcctcgctcgtgccagggggctatctgggcgcgagcgcgagtgggagccttgggagcgccgcagcag
ggggcacaccggaaccggctgagcgccgagcccggaccatgaacggggaggccatctgcagcgcccATGCCCACCATTCCCTACCA
CAAACTCGCCGACCTGCGCTACCTGAGCCGCCCCTCTGGCACTGTGTCCGCTGTCCGCCCCGCC
ACGCAGAGACTGGCGCGTCCAGGTGGCCGCGTGAAGCACCTGCACACTCCACCTCCGCTGCTCGAC
AGTGAAAGAAAGGATGTcttaagAGAAATTTTACACAAAGCTAGATTTAGTTACATTC
TTCCAATTTTGGGAATTTGCAATGAGCCTGAATTTTTGGGAATAGTTACTGAATACATGCCA
AATGGATCATTAAATGAACTCCTACATAGGAAAACTGAATATCCTGATGTTGCTTGGCCATT
GAGATTTCGCATCCCTGCATGATCATGACTTGAATATCTTATTGGACAATGAATTTCATGTTAAGAT
TTTACTTTCATCATGACTTGAAGACTCAGAATATCTTATTGGACAATGAATTTCATGTTAAGAT
TGCAGATTTTGGTTTATCAAAGTGGCGCATGATCTATATGCCACCTGAAAACTATGAACCTGGACAAAT
CTGCACCAGAAGGAGGACAATTATCAAGCACGATATCAAGCAGTATCACAGTATAGTGTGTTAT
ATCAAGGGCCAGTATCAAGGACAATTATCAAGCACGATATCAAGCAGTATCACATGGGAAGTGTTAT
CCAGAAAACAGCCTTTGAAGATGTCACCAATCCTTTGCCAGATAATGTATAGTGTGTCACAA
GGACATCGACCTGTTATTAATAGAAAGAATGGGCACAAAATCCAGATGATATGAAAGACCATCTTTCTTAAAAT
GATCTCTAATAGAACTTGAACCAGTTGGATGGGCACAAAATCCAGATGATATGAAAGACCATCTTTCTTAAAAT
GTTTAATAGAACTTGAACCAGTTGGATGGGCACAAAATCCAGATGATATGAAAGACCATCTTTCTTAAAAT
ATTCAGCTAAAGAAAAACAAAAGTTACAGAGTGTTTCAAGTGCCATTCACCTATGTGACAAGAA
GAAAATGGAATTATCTCTGAACATATAGTGGTTCTCCCTGAAACTTCATGGTCCCTGCAGCTCCTCAAG
CCCTCTCAGCTCCATGAAAATAGTGGTTCTCCCTGAAACTTCATGGTCCCTGCAGCTCCTCAAG
ACAATGATTTTTATCTAGAAAAAAGCTCCATTTCTGGTTCTCAAAGGCTGCATCACTGTCCTG
GAAATCACAGTTGGGATAGCACCATTTCTGGTTCTCAAAGGCTGCATCACTGTCCTG
ACCACTCCATGCTCTCTTCAGCAATAATAAATCCAACTCCTCAACTGCAGGAAACTCAGAACGTCT
```

FIG. 7B

GCAGCCTGGTATAGCCCAGCAGTGGATCCAGAGCAGTGAAGAAGACATTGTGAACCAAATG
ACAGAAGCCTGCCTTAACCAGTCGCTAGATGCCCTTCTGTCCAGGGACTTGATCATGAAAGA
GGACTATGAACTTGTTAGTACCAAGCCTACAAGGACCTCAAAAGTCAGACAATTACTAGACA
CTACTGACATCCAAGGAGAAGAATTTGCCAAAGTTATAGTACAAAAATTGAAAAGATAACAA
ACAAATGGGTCTTCAGCCTTACCCGGAAATACTTGTGGTTTCTAGATCACCATCTTTAAATTT
ACTTCAAAATAAAAGCATGtaagtgactgttttcaagaagaaaTGTGTTTCATAAAAGGATATTTATATCT
CTGTTGCTTTTGACTTTTTTTATATAAAAATCCGTGAGTATTAAAGCTTTATTGAAGGTTCTTTG
GGTAAATATTAGTCTCCCTCCATGACACTGCAGTATTTTTTTTAATTAATACAAGTAAAAAGT
TGAATTTGgttgaatttgctacadatagtt caattttatgtctcttttgttaacagaaccacttt aaagg at a gt a at ta ttc tt gt tt at a a cag tg cc tta a
ggtatgatgtatttctgatggaagccatttcacattcatgttcttcatgg at tg ttgt ctaagatgcaa ttg at tt gt tc ta gt g a ag t at a t acc ctt tacccac
cagagacagtacagaatcctgccctaaaatcccaggcttaattgccctacaaagggttattaatctcca tt agg at tac at tt a a gt tt t att a
tgaattccctttaaaaatgatatttcaaggtaaaacaataacaa ta a ag a a a a at a at a t at ta at ac cg gc tt cc tg tc cc cat tt ta ac ct ca gc ct tc
cctactgtcaccaaccaagctaaataaagtcaacagcctgatgtg

CIDE-C

| | | |
|---|---|---|
| mCIDE-A | 117 | ------VCKQFKKS-GIARWTFDLVRINFKDFIGCLNVKATMVEMYSVSYDIRCTRFKAVLRNLLRFMSYAAQMTGQFLVYAGTYMLRVLGDTEEQPSPKPSTKGWFM | 217 |
| hCIDE-A | 117 | ------TCSPPKRS-GIARWTFDLVRINPKDFIGCLNVKATMVEMYSVSYDIRCTGLKGLLRSLLRFLSYSAQVTGQFLLYLGTYMLRVLDDKEERPSLRSQAKGRFTCG | 219 |
| mCIDE-B | 117 | ---YGLGREKPKHSKDIARITFDVMKQNPRDLFGSLNVKARDLFGSMCDFQGVGPKVRELLRGTSSQLQGLGHMLLGISSTLRHVEGADRWQWHGQRHLHS | 219 |
| mFSP27 | 125 | KRAQLALSQNFTKKIDVARWTFDLMKINPQDFIGCLNVKATLMDTIYSLSYDLHCYAKRIVKEIVRWTLFSMQATGHMLLGTSSYMQQFLDATEEEQPAKAKPSSLLPACLKMLQ | 239 |

FIG. 14C

DFF-C

| | | |
|---|---|---|
| DREP-1 | 94 | ITTPHGNEAGTGNGELNGGGEGGTTDANNSESARIRQIWGQLQNNLCNVSVMNDADIESLSNMDPNSIVDITGKEFMEQLKDAGRFICAKRNAEDRLNLKTLKAG------AIFCSERY | 209 |
| DFF45 | 103 | --------TAWISQESFDVEHDS-GAGLKWKNVARQLKEDLSSIILLSEEDLQMLVDAPCSDLAQEHTLQQVLDQREEVRQSKQLLQLMIQALEKEGSLLSKQEESKAAF | 216 |

| | | |
|---|---|---|
| DREP-1 | 210 | PEDAEAIDRETGRQLNEAESGQMSTTTTTSNTRTIEVVQC------DNQNTTITITVGEATTCATASGAMGSSAAEAANEANANPNRNPNANGDI | 299 |
| DFF45 | 217 | GEEVDAVDIGSRETSSDVALASHITALREKQAPELSLSSQDLEVTKEDPKALAVALNWDIKKTEIVQEACERHLRLQQTQSLHSLRSISASKASPPGDLQNPKRARQDPT | 331 |

FIG. 14D

```
ggccgccgcactttaagaggctgtgcaggcagacagacctccaggccgctaggggatccgcgccATGGAGGCCGCCCG
GGACTATGCAGGAGGAGCCCTCATCAGGCCTCTGACATTTATGGGATCACAGACTAAGCG
AGTCCTGTTCACCCCGCTCATGCATCCGGCCCGTCCCAGCTCCAACCATGAC
AGGAGCAGCCGGCGTGGGGTGATGGCAGCAGCCTGCAGGAGCTCATCAGCAAGAC
TCTGGATGCCCTCGTCATCGCTACCGGAGTTCTTTCAGACCTTGGTGCTGGAGGAGATGG
CACCGTGGTGGACACAGAAGAGAAGTGGACAAGCCAGCAACACGTCCCCACTTGCT
GATCTTGGAAAAAGGACAGAGTCGGGAATAGCGAGAGTCACCTTCGACTTGTACAGGCTGAAC
CGCCGCCGAAGAGTTCATCGGCTGCCTTAACGTGAGGACTCAAGGGCCACCATGTATGAGATGTACTCC
GTGTCCTACGACATCCGGTGCACGGGACTCAAGGGCGACAGTTTCTCATCTATCTGCTGCGG
TTCCTGTCCTACTCCGCGGATGACAAGGAAGAGCGGCCATCCTCCGGTCACAAGCCAA
GGGCAGGTTCACGTGTGGAtagggatgcaggttgtcgccggctcttgagccaacactgtttcgttgttggctcaatgacg
aatgttgaagatgctttatgttctgagccacatgcacttgaggccgctggtcacgctgctcaggagtggtgcccagaaaaggaaagggctt
ggtggtacatgaagtggggcaagtgggtgccaggcaggtgggtgccctggggggaggcatagagggcccctgggaagcgnacncgc
agcaggcgtgccaggagcgtgtgcatgtgtcagagccattggtccatcatcctctgcaataaacccatcgcaagaatgaccttc
```

FIG. 14E

MEAAARDYAGALIRPLTFMGSQTKRVLFTPLMHPARPFRVSNHDRSSRRGVMASSLQELI
SKTLDALVIATGLVTLVLEEDGTVVDTEEFFQTLGDNTHFMILEKGQKWMPGSQHVPT
CSPPKRSGIARVTFDLYRLNPKDFIGCLNVKATMYEMYSVSYDIRCTGLKGLLRSLLRFL
SYSAQVTGQFLIYLGTYMLRVLDDKEERPSLRSQAKGRFTCG

FIG. 14F

```
gattcggcatgaggccaaatcctgggtttggcctcggtaccgtttggcgcacgaagggcgtgtgcgacgacccaggccaggag
ccagaactattcgctgctcgcaggagcgcacgctgtcgccaagtcggtcaagtcgtcgccggggcgtggctgataggcagtgatttaa
gagacgcggctttgggacaggaggaccgcaccaATGGAGACCGCCAGGGACTACGCGGGAGCCCTCA
TCAGGCCCCTGACATTCATGGGATTGCAGACTAAGAAGGTCCTACTGACCCCCTCA
TACATCCAGCTCGCCCTTTTCGAGTTCAAACATGAGCAAGTACCGAAGTAGCCGGCTGGGG
TGATGGCCAGCAGCCTGCAGGAACTTATCGCAGCAAGACTCTGGATGTCTTAGTCATCA
CAACTGGCCTGGTTACGCTGGTGCTGGAGGAGGACGGCACCGTGGTGGACACAGAG
GAGTTCTTTCAGACCACCGGGTAAGGACAAGAGTATGCTCCCCAGTGCTGAACCCCAAGGACTTCCTCGGCTG
AAATGGACACCGGGTAGTAAGTATGCTCCCCAGTGCTGAACCCCAAGGACTTCCTCGGCTG
AATAGCCAGATGTCAAAGCCACGATGTACGAGATGTACTCGGTGTCCTACGACATCCGATG
TCTCAATGTCAAAGCCACGATGTACGAGATGTACTCGGTGTCCTACGACATCCGATG
CACCAGGTTCAAGGCCGTTCCTGGTCTGTTAAGGAATCTGCGAGGTTTATGTCTCCGAGTACTGGGCGA
GATGACGGGACAGTTCCTGGTCTGTTAAGGAATCTGCGGCACATACATGGCTGGTTCATGTAACcaggc
TACAGAAGAGCAGCCATCCCCCAAGCCTAGACACCCAAAGGCTGGTTCATGTAACcaggc
acagctacagagaggcccaggagcccctgctctctgttataggctgtgggatgcaggggaaggaaggtgcaggggctg
agtagcaggattcctgcaaaggaaaggcgcagaggggcctttcaagcgcttagaaggatcaacagcggagtgtgtgggaactgcg
tggatacgaatcagtttcttgatcctttacatactgtaataaaccagtcacatgagtcgtc
```

FIG. 14G

```
METARDYAGALIRPLTFMGLQTKKVLLTPLIHPARPFRVSNHDRSSRRGVMASSLQELIS
KTLDVLVITTGLVTLVLEEDGTVVDTEEFFQTLRDNTHFMILEKGQKWTPGSKYVPVCK
QPKKSGIARVTFDLYRLNPKDFLGCLNVKATMYEMYSVSYDIRCTRFKAVLRNLLRFM
SYAAQMTGQFLVYAGTYMLRVLGDTEEQPSPKPSTKGWFM
```

FIG. 14H attcggatccatgcacttaccagggctaagatctcagctttatacaaaaagcaagaacaagagaagcacccagcccagaagcaacagggagaga
gtcacctccccatccctgcATGGAGTACCTGTCAGCCTTCAACCCCAATGGCCTGCTAAGGTCAGTAT
CCACTGTGAGCTCGGAGTTAAGCCGAGTTCTGGAACTCAGCTCCTCCACCTCAGCGACCC
TTCCGTCTGTGATCATAAGCGGACAGTCCGGAGACCCTTGCTGCTACGTGGAGTGCCTAAGA
ACTGCTAGATAAGGTCCTGGAGACCAGTGAGGACTTCTTCCAGCTGCTGGAGGACGGAGCAGA
AGGATGGGGACTGCTGTGGACAGGCCAGAGCTGGAGCCCAAGAGTGGGATGTTGTCATACGGCTTG
ATGGTGCTTGAGCAGGAGAAGCCAAAACACAGCCATCGCCCGCATCACCTTCGATGTGTACAAGCA
GACGGGAGAAGCCAAAACACAGACTTCTTTGGCAGCCTCAACGTGAAAGCACATTCTATGGACTCTACTCCA
AAATCCCGAGACCCTCTTTGGCAGCCTCAACGTGAAAGCACATTCTATGGACTCTACTCCA
TGAGCTGTGTGATTTCCAAGGAGTTGGCCCTACACTCAGGGAGCTCCTCCGTGGGACT
TCCTCGCAGCTGCAAGGCCTGCGGCATCGCTGTGGGCATCTCCTCCACCCTTCGCCATGTG
GTGGAGGGGGCTGATCGATGGCAGTGGCACGGGAGAGACACCTCCACTCCtaatgagatcatgctttg
agcctgtgctgaaagactggttccatgtgacacagagggtagtaaggcaccatcaggctggggtctgcagtgtaccaagctgactcca
tcctaacagatgtgcacactgcctgttcctgctgtacatcttcctgaagaatgctacctgtcttccctcactctgcttccactccgtcagaacc
acagcctttgtccctgatcctgctccaccgtaatcgctgcttcatataggttttactgacgcctacccctaagatcctgcatccaacggccactgtcct
agctttactacaagaaaactttccctaaaataaaataaattttccaagaaaataaa

FIG. 14I

MEYLSAFNPNGLLRSVSTVSSELSRRVWNSAPPPQRPFRVCDHKRTVRKGLTAASLQEL
LDKVLETLLRGVLTLVLEEDGTAVDSEDFFQLLEDDTCLMVLEQGQSWSPKSGMLSY
GLGREKPKHSKDIARITFDVYKQNPRDLFGSLNVKATFYGLYSMSCDFQGVGPKRVLRE
LLRGTSSQLQGLGHMLLGISSTLRHVVEGADRWQWHGQRHLHS

METAANSGDSKKPFKVKDVTRNIKKAVCASSLEEIRSKVAEKFEKCDHLPTIHLDSDGT
EIDDEEYFRTLDENTELVAVFPGEHWIDPTHYVTITTPHGNEAGTGNGELNGGGEGDTT
DANNSESARIRQLVGQLQNNLCNVSVMNDADLDSLSNMDPNSLVDITGKEFMEQLKDA
GRPLCAKRNAEDRLNLLKLLKAGAIFCSERYPEDAEAIDREIGRQLNEAESGQMSTTT
TSNTRTIEVVQCDNQNTTITITVGEATTCATASGAMGSSAAEAANEANANPNRNPNA
NGDI

FIG. 14L

```
gctgctccgagctccgcgtccgtcgcgtagattcgcgtcgcgtcgacctcagaggcgggcccgtaagcgctacgcgtttgaccccccga
gtccctctgttcccgaaggggccggccgcgtctttctccgaccccgcctcctctccttcccgcctcctctttcccattaccggagccgaagcccccagc
cagggcggggcggccgcccgagctccggaagaagcgccatctccgcctccaccATGGAGCCCCACCGCA
CCGTCCCTCACCGAGGAGGACCTCACTGAAGTGAAGAAGACGCCTTAGAAATTT
ACGTGTATACCTGTGTGAGAGAGAGATCATAGCTGAGAGAAATTTGATCATCTACGTGC
AAAAAAATACTCAGTAGAGAGAAGAGACACTGAAGAAATTTCTTGTCGAACATCAAGTA
GAAAAAGGGCTGGAAAAATTGTTAGACTACTTACAGGAAAAACCCAAAAGGTCTGGAC
AcCCTTGTTGAATCTATTCGGCGAGAAAAAAACACAGAACTTcCTgatacagaagattacagatgaa
gtgctgaaaCTTAGAAATATAAAACatagaaCATCTGAAAGGACTAAAATGTAGCAGTTGTGA
ACCTTTCCAGATGGAGCCACGAACAACCTCTCCAGATCAAATTCAGATGAGAGTAA
TTTCTCTGAAAAACTGAGGGCATCATGTACCATCCAGAAGGAGAATCCAG
CACGACGCCCTTTTTTCTACTAATTCTTCTCTGAATTTGCCTGTTCTAGAAGTAGGC
AGAACTGAAAATACCATCTTCTCTTCAACTACACTTCCCAGACCTGGGACCAGGG
GCTCCTCCTTTGCCACCAGATGTTTCCCTTAAGAGAATAACGAATCTGTGCAAACTCT
AGTGAGATGTTTCTTCCCTTAAGAGAATATGACTTTTTTATAAATGGCTGTAATCATTGTACATTGATGATGTCTTTAAATGCATGTA
attttaatgatgacaaaaaaatgttttagaattaaaaaagcatactTctaggatagcaacatcatgttgatcatgtacttgtgataattcttttt
agcatactttgtaatataggatttttagaattaaaaaagcatactctaggatagcaacatcatgttgatcatgtacttttgtaattcttttt
tcctttttaaggtcttttcagtactttttaaatatttctattttgagaataggaccttactaggaaga
acgtttttcctcagtgcatttgtgctagaaatttcaagagtctaatagtcttgccagtcattcagcagcaaatttcagcattaagctgttcctgtc
agtaataaaaccggtcactgatgggaaaactgccaataATAAAATAAAAATCTCTTTTCCACTCCATTGTC
GTATAGGCATGTAAACAGCCTCTTTTGATACTGGAGGAACACTTGATGGAGTGTGA
GCCACCTAAGATCTCGGTTGCCAAAATTCATTTCTAATTAACCTTACTAATTATACT
ACTTTGTTAGGATTTCACATTCTGGCTTAATCATTTCATTCCTAAAGAAAAATAT
CTTGGCCTAAACCTCAGTTATTACATGTAATTTGATGAGGTATTTGGTATTTGTTCCN
TT
```

FIG. 20A

MEPTAPSLTEEDLTEVKKDALENLRVYLCEKIIAERHFDHLRAKKILSREDTEEISCRTSS
RKRAGKLLDYLQENPKGLDTLVESIRREKTQNFLIQKITDEVLKLRNIKLEHLKGLKCSS
CEPFPDGATNNLSRSNSDESNFSEKLRASTVMYHPEGESSTPFFSTNSSLNLPVLEVGRT
ENTIFSSTTLPRPGDPGAPPLPPDLQLEEEGTCANSSEMFLPLRSRTVSRQ

FIG. 20B

```
cacagcctgattcccggagcccgagccctagtctgggcggtggcgcggcggaagaggacgccatcccgcctggccATGG
AGGCTCCCGCACCCGTCCCCTCACGGAGGAGGATTTGACTGAAGTGAAGAAGGACGCT
TTAGAGAATTTACGTGTGTTTACCTGTGTGAGAAATCATAGCTGAGAGACATTTGAT
CATCTACGTGCAAAAAAAAAATACTAAGAAACGGGCTGGGAATTCATAGAAGAAATTTCTTGCCG
AACTTCAAGTAGAAAACGGGCTGGGAATCCATCCAGGGAGAAGTTGTTAGACTACTTACAGGAGAACCCA
GGGGCCTGGACACCCTGGTGGGAATCCATCCAGGGAGAAACACAGAGCTTCCTG
ATTCAGAAGATAACGGATGAGGTGCTAAAGCTTCGGAATATAAAACTGGAGCACCT
CAAAGCCCTGAAGTGCAGCAGCTGTGAGCCCTTTGCAGCCCGGAGCCACCAACAACC
TCTCTAGGTGCAATTCCGATGAGAGGAACAGAGAGCATCCACTG
TCATGTACCACCCGGAGGGAGAGTCCAGCACGGCTCCCTTCTCTTATGGCGTCGT
CCCTGAACTTGCCAGTCCTGGAAGTTGGCAGGACTGCTTGAAAACAGCAGCTTCTCTTCAG
CCACTCTTCCTCGACCTGGGGACCCCTGGGCCTCCCCCCTTTGCCCCAGACCTTCGGTT
GAAGAGGGGGAAGTTGTGAAACTCAAGTGAGATGTTTCTCCCCAGATGATGTTTCAGCCTAGGATGTGTAAAGAACACAGAGATCTCTCT
GGCTCTTTCACGCCAATGAtacatcaccgctagttgttttactagtgatgtgaagggagccatctttctat
acaaaccacggtgacaggtcactcacattcgatgctgcttaaatcagtgtacacattcctgtaaataggattgttagggtaaagaagc
gctctgggcggcgtggtgtgaatcatgtgtgtgacttccatagtgtgcattttgagaaaacaactgtgtgattgggaataatgtttttaggtgtgtatttgaactttcata
agattaattatcggcagtctgcagtatatttagcagtgaagctgtgttgtttcaggaaagctggacacggaaagctgccgacacactcagcagtgtc
ttttcccactgatctgtggcagtatatttagcagtgaagctgtgttgtttcaggaaagctggacacggaaagctgccgacacactcagcagtgtc
ccactcctagtctgagaagccgtcgggttcacaggccttgtgtcctcagtcttatcttaaaggatgttatcttgcaggcgcatcacttgtaattaatg
caccctgccagcgtgagtgttgactaaagtcctcgctctgagccgtttagtgttgcatcaggcagcaccagctccatccgtgttcttactgcttacaagtttgac
gatgatacttgtaattgactaaagtcctcgctctgagccgtttagtgttgcatcaggcagcaccagctccatccgtgttcttactgcttacaagtttgac
actgacaggatgtgccgtgccagtggccagtgtgcttagtgttcttgtttaattataattataatttcttgacatctcattctgacatctcattctattattaaaattaaga
taactttacacatttaaaaatgctgattgtcttgtttaattataattataatttcttgacatctcattctgacatctcattctattattaaaattaaga
aatgaaaattgctattaacaataaagtttttttaatgtaaaaaaaaaaaaaaa
```

FIG. 20C

MEAPAPSLTEEDLTEVKKDALENLRVYLCEKIIAERHFDHLRAKKILSREDTEEISCRTSS
RKRAGKLLDYLQENPRGLDTLVESIRREKTQSFLIQKITDEVLKLRNIKLEHLKGLKCSS
CEPFAAGATNNLSRCNSDESNLSEKQRASTVMYHPEGESSTAPFFSMASSLNLPVLEVG
RTENSSFSSATLPRPGDPGAPPFPPDLRLEEGGSCGNSSEMFLPLRSRALSRQ

FIG. 20D

```
AGCGAGCTTGCAGCCTCACCGACGAGTCTCAACTAAAAGGGACTCCCGGAGCTAGG
GGTGGGGACTCGGCCTCACACAGTGAGTGCCGGCTATTGGACTTTTGTCCAGTGACA
GCTGAGACAACAAGGACCACGGGAGGAGGTGTAGGAGAGAAGCGCCGCGAACAGC
GATCGCCCAGCACCAAGTCCGCTTCCAGGCTTTCGGTTTCTTTGCCTCCATCTTGGGT
GCGCCTTCCCGGCGTCTAGGGGAGCGAAGGCTGAGGTGGCAGCGGCAGGAGAGTCC
GGCCGCGACAGGACGAACTCCCCACTGGAAAGGATTCTGAAAGAAATGAAGTCAG
CCCTCAGAAATGAAGTTGACTGCCTGCTGGCTTTCCTGTTGACTGGCCCGGAGCTGT
ACTGCAAGACCCTTGTGAGCTTCCCTAGTCTAAGAGTAGGATGTCTGCTGAAGTCAT
CCATCAGGTTGAAGAAGCACTTGATACAGATGAGAAGGAGATGCTGCTCTTTTTGTG
CCGGGATGTTGCTATAGATGTGGTTCCACCTAATGTCAGGGACCTTCTGGATATTTT
ACGGGAAGAGGTAAGCTGTCTGTCGGGACTTGGCTGAACTGCTCTACAGAGTGA
GGCGATTTGACCTGCTCAAACGTATCTTGAAGATGGACAGAAAGCTGTGGAGACC
CACCTGCTCAGGAACCCTCACCTTGTTTCGGACTATAGAGTGCTGATGGCAGAGATT
GGTGAGGATTTGGATAAATCTGATGTGTCCTCATTAATTTTCCTCATGAAGGATTAC
ATGGGCCGAGGCAAGATAAGCAAGGAGAAGATTTCTTGGGACCTTGTGGTTGAGTT
GGAGAAACTAAATCTGGTTGCCCCAGATCAACTGGATTTATTAGAAAAATGCCTAA
AGAACATCCACAGAATAGACCTGAAGACAAAAATCCAGAAGTACAAGCAGTCTGTT
CAAGGAGCAGGGACAAGTTACAGGAATGTTCTCCAAGCAGCAATCCAAAAGAGTCT
CAAGGATCCTTCAAATAACTTCAGGCTCCATAATGGGAGAAGTAAAGAACAAAGAC
TTAAGGAACAGCTTGGCGCTCAACAAGAACCAGTGAAGAAATCCATTCAGGAATCA
GAAGCTTTTTTGCCTCAGAGCATACCTGAAGAGAGATACAAGATGAAGAGCAAGCC
CCTAGGAATCTGCCTGATAATCGATTGCATTGGCAATGAGACAGAGCTTCTTCGAGA
CACCTTCACTTCCCTGGGCTATGAAGTCCAGAAATTCTTGCATCTCAGTATGCATGGT
ATATCCCAGATTCTTGGCCAATTTGCCTGTATGCCCGAGCACCGAGACTACGACAGC
TTTGTGTGTGTCCTGGTGAGCCGAGGAGGCTCCCAGAGTGTGTATGGTGTGGATCAG
ACTCACTCAGGGCTCCCCCTGCATCACATCAGGAGGATGTTCATGGGAGAATCATGC
CCTTATCTAGCAGGGAAGCCAAAGATGTTTTTTATTCAGAACTATGTGGTGTCAGAG
GGCCCAGCTGGAGACAGCAGCCTCTGGAGGGTGGATGGGCCAGCGATGAAGAATGT
GGAATTCAGGGCTCAGAAGCGAGGGCTGTGCACAGTTCACCGAGAAGCTGACTTCT
TCTGGAGCCTGTGTACTGCGGACATGTCCCTGCTGGAGCAGTCTCACAGCTCACCAT
CCCTGTACCTGCAGTGCCTCTCCCAGAAACTGAGACAAGAAGAAAACGCCCACTCC
TGGATCTTCACATTGAACTCAATGGCTACATGTATGATTGGAACAGCAGAGTTTCTG
CCAAGGAGAAATATTATGTCCTGGCTGCAGCACACTCTGAGAAGAAACTTATCCTCT
CCTACACATAAGAAACCAAAGGCTGGGCGTAGTGGCTCACACCTGTAATCCCAGC
ACTTTGGGAGGCCAAGGAGGGCAGATCACTTCAGGTCAGGAGTTCGAGACCAGCCT
GGCCAACATGGTAAACGCTGTCCCTAGTAAAATACAAAATTAAAAAAAAAAAA
AAAAA
```

FIG. 21A

MSAEVIHQVEEALDTDEKEMLLFLCRDVAIDVVPPNVRDLLDILRERGKLSVGDLAELL
YRVRRFDLLKRILKMDRKAVETHLLRNPHLVSDYRVLMAEIGEDLDKSDVSSLIFLMKD
YMGRGKISKEKISWDLVVELEKLNLVAPDQLDLLEKCLKNIHRIDLKTKIQKYKQSVQG
AGTSYRNVLQAAIQKSLKDPSNNFRLHNGRSKEQRLKEQLGAQQEPVKKSIQESEAFLP
QSIPEERYKMKSKPLGICLIIDCIGNETELLRDTFTSLGYEVQKFLHLSMHGISQILGQFAC
MPEHRDYDSFVCVLVSRGGSQSVYGVDQTHSGLPLHHIRRMFMGESCPYLAGKPKMFF
IQNYVVSEGPAGDSSLWRVDGPAMKNVEFRAQKRGLCTVHREADFFWSLCTADMSLL
EQSHSSPSLYLQCLSQKLRQERKRPLLDLHIELNGYMYDWNSRVSAKEKYYVWLQHTL
RKKLILSYT

FIG. 21B

COMPOSITIONS AND METHODS FOR IDENTIFYING APOPTOSIS SIGNALING PATHWAY INHIBITORS AND ACTIVATORS

This invention was made in part with government support under grant CA-64556 from the National Institute of Health. The government has certain rights in the invention.

FIELD OF THE INVENTION

The invention generally relates to compositions and methods for identifying apoptosis signaling pathway inhibitors and activators.

BACKGROUND OF THE INVENTION

Most cells in the body die through a non-inflammatory, energy-dependent form of cell death called apoptosis. Recent research into the molecular mechanisms of apoptosis has revealed that apoptosis is a genetically programmed process that can become deranged when the components of the cellular apoptotic machinery are mutated or present in inappropriate quantities. Dysregulation of apoptosis is associated with the pathogenesis of a wide array of diseases; cancer, neurodegeneration, autoimmunity, heart disease, and other disorders. Some diseases associated with increased apoptosis include AIDS, neurodegenerative disorders (e.g., Alzheimer's disease, Parkinson's disease, amyotrophic lateral sclerosis, retinitis pigmentosa), aplastic anemia, ischemic injury (e.g., myocardial infarction, stroke, reperfusion injury), and toxin-induced (e.g., alcohol induced) liver disease. Thus, apoptosis is critical not only during development and tissue homeostasis, but also in the pathogenesis of a variety of diseases. Products of genes involved in the regulation and execution of apoptosis are therefore potentially excellent targets for diagnosis and therapeutic intervention in disease processes, and they offer renewed hope for cures and treatments for a wide array of maladies [See Review by Rudin and Thompson, *Ann. Rev. Med.* 48:267–81 (1997)].

To date, various signaling pathways in apoptosis have been elucidated. Significant progress in defining the extracellular signaling mechanisms regulating apoptosis has been made in lymphocytes. B and T cells both express a wide variety of cell surface receptors that can either induce or inhibit apoptosis. The largest related group of these receptors, with at least 12 members, is the tumor necrosis factor (TNF) receptor (TNFR) family. These are characterized by cysteine-rich pseudorepeats in the N-terminal extracellular domains, through which each member binds to one or more of a family of TNF-related proteins. Under various experimental conditions, several of these receptors (including TNFR2, CD40, and CD30) inhibit apoptosis; others (including TNFR1 and Fas) induce apoptosis in lymphocytes.

The death-inducing receptors TNFR1 and Fas share a related intracellular sequence known as the death domain. FADD (Fas associated death domain protein), RIP, and TRADD (TNFR-associated death domain protein), can heterodimerize with the death domains of these receptors. FADD and RIP interact directly with Fas, whereas TRADD appears to bind only TNFR1. Over expression of any of these cytoplasmic proteins induces apoptosis. The TNFR1-TRADD complex forms only when TNFR1 has engaged extracellular TNF, and the complex was recently shown to secondarily bind FADD by heterodimerization of the C-terminal death domains of TRADD and FADD. Mutations in the N-terminal portion of FADD prevented TNFR1-induced apoptotic signaling. In addition, the TNFR1-TRADD complex was found to interact with TRAF2 in a pathway required for TNFR1-induced NFκB activation. These findings suggested that TRADD may serve primarily as a linker between TNFR1 and multiple downstream signaling pathways, including FADD-mediated apoptosis. Interestingly, over expression of the death domain of TRADD or RIP alone is sufficient to induce apoptosis, whereas FADD over expression induces apoptosis only if the N-terminal (effector) domain is intact. FADD mutants with altered death domains that are unable to bind Fas are still lethal. Activation of FADD or similar effector proteins may be essential for both TNFR1- and Fas-mediated apoptosis. Recently, FADD has been shown to interact with a novel member of the ICE protease family known as MACH or FLICE. FADD can recruit this protease to the ligand-engaged Fas receptor and promotes the cleavage of the FLICE prodomain, presumably activating the protease. Although such activation may be sufficient to induce apoptosis, Fas may also activate other signaling molecules that contribute to programmed cell death.

Sequential cytological and biochemical changes are associated with the cellular apoptotic process. The cytoplasm condenses, and the endoplasmic reticulum dilates to form vesicles which fuse with the cell membrane, producing characteristic cellular morphology. Changes in the nuclei include the formation of dense crescent shaped aggregates of chromatin, nucleolus fragmentation, and formation of vesicles at or on the nuclear membrane. During apoptosis, endonucleases present in the cell cut the DNA in the linker regions between nucleosomes to release DNA fragments in integer multiples of 180–190 base pairs [J. J. Cohen et al., *J. Immunol.* 132:38–42 (1984)]. The pattern of cleavage is believed to result from the vulnerability of the linker DNA between the nucleosomes to endonucleases. However, the elucidation of the cellular signaling transduction mechanisms beginning with the apoptosis inducing agent and leading to DNA fragmentation and apoptosis have not been fully determined.

Better understanding and elucidation of various strategic targets in the cellular signaling transduction machinery that leads to DNA fragmentation and apoptosis would provide suitable compounds for modulating cell growth and proliferation by regulation of the apoptotic signaling pathway. What is required are suitable methods and compositions for the identification of compounds that have therapeutic utility where cell growth or proliferation is aberrant, for example, as anti-neoplastic agents.

SUMMARY OF THE INVENTION

The present invention generally relates to compositions and methods for identifying apoptosis signaling pathway inhibitors and activators and more particularly, methods and compositions for screening compounds and identifying compounds that will modulate the interactions of the various compositions identified in the present invention; ARC, RICK and the CIDE family of activators (CIDE-A, CIDE-B, DREP-1) with other members of the signaling pathway, i.e., their substrates or ligands. It is not intended that the present invention be limited to particular cell death signaling pathways. The present invention contemplates that the methods and compositions described herein will be useful with a variety of apoptosis-signaling receptors, to identify compounds that will modulate the interactions of ARC, RICK and the CIDE family of activators with other members of the apoptosis signaling pathway, i.e., their substrates or ligands.

In one embodiment, the present invention contemplates an isolated nucleic acid encoding at least a fragment of the RICK protein(RIP-like interacting CLARP kinase), that functions as a positive regulator of apoptosis, having the amino acid sequence (1–531) set forth in SEQ ID NO:1. It is not intended that the present invention be limited by the size or nature of the fragment. In one embodiment, said nucleic acid encodes full-length RICK as set forth in (SEQ ID NO:1) and said nucleic acid comprises SEQ ID NO:2 are contemplated. In another embodiment, the said RICK protein has a mutation at the ATP-binding site, in which the lysine residue is replaced by methionine at position 38 of the amino acid sequence set forth in SEQ ID NO:3. In another embodiment, said nucleic acid encodes a fragment. It is not intended that the present invention be limited by the nature or size of the fragment. For example, fragements comprising either residues 54–531 (SEQ ID NO:4), residues 248–531 (SEQ ID NO:5), or residues 365–531 (SEQ ID NO:6), or residues 1–365 (SEQ ID NO:7) of the amino acid sequence set forth in SEQ ID NO:1. In yet another embodiment, said nucleic acid encodes a fusion protein.

It is not intended that the present invention be limited as to the specific nature of the nucleic acid encoding the peptides described above. In one embodiment, said nucleic acid is contained in a vector. In another embodiment, said vector is in a host cell.

In one embodiment, the present invention contemplates screening compounds and identifying compounds that modulate the interactions of the RICK kinase and its substrates, and intracellular proteins in the apoptosis pathway, and in particular CLARP. Furthermore, the present invention contemplates identifying RICK inhibitors and RICK kinase binding substrates, and compounds that will modulate the interaction of RICK kinase with its substrates as well as RICK kinase activity.

In one embodiment, the present invention contemplates identifying compounds that modulate the interaction of RICK kinase, which binds to CLARP. In other embodiments, the present invention contemplates identifying compounds that modulate the interaction of RICK, which binds to FADD.

In preferred embodiments, RICK (and in particular, fragments of RICK as described above) are useful in drug screening assays designed to identify drugs that interfere with the specific binding of RICK kinase with their substrate as well as RICK kinase activity, and thereby block the activation of downstream signaling molecules. In other embodiments, the present invention contemplates identifying compounds that modulate the interaction of RICK, which may bind to substrates other than FADD or proteins other than CLARP.

In general, the present invention contemplates identifying inhibitors that modulate apoptosis mediated by the CD95 pathway, by modulating the interaction of RICK kinase.

In other embodiments, the invention provides an isolated polypeptide, or a fragment thereof, having RICK kinase-specific binding affinity. The invention provides nucleic acids encoding the RICK polypeptide and RICK fragments as part of expression vectors for introduction into cells. The invention provides methods of identifying intracellular molecules which interact with RICK or RICK fragments, as well as exogenous agents (i.e., drugs) which disrupt the binding of RICK and/or fragments thereof to such intracellular targets.

The claimed polypeptide RICK and RICK fragments (see above) find particular use in screening assays for agents or lead compounds for agents useful in the diagnosis, prognosis or treatment of disease, particularly disease associated with undesirable cell growth, and dysregulation of apoptosis.

It is not intended that the present invention be limited by the species (human, murine, rat, etc.) of the binding ligands described above. The polypeptide RICK and RICK fragments shown below may bind across species. Moreover, the nucleic acid sequences described herein allow for the identification of homologues in other species by various methods, including but not limited to amplification (e.g., PCR) using primers designed from the nucleic acid sequence of one species (e.g., human) on the nucleic acid template of another species (e.g., mouse).

In other embodiments, a purified oligonucleotide capable of selectively hybridizing to the nucleic acid molecule set out in FIGS. 7B and 7C (SEQ ID NO:2) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIGS. 7B and 7C (SEQ ID NO:2). In a preferred embodiment, said oligonucleotide is labelled.

The present invention also contemplates complexes of ligands. In one embodiment, the present invention contemplates a composition, comprising a RICK-kinase complex comprising a purified peptide having at least a portion of the amino acid sequence set forth in SEQ ID NO:1 specifically bound to CLARP (or other substrate). Again, the peptides bound specifically to CLARP may be full-length RICK or a fragment defined by a portion of the amino acid sequence as set forth in SEQ ID NO:1. The peptide may be part of a fusion protein. The complex can also contain other ligands, such as FADD and/or the CD95 receptor. The complexes can be used in drug screening assays to identify inhibitor molecules that block CD95-mediated apoptosis (as described below).

As noted above, the present invention contemplates compound screening assays. In one embodiment, the present invention contemplates a method for compound screening, comprising: a) providing: i) a RICK peptide comprising at least a portion of the amino acid sequence set forth in SEQ ID NO:1, wherein said portion is capable of binding to a substrate or protein such as CLARP and/or FADD, ii) RICK substrate, and iii) one or more compounds for screening; b) mixing, in any order, said RICK kinase, said RICK substrate and said one or more compound; and c) measuring the extent of binding of said peptide to said RICK substrate FADD and/or protein CLARP.

One such assay involves forming mixtures of 1) RICK (or fragments thereof) and 2) an intracellular RICK-binding substrate, in the presence or absence of 3) a prospective drug candidate. The mixtures are made under conditions that permit the binding of the intracellular RICK-binding substrate to RICK (or fragments thereof) and the mixtures are then analyzed for the presence of such binding. A difference in such binding in the presence of such a drug candidate indicates that the agent is capable of modulating the binding of RICK (or fragments thereof) to an intracellular RICK-binding substrate.

Another such assay involves forming mixtures of 1) RICK (or fragments thereof) and 2) an intracellular RICK-binding substrate, in the presence or absence of 3) a prospective drug candidate. The mixtures are made under conditions that permit the phosphorylation of the intracellular RICK-binding substrate, such as FADD, by RICK (or fragments thereof) and the mixtures are then analyzed for phosphorylation. A difference in phosphorylation in the presence of such a drug candidate indicates that the agent is capable of modulating the ability of RICK (or fragments thereof) to phosphorylate an intracellular RICK-binding substrate.

Again, the peptides may be full-length RICK or a fragment defined by a portion of the amino acid sequence as set forth in SEQ ID NO:1. The peptide may also be part of a fusion protein. The present invention also contemplates embodiments where either the peptide or kinase is bound to other ligands. These complexes can be used in the compound screening assay described above.

In another preferred embodiment, the present invention contemplates an isolated nucleic acid encoding at least a fragment of the Apoptosis Repressor Protein, ARC having the amino acid sequence (1–208) set forth in SEQ ID NO:8. It is not intended that the present invention be limited by the size or nature of the fragment. In one embodiment, said nucleic acid encodes full-length ARC as set forth in (SEQ ID NO:8) and said nucleic acid comprises SEQ ID NO:9. In another embodiment, said nucleic acid encodes a fragment comprising either residues 1–106 (SEQ ID NO:10) or residues 107–208 (SEQ ID NO:11) of the amino acid sequence set forth in SEQ ID NO:8. In yet another embodiment, said nucleic acid encodes a fusion protein.

In other embodiments, a purified oligonucleotide capable of selectively hybridizing to the nucleic acid molecule set out in FIG. 1D (SEQ ID NO:9) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIG. 1D(SEQ ID NO:9). In a preferred embodiment, said oligonucleotide is labelled.

It is not intended that the present invention be limited as to the specific nature of the nucleic acid encoding the peptides described above. In one embodiment, said nucleic acid is contained in a vector. In another embodiment, said vector is in a host cell.

In preferred embodiments, over expression of ARC or fragments thereof, in an in vitro cell system can be used for identifying similar inhibitors that inhibit the enzymatic activity of caspase-8 and thereby block CD95-mediated apoptosis. Also, identification of ARC-like inhibitory compounds may be particularly useful for gene therapy, for e.g., for the treatment of diseases that are characterized by inappropriately increased cell death in muscle tissue and cardiac disorders.

In other preferred embodiments, the present invention contemplates an isolated nucleic acid encoding at least a fragment of the Human CIDE-A protein (Cell Death inducing DFF45-like effector-A) having the amino acid sequence (1–219) set forth in SEQ ID NO:12. It is not intended that the present invention be limited by the size or nature of the fragment. In one embodiment, said nucleic acid encodes full-length CIDE-A as set forth in (SEQ ID NO:12) and said nucleic acid comprises SEQ ID NO:13. In another embodiment, said nucleic acid encodes a fragment comprising either residues 1–107 (SEQ ID NO:14), or residues 108–200 (SEQ ID NO:15) of the amino acid sequence set forth in SEQ ID NO:12. In yet another embodiment, said nucleic acid encodes a fusion protein.

In other embodiments, a purified oligonucleotide capable of selectively hybridizing to the nucleic acid molecule set out in FIG. 14E (SEQ ID NO:13) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIG. 14E (SEQ ID NO:13). In a preferred embodiment, said oligonucleotide is labelled.

In other preferred embodiments, the present invention contemplates an isolated nucleic acid encoding at least a fragment of the Mouse CIDE-A protein (Cell Death inducing DFF45-like effector-A) having the amino acid sequence (1–217) set forth in SEQ ID NO:16. It is not intended that the present invention be limited by the size or nature of the fragment. In one embodiment, said nucleic acid encodes full-length CIDE-A as set forth in (SEQ ID NO:16) and said nucleic acid comprises SEQ ID NO:17.

In yet other embodiments, a purified oligonucleotide capable of selectively hybridizing to the nucleic acid molecule set out in FIG. 14G (SEQ ID NO:17) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIG. 4G (SEQ ID NO:17). In a preferred embodiment, said oligonucleotide is labelled.

In yet other preferred embodiments, the present invention contemplates an isolated nucleic acid encoding at least a fragment of the Mouse CIDE-B protein (Cell Death inducing DFF45-like effector-B) having the amino acid sequence (1–219) set forth in SEQ ID NO:1 8. It is not intended that the present invention be limited by the size or nature of the fragment. In one embodiment, said nucleic acid encodes full-length CIDE-B as set forth in (SEQ ID NO:18) and said nucleic acid comprises SEQ ID NO:19. In yet another embodiment, said nucleic acid encodes a fusion protein.

In yet other embodiments, a purified oligonucleotide capable of selectively hybridizing to the nucleic acid molecule set out in FIG. 14I (SEQ ID NO:19) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIG. 14I (SEQ ID NO:19). In a preferred embodiment, said oligonucleotide is labelled.

In other preferred embodiments, the present invention contemplates an isolated nucleic acid encoding at least a fragment of the Drosophila DREP-1 protein (DFF45-homologue) having the amino acid sequence (1–299) set forth in SEQ ID NO:20. In one embodiment, said nucleic acid encodes full-length DREP-1 as set forth in (SEQ ID NO:20) and said nucleic acid comprises SEQ ID NO:21. It is not intended that the present invention be limited by the size or nature of the fragment. In one embodiment, said nucleic acid encodes a fusion protein.

In yet other embodiments, a purified oligonucleotide capable of selectively hybridizing to the nucleic acid molecule set out in FIG. 14K (SEQ ID NO:21) is provided, wherein said oligonucleotide comprises a contiguous sequence of at least ten nucleotides (and more preferably at least fifteen nucleotides, and still more preferably at least twenty nucleotides) completely complementary to said nucleic acid molecule set out in FIG. 14K (SEQ ID NO:21). In a preferred embodiment, said oligonucleotide is labelled.

It is not intended that the present invention be limited as to the specific nature of the nucleic acid encoding the various peptide compositions described above. In one embodiment, said nucleic acid is contained in a vector. In another embodiment, said vector is in a host cell.

In preferred embodiments, therapeutic compositions of CIDEs can be used for the treatment of diseases and/or cancer, as DFF45-inhibitable effectors that promote

DESCRIPTION OF FIGURES

FIG. 1 shows the structure, sequence and alignment of ARC with related proteins.

FIG. 1(A) shows the schematic structure of human ARC. Caspase recruitment domain (CARD) and proline/glutamic acid-rich domains are shown as closed and open boxes.

FIG. 1(B) shows the aligned amino acid sequences of human (SEQ ID NO:8) and rat ARC (accession number U40627 set forth in SEQ ID NO:22). The identical residues in human (SEQ ID NO:8) and rat ARC (SEQ ID NOS:8 and 22) are indicated by asterisk.

FIG. 1(C) shows the alignment of the amino acid sequences of CARD domains of ARC, caspase-9 (Genebank accession number U56390 set forth in SEQ ID NO:23), human caspase-2 (U13021 set forth in SEQ ID NO:24), RAIDD (U79115 set forth in SEQ ID NO:25) and Apaf-1 (AF013263 set forth in SEQ ID NO:26). The conceived residues in human (SEQ ID NO:8) and rat ARC (SEQ ID NO:22) are indicated by asterisk.

FIG. 1(D) shows the human ARC cDNA sequence (SEQ ID NO: 9). Capital letters indicate the sequence coding for the protein.

FIG. 1(E) shows the amino acid sequences of human ARC (accession number U40627 set forth in SEQ ID NO:8).

FIG. 3 shows ARC is a negative regulator of apoptosis. 293T cells transfected with pcDNA3, pcDNA3-ARC-Flag, and various expression plasmids, were visualized with β-galactosidase substrate and scored for morphological feature of apoptosis.

FIG. 3(C) shows ARC inhibits FADD, TRADD and CLARP-induced apoptosis.

FIG. 3(D) shows ARC inhibits apoptosis induced by death receptors(Fas, TNFR1, TRAMP).

FIG. 4 shows ARC suppresses the enzymatic activity of caspase-8 in intact cells.

FIG. 7 shows the nucleotide (SEQ ID NO:2) and amino acid (SEQ ID NO:1) sequence of RICK.

FIG. 7(A) shows the deduced amino acid (SEQ ID NO:1) sequence of RICK. The deduced amino acid sequence was derived from three independent cDNA clones.

FIGS. 7(B) and 7(C) shows the cDNA sequence of RICK (SEQ ID NO:2).

FIG. 8 shows the domain structure and alignment of RICK.

FIG. 8(A) is a schematic representation of RICK. Numbers corresponds to amino acid residues shown in panel A. The kinase domain and "caspase-recruitment domain" (CARD) are as indicated.

FIG. 8(B) shows the alignment of kinase domains of RICK (GenBank AF027706 set forth in SEQ ID NO:27) and RIP (U25995 set forth in SEQ ID NO:28). Hydrophobic and aromatic amino acid residues are shown by reverse highlight. Positive and negative charged residues are shown by dark and light gray highlight, respectively. α helix and β strand breakers are shown by bold letters. Lys residues of the ATP binding site and catalytic Asp residues are shown by arrows. Identical and conserved residues are shown by stars and dots, respectively.

FIG. 8(C) shows the alignment of CARDs of RICK (SEQ ID NO:27), caspase-1 (X65019 set forth in SEQ ID NO:30), caspase-2 (U13021 set forth in SEQ ID NO:24), RAIDD (U79115 set forth in SEQ ID NO:25), c-IAP-1 (L49431 set forth in SEQ ID NO:29), Apaf-1 (AF013263 set forth in SEQ ID NO:26) and CED-4 (X69016 set forth in SEQ ID NO:38). Conserved residues are shown by dots.

Flag-RICK (●). Tagged caspase-8 was immunoprecipitated with mAb to AU1 and the enzymatic activity was determined in triplicate with the fluorogenic substrate DEVD-AMC. The DEVD-AMC cleavage is given in arbitrary units. To confirm equal expression of caspase-8-AU1, whole protein fractions were analyzed by Western blotting with anti-AU1 mAb. The levels of caspase-8 in each sample are shown in inset. A non-specific band is shown by a star.

Figure 10A:
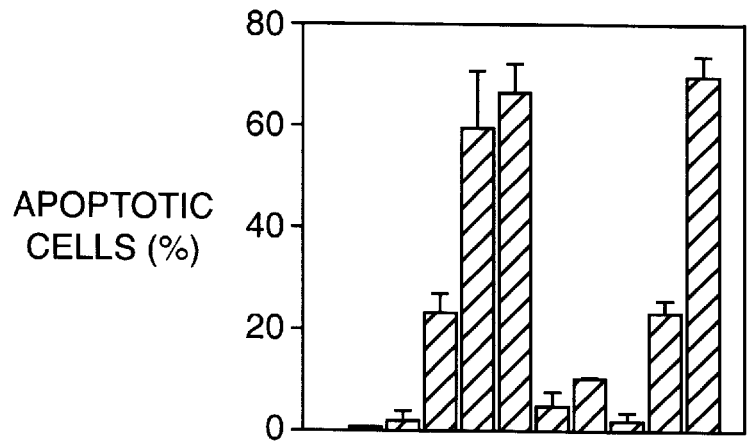
FIG. 10(A) shows the percentage of apoptotic cells in triplicate cultures of 293T cells that were transfected with vector control, RICK or Flag-RICK expression plasmids in the presence and absence of AU1 tagged caspase-8 or caspase-8-mt. caspase-10 or p35 expression plasmids were transfected as indicated in the lanes. zVAD-fmk was added as indicated in the lanes.
Figure 10B:
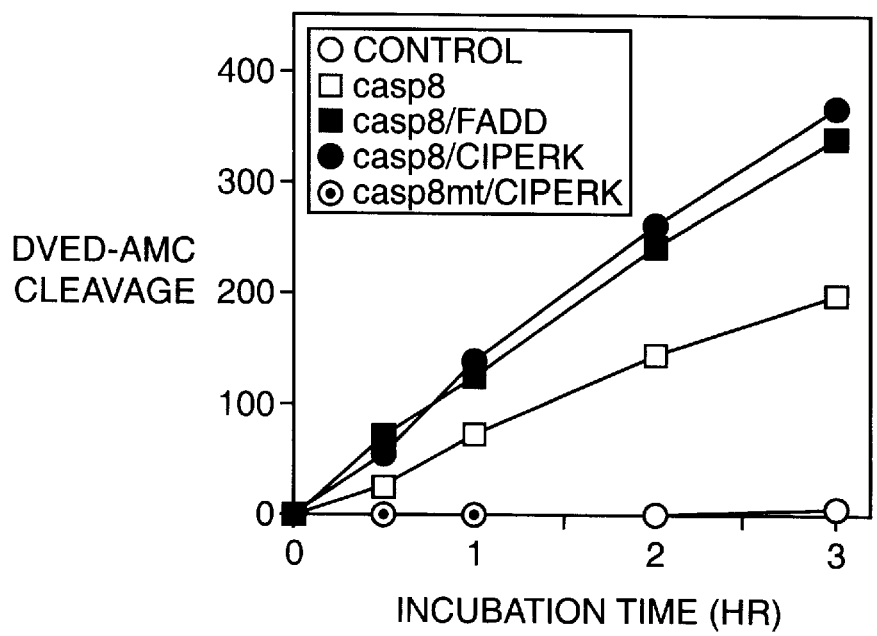
FIG. 10(B) shows RICK [CIPERK]facilitates the DEVD-AMC cleavage activity of caspase-8. 293T cells were co-transfected with vector control (○), pcDNA3-caspase-8-AU1-mt and pcDNA3-Flag-RICK (△), pcDNA3-caspase-8-AU1 alone (□), pcDNA3-caspase-8-AU1 and pcDNA3-FADD-myc (■) or pcDNA3-caspase-8-AU1 and pcDNA3-
Figure 10C:
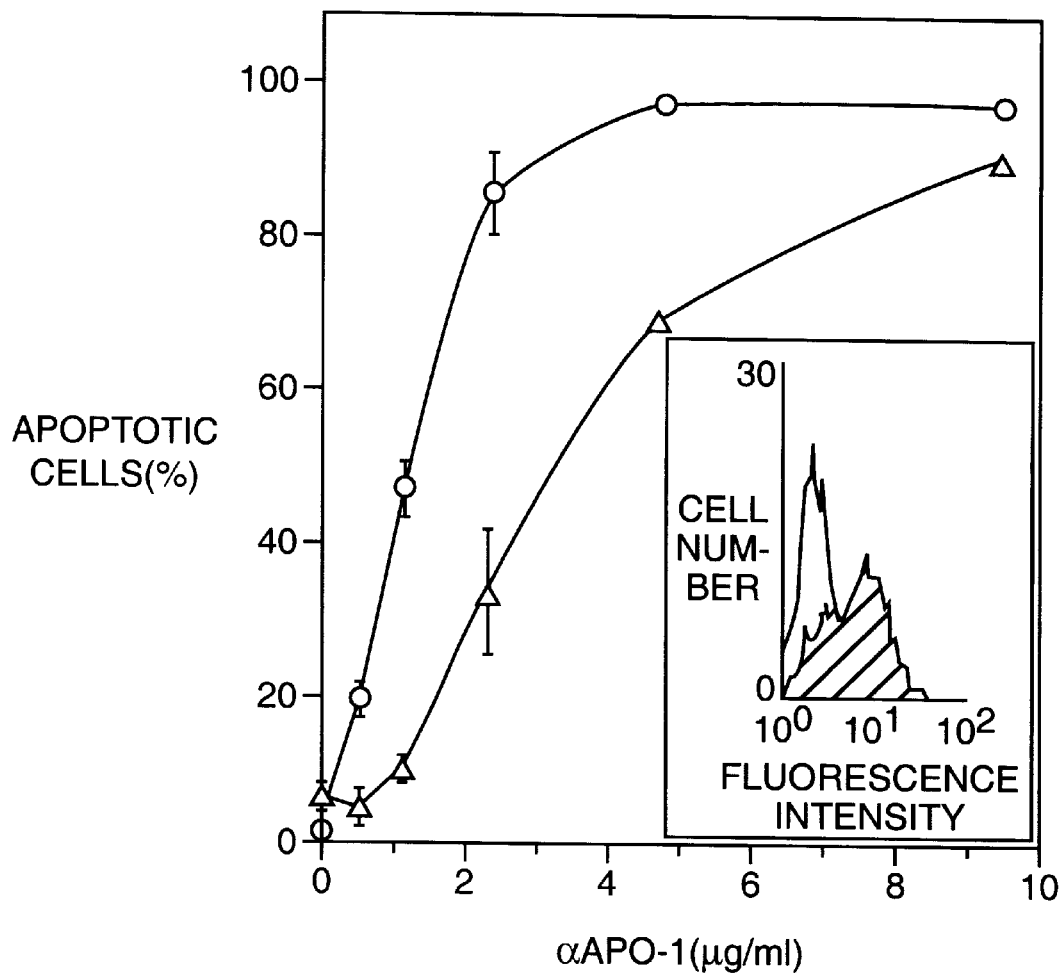
FIG. 10 shows the regulation of apoptosis by RICK.

FIG. 10(C) shows the inhibitory effect of mutant RICK on apoptosis induced by anti-CD95 antibody. BJAB cells stably expressing pcDNA3 (○) or pcDNA3-Flag-RICK K38M ($^\triangle$) were incubated with anti-CD95 antibody plus protein G or protein G alone at 37° C. The percent of apoptotic cells were determined by PI staining in triplicate cultures. The expression level of BJAB-Flag-RICK-K38M (closed profile) or control BJAB-pcDNA3 (open profile) stained with anti-Flag mAb as detected by flow cytometric analysis are shown (inset).

Figure 10D:
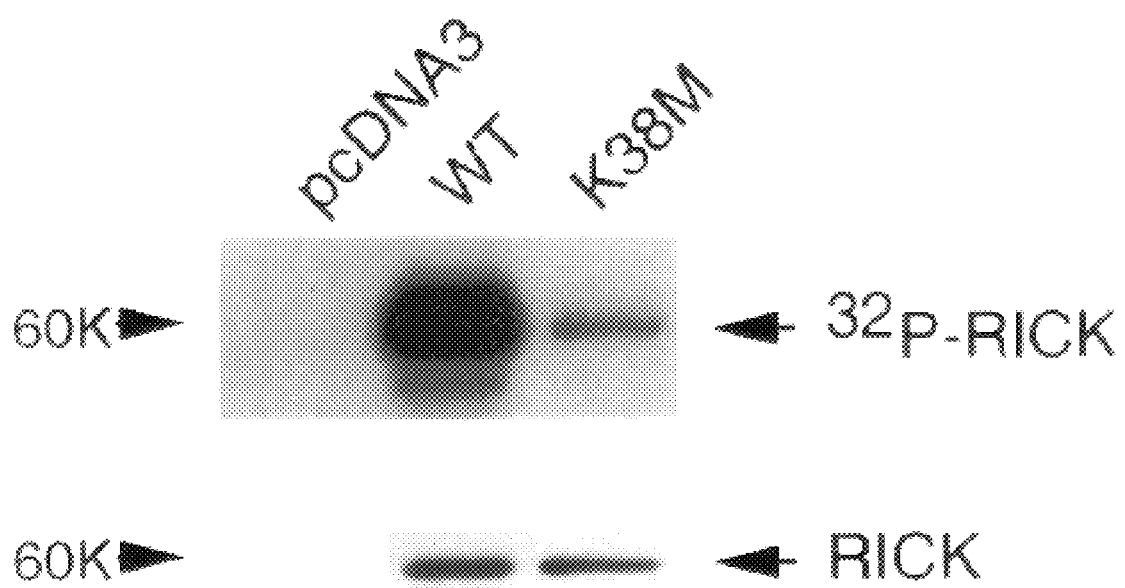

FIG. 10(D) shows RICK is a autophosphorylating kinase. 293T cells were transfected with pcDNA3, pcDNA3-Flag-RICK or pcDNA3-Flag-RICK-K38M. Flag-RICK proteins immunoprecipitated with mAb to Flag was incubated with [$\gamma$-$^{32}$P]ATP (upper panel). Total lysate was immunoblotted with mAb to Flag (lower panel).

FIG. 11 shows both Kinase and CARD domains of RICK are required for enhancement of apoptosis.

Figure 11A:
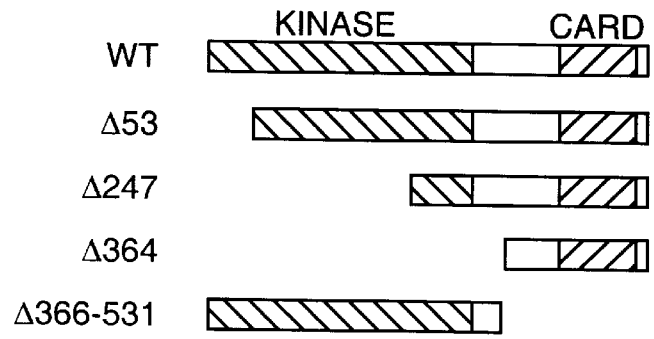

FIG. 11(A) is a schematic showing RICK and the deletion mutants of RICK. The kinase and CARD domains are indicated by closed and hatched boxes.

Figure 11B:
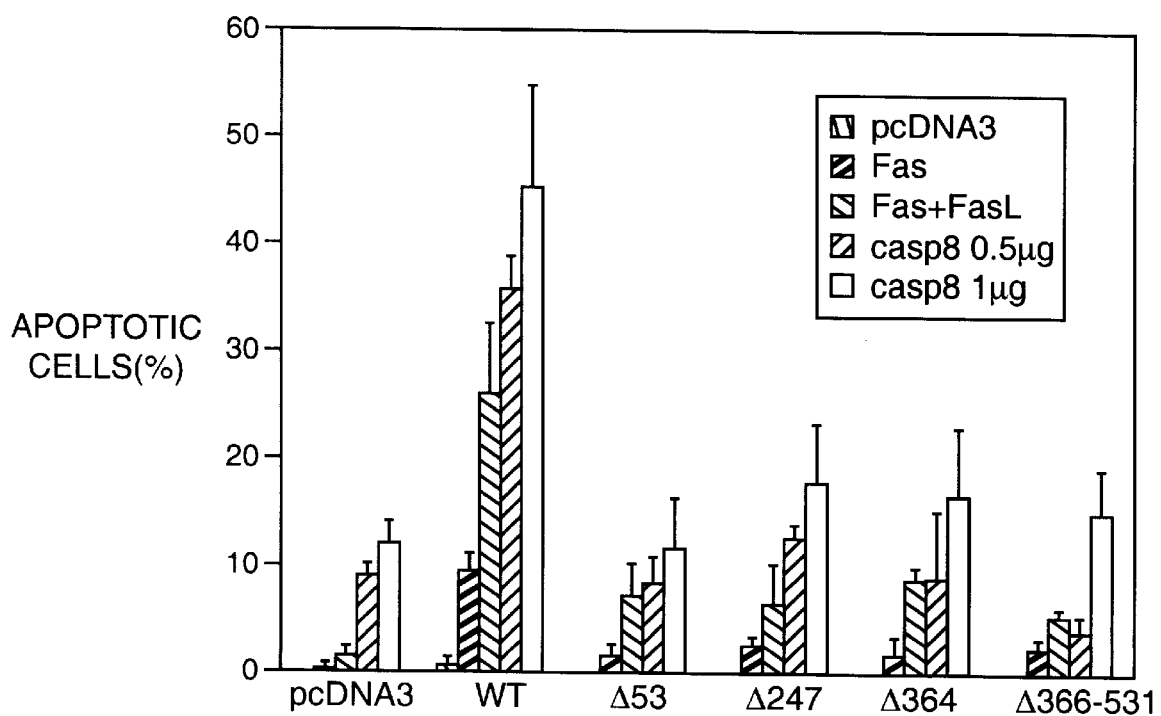

FIG. 11(B) shows both the kinase and CARD domains are required for RICK to enhance apoptosis. 293T cells were co-transfected with vector control, Flag-RICK or Flag-RICK mutant expression plasmids and indicated amounts of vector control, Fas or AU1 tagged caspase-8 and β-galactosidase expression plasmid. After 8 hours, recombinant FasL was added in indicated lanes, and the percentage of apoptotic cells was calculated.

Figure 11C:
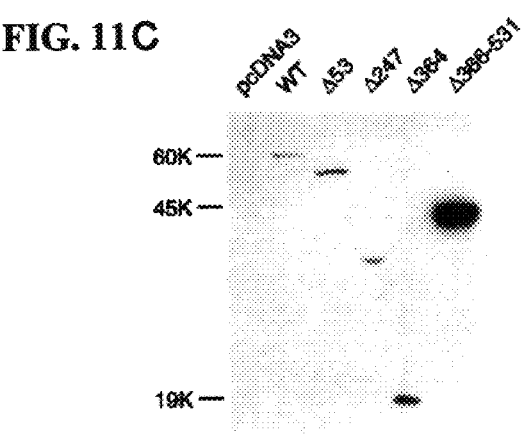

FIG. 11(C) shows the expression of wild-type (wt) and mutant RICK in 293T cells. Flag-tagged proteins from 293T cells expressing wt Flag-RICK, Flag-RICK-Δ53, -Δ247, -Δ364 and -Δ(366–531) were detected with rabbit polyclonal antibody to Flag. Tagged proteins are shown by arrow heads. Molecular size markers are shown in Da.

Figure 11D:
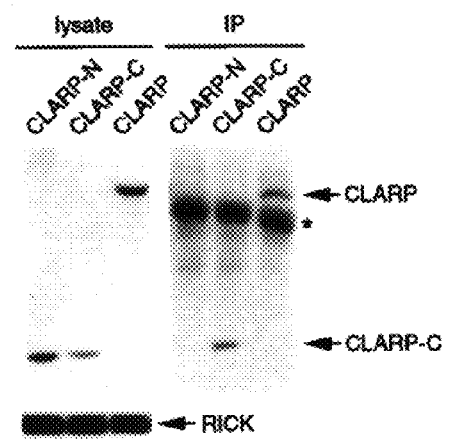

FIG. 11(D) shows binding of RICK to wt and mutant CLARP. 293T cells were co-transfected with plasmids producing Flag-tagged RICK and HA-tagged CLARP, CLARP-N or CLARP-C. Cell extracts were analyzed as in panel D. A background band (immunoglobulin heavy chain) is indicated by a star.

FIG. 12 shows phosphorylation of FADD by CIPERK or RICK. The nucleotide sequence which encodes human FADD is available as U24231, in GenBank.

Figure 12A:
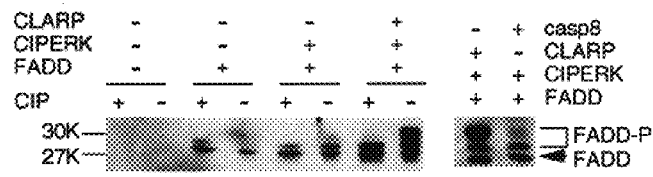

FIG. 12(A) shows lysates of 293T cells that were co-transfected with plasmids producing Flag-CIPERK, HA-CLARP, AU1-FADD (left panel) and AU1-caspase-8-mt (right panel), and were treated (+) with phosphatase (CIP) or left untreated (-). AU1-FADD was detected with mAb to AU1.

Figure 12B:
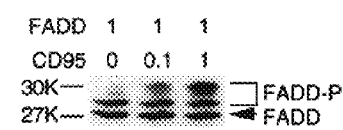

FIG. 12(B) is a representative immunoblot showing 293T cells that were cotransfected with plasmids expressing CD95 and AU1-FADD, and immunoblotted with mAb to AU1.

Figure 12C:
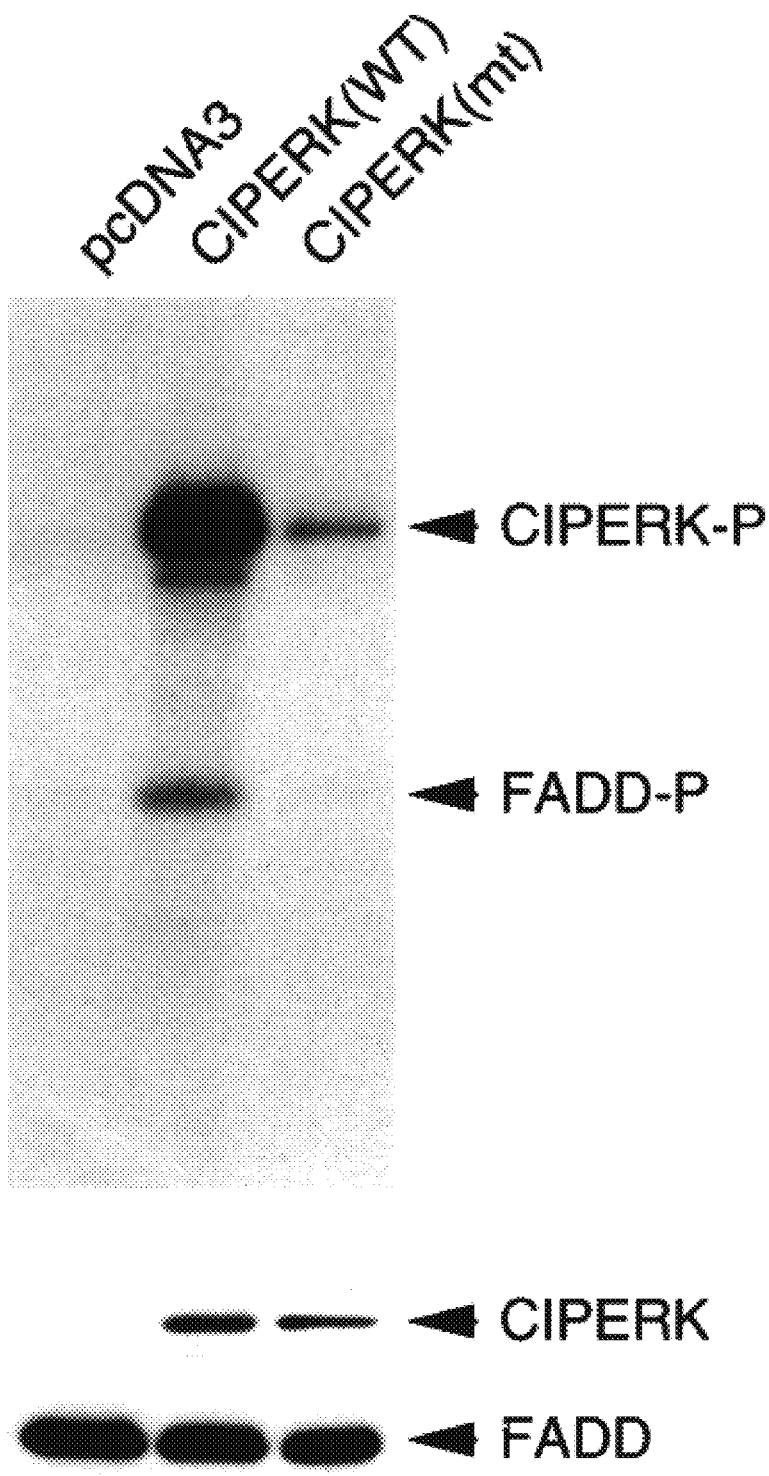

FIG. 12(C) shows phosphorylated FADD and CIPERK detected by X-ray film exposure (upper panel). CIPERK proteins in total lysate were detected by immunoblotting with mAb to Flag (middle panel). Recombinant FADD on the same filter used in (A) was detected by immunoblotting, with rabbit polyclonal anti-(His)$_6$ antibody (lower panel). Note CIPERK was autophosphorylated. The estimated molecular size is shown on the left [293T cells were transfected with vector control or plasmid expressing Flag-CIPERK (WT) or Flag-CIPERK-K38M (mt), and then CIPERK proteins were immunoprecipitated by mAb to Flag and incubated with recombinant FADD and 5 μM [$\gamma$-$^{32}$P] ATP].

Figure 12D:
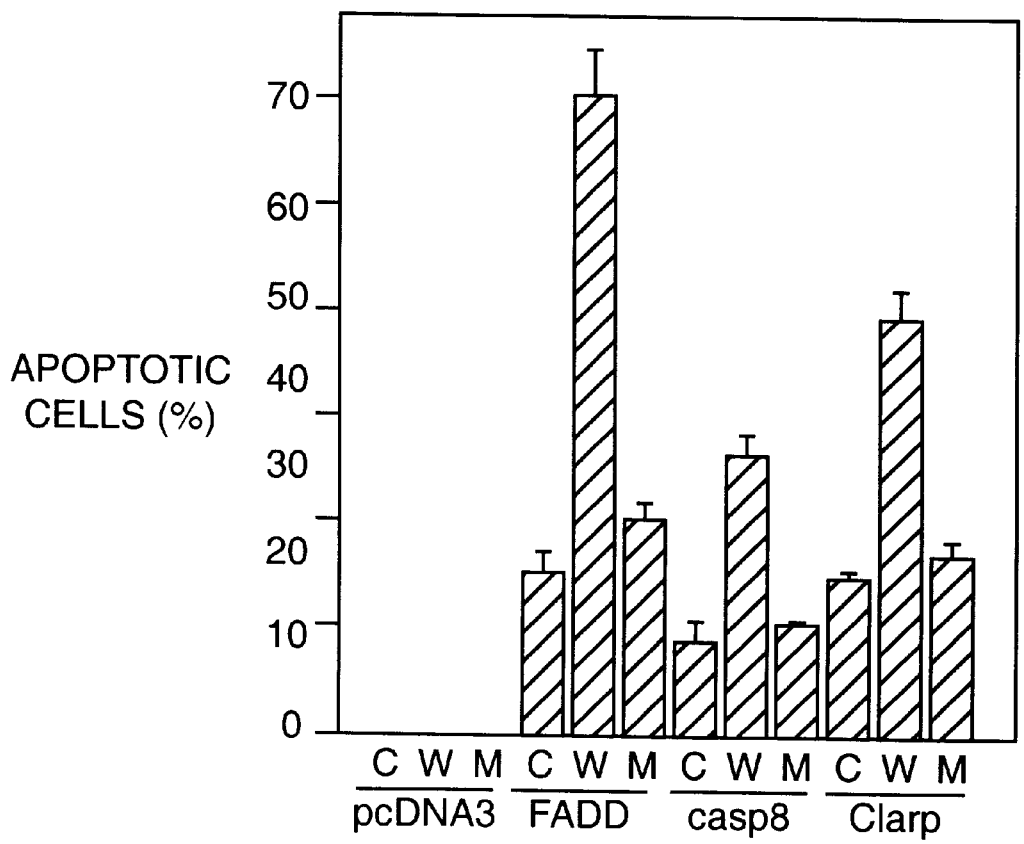

FIG. 12(D) shows the percent of apoptotic cells calculated in triplicate cultures of 293T cells. 293T cells were co-transfected with vector control (c), wt CIPERK (w) or mutant CIPERK-K38M (m) expression plasmid and control vector or plasmid expressing AU1-tagged caspase-8, myc-tagged FADD or HA-tagged CLARP.

Figure 13:
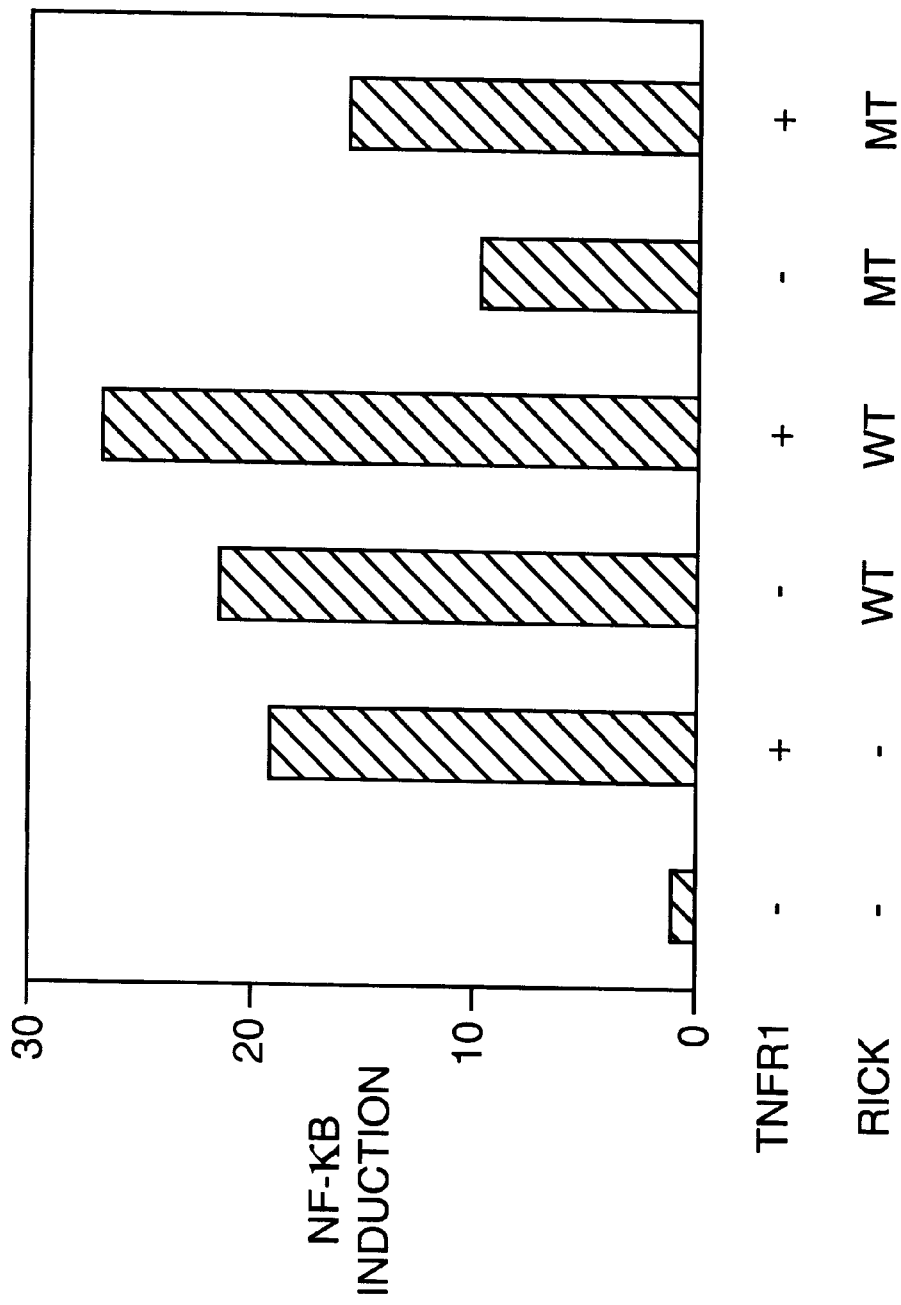

FIG. 13 shows RICK activates NF-KB in 293T cells.

FIG. 14 shows the nucleotide and amino acid sequences, schematic primary structures and alignments of Mouse CIDE-A, CIDE-B, FSP27, Human CIDE-A and *D. melanogaster* DREP-1.

Figures 14A, 14B:
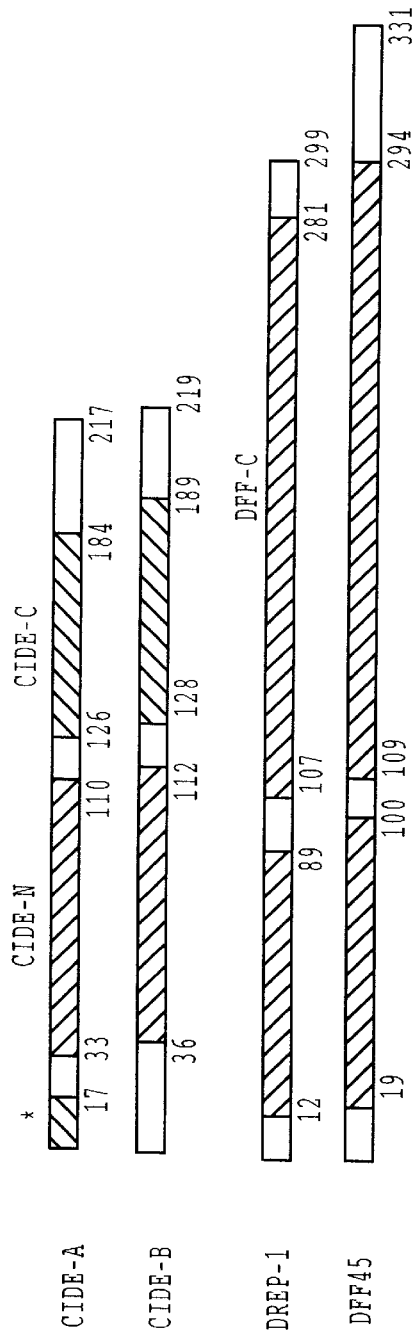

FIG. 14(A) shows the schematic structure of CIDE-A, CIDE-B, DREP-1, and DFF-45. CIDE-N, CIDE-C and DFF-C domains are shown as closed, light gray and dark gray boxes boxes, respectively. The region specific for CIDE-A* is shown as a hatched box.

FIG. 14(B) shows the amino acid sequence and alignments of N-terminal regions of CIDEs (SEQ ID NOS:12, 16 and 18), FSP27 (mouse), DREP-1 and DFF45.

FIG. 14(C) shows the amino acid sequence and alignments of carboxy-terminal regions of CIDEs (SEQ ID NOS:12, 16 and 18) and FSP27 (mouse).

FIG. 14(D) shows the amino acid sequence and alignments of carboxy-terminal regions of DREP-1 (SEQ ID NO:21) and DFF45 (SEQ ID NO:52). Proposed conserved blocks are overlined. The putative alternative initial codon of mCIDE-A was indicated by a star. Each entire sequence of mouse CIDE-A (SEQ ID NO:16), CIDE-B (SEQ ID NO:18), FSP27 (SEQ ID NO:31), human CIDE-A (SEQ ID NO:1), DFF45 (SEQ ID NO:32) and *D. melanogaster* DREP-1 (SEQ ID NO:21) was shown in Panels C and D. The nucleotide sequences which encode mouse CIDE-A (SEQ ID NO:16), CIDE-B (SEQ ID NO:18), FSP27 (SEQ ID NO:31), human CIDE-A (SEQ ID NO:12), DFF45 (SEQ ID NO:32) and DREP-1 (SEQ ID NO:21) are available as AF041376, AF041377, M61737, AF041378, U91985 and AF041375, respectively, in GenBank.

FIG. 14(E) shows the human CIDE-A cDNA sequence (SEQ ID NO:13).

FIG. 14(F) shows the human CIDE-A amino acid sequence (SEQ ID NO:12).

FIG. 14(G) shows the mouse CIDE-A cDNA sequence (SEQ ID NO:17).

FIG. 14(H) shows the mouse CIDE-A amino acid sequence (SEQ ID NO:16).

FIG. 14(I) shows the mouse CIDE-B cDNA sequence (SEQ ID NO:19).

FIG. 14(J) shows the mouse CIDE-B amino acid sequence (SEQ ID NO:18).

Figure 14K:
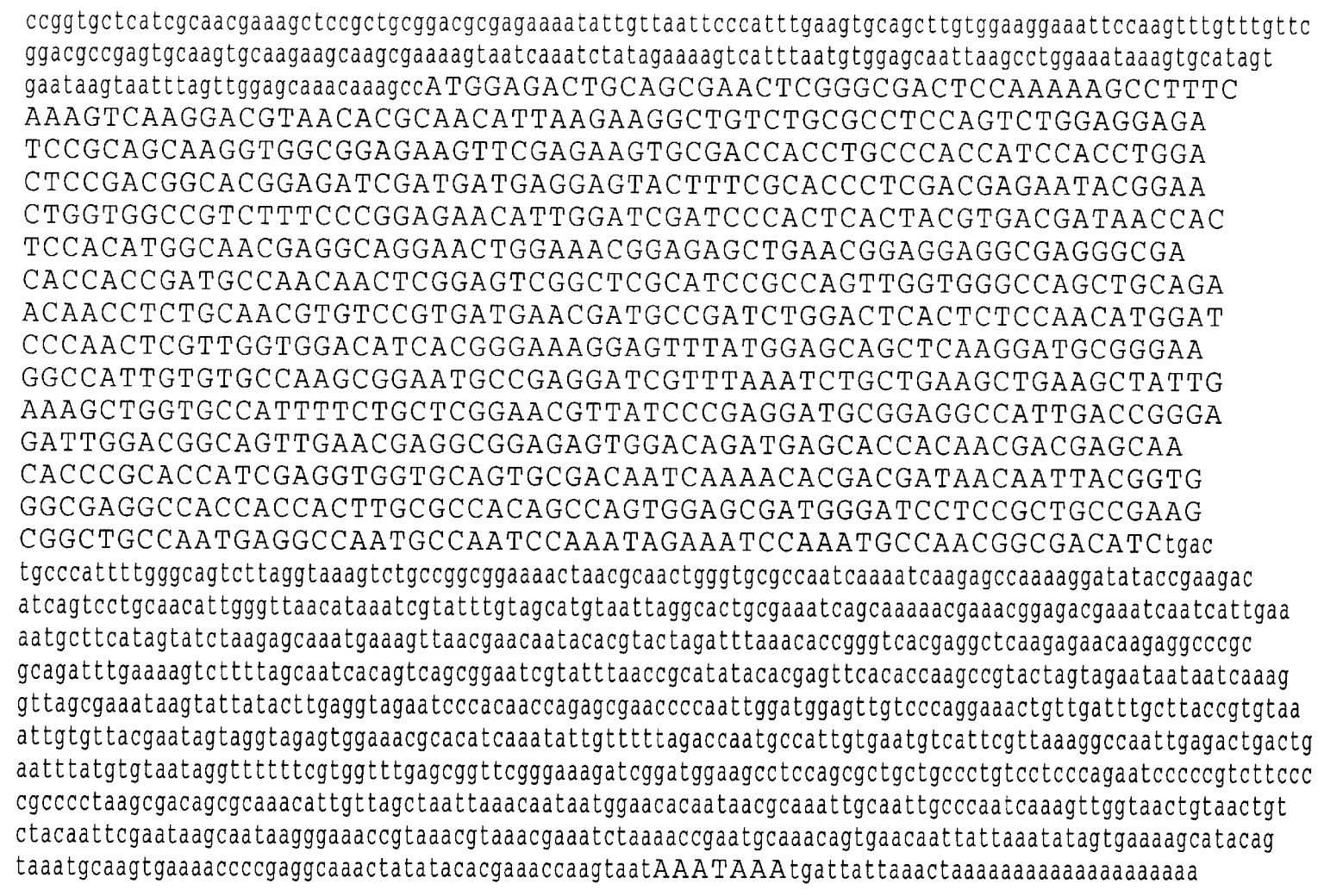

FIG. 14(K) shows the *D. melanogaster* DREP-1 cDNA sequence (SEQ ID NO:21).

FIG. 14(L) shows the *D. melanogaster* DREP-1 amino acid sequence (SEQ ID NO:20).

Figures 15A, 15B:
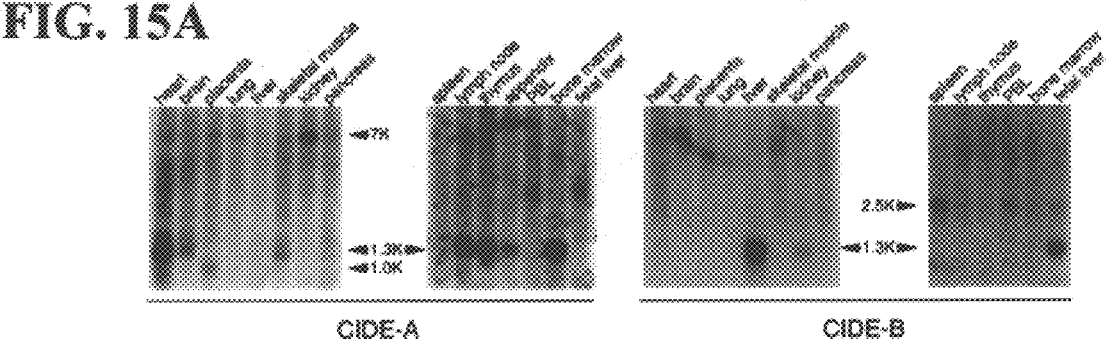

FIG. 15 is an autoradiograph showing the tissue distribution of the CIDE-A (FIG. 15A) and CIDE-B (FIG. 15B)

transcripts. Expression of CIDE-A and CIDE-B in human tissues were analyzed by Northern blot analysis. PBL denotes peripheral blood leukocytes.

FIG. 16 shows CIDEs induce apoptosis in mammalian cells.

Figure 16A:
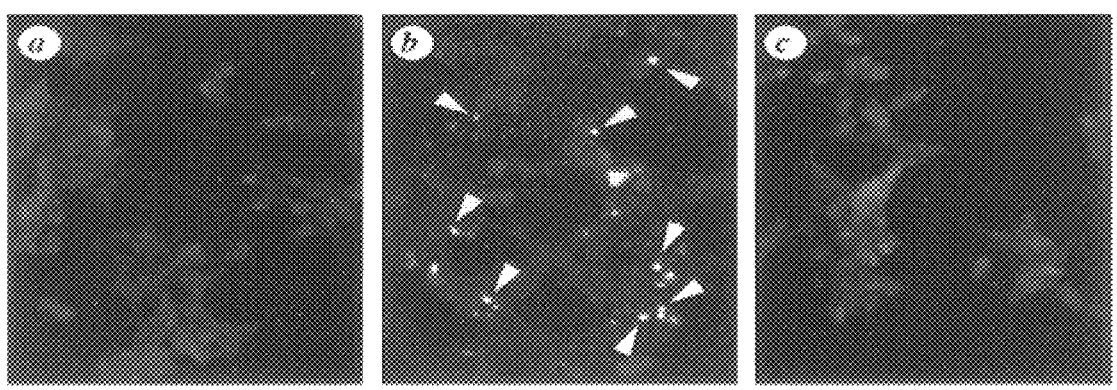

FIG. 16(A) shows ectopic expression of CIDE-A induces apoptosis of 293T cells. 293T cells were cotransfected with pcDNA3 (a), pcDNA3-Flag-CIDE-A (b), or pcDNA3-Flag-DFF45 (c), and the nuclei of transfected cells were stained. Magnification X 400.

Figure 16C:
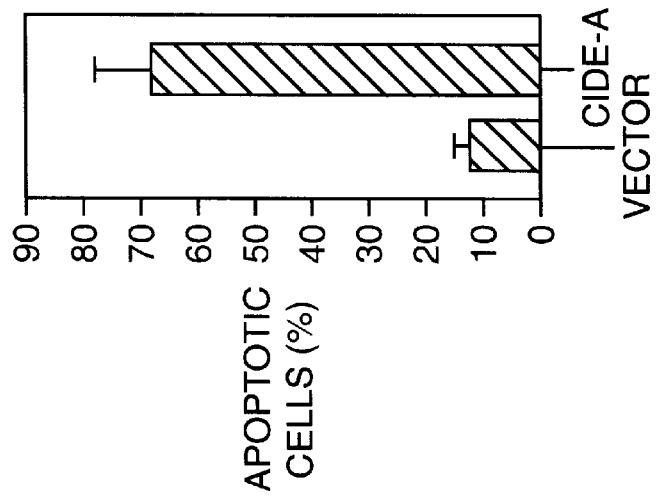
Figure 16B:
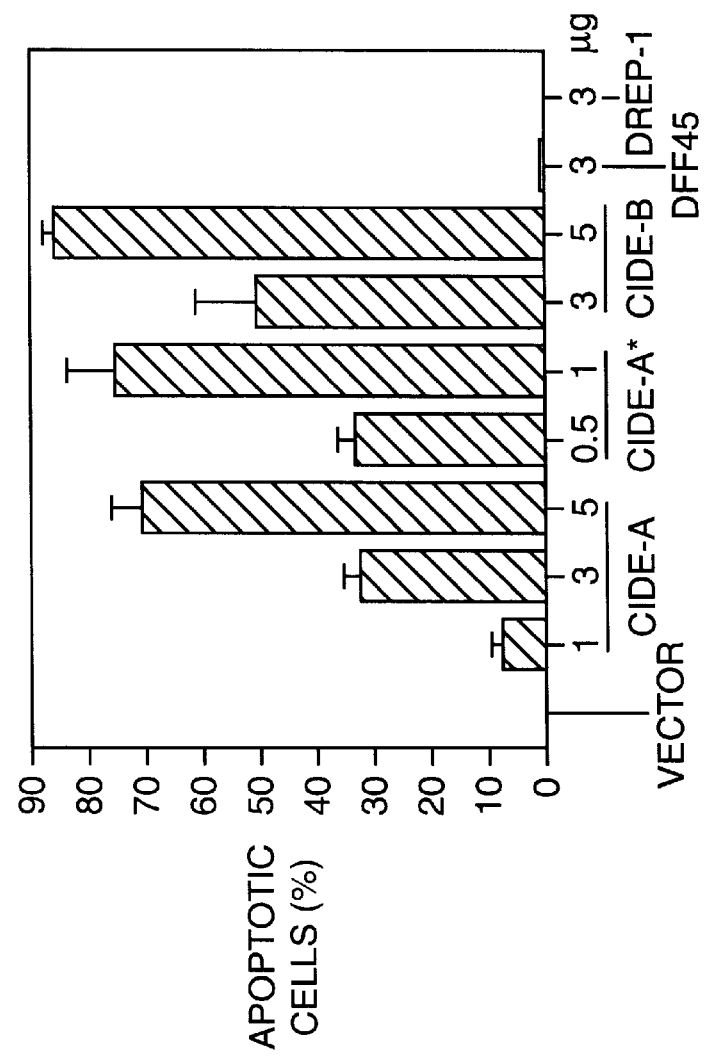

FIG. 16(B) shows apoptosis of 293T cells induced by CIDE-A and CIDE-B but not by DFF45 and DREP-1. The data (mean±SD) represent the percentage of round, apoptotic cells with membrane blebbing as a function of total -galactosidase-positive cells (n=3). 293T cells were cotransfected with indicated amount of expression plasmid of Flag-tagged CIDE-A, CIDE-A*, CIDE-B, DFF-45 or DREP-1 together with a β-galactosidase-expressing reporter construct.

FIG. 16(C) shows ectopic expression of CIDE-A induces apoptosis in MCF7 cells. MCF7 were cotransfected with pcDNA3 or pcDNA3-Flag-CIDE-A and β-galactosidase-expressing reporter construct. The percentage of apoptotic cells was determined as mentioned in Panel B.

FIG. 17 shows DFF-45/DREP-1 can inhibit apoptosis induced by CIDEs.

Figure 17A:
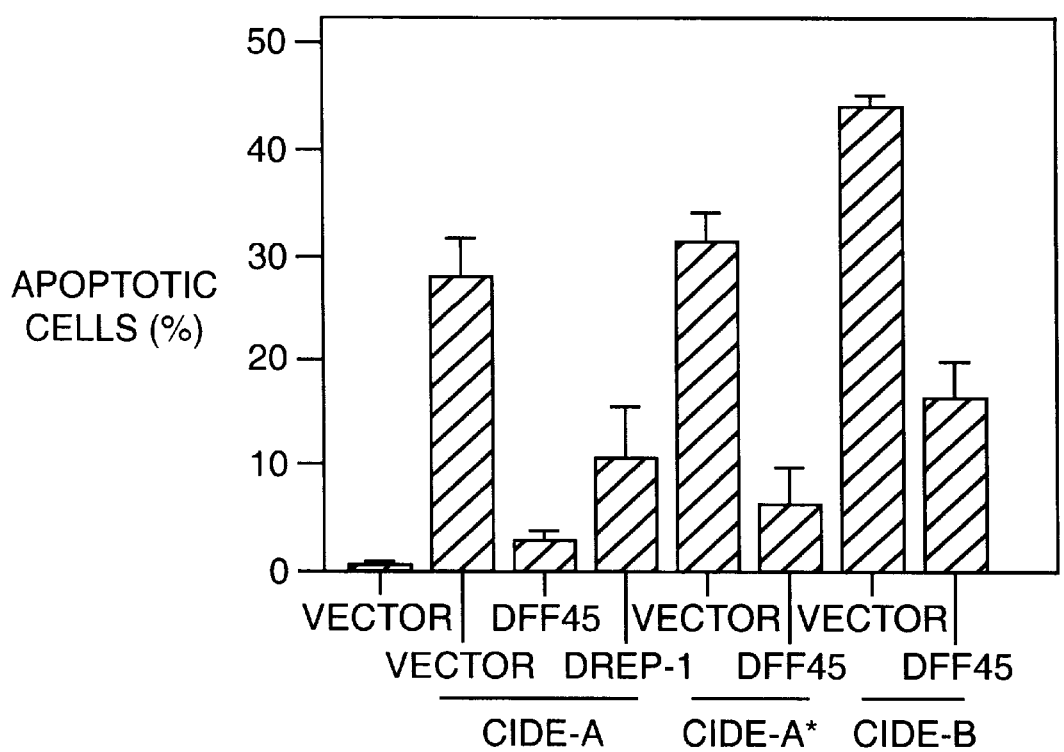

FIG. 17(A) shows DFF45 can block apoptosis induced by CIDE-A and CIDE-B. 293T cells were cotransfected with pcDNA3 vector alone, pcDNA3-Flag-CIDE-A, pcDNA3-Flag-CIDE-A* or pcDNA3-Flag-CIDE-B plus pcDNA3 or plus pcDNA3 or pcDNA3-Flag-DFF45, and the percent of apoptotic cells was determined.

Figure 17B:
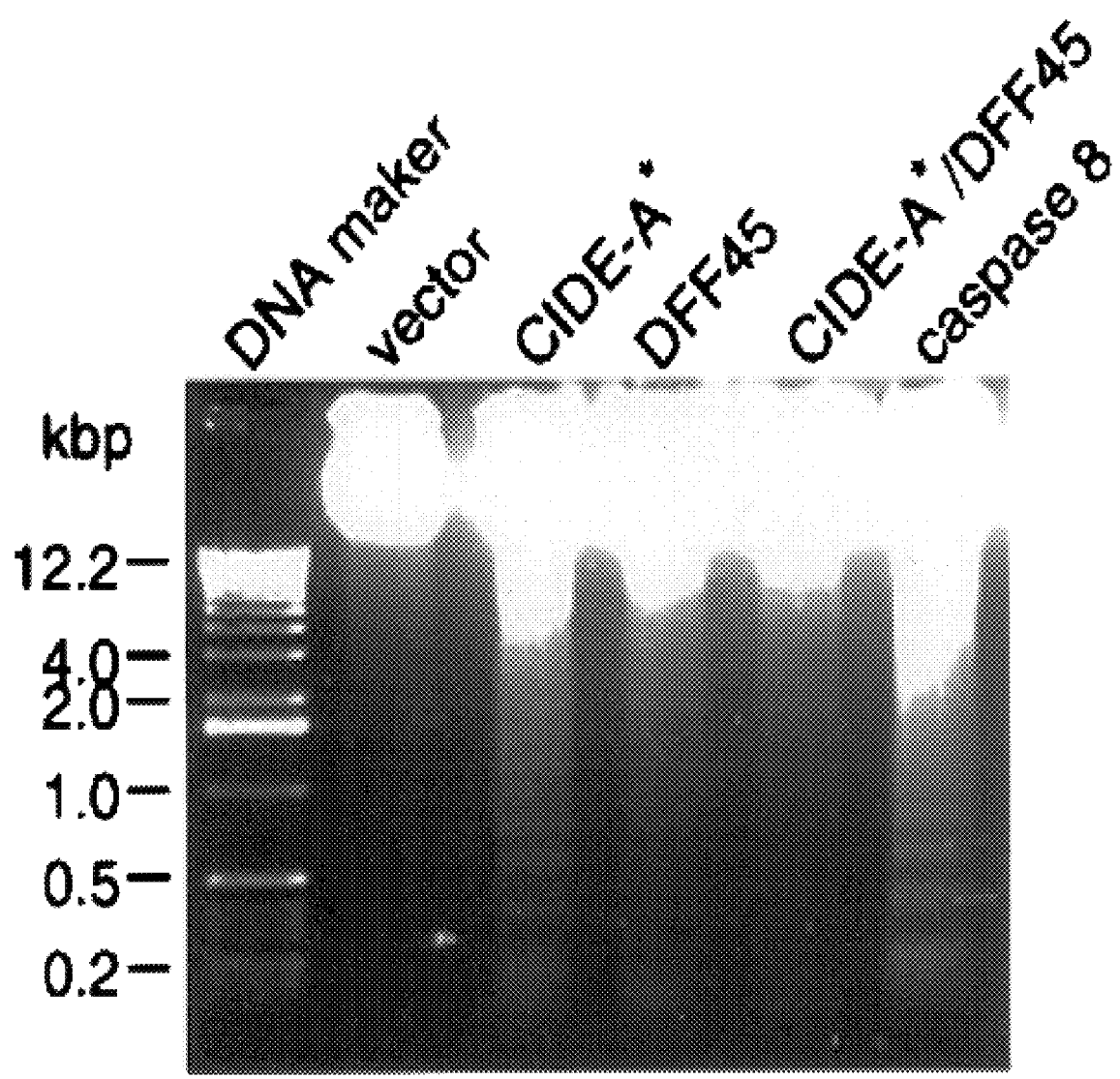

FIG. 17(B) shows DFF45 can inhibit DNA fragmentation induced by CIDE-A*. 293T cells were cotransfected with pcDNA3 vector alone or pcDNA3-Flag-CIDE-A*, pcDNA3-Flag-DFF45, pcDNA3-Flag-CIDE-A* plus pcDNA3-Flag-DFF45 or pcDNA3-caspase-8-AU1. The genomic DNA was extracted from cells and an aliquot loaded for agarose gel electrophoresis.

Figure 18B:
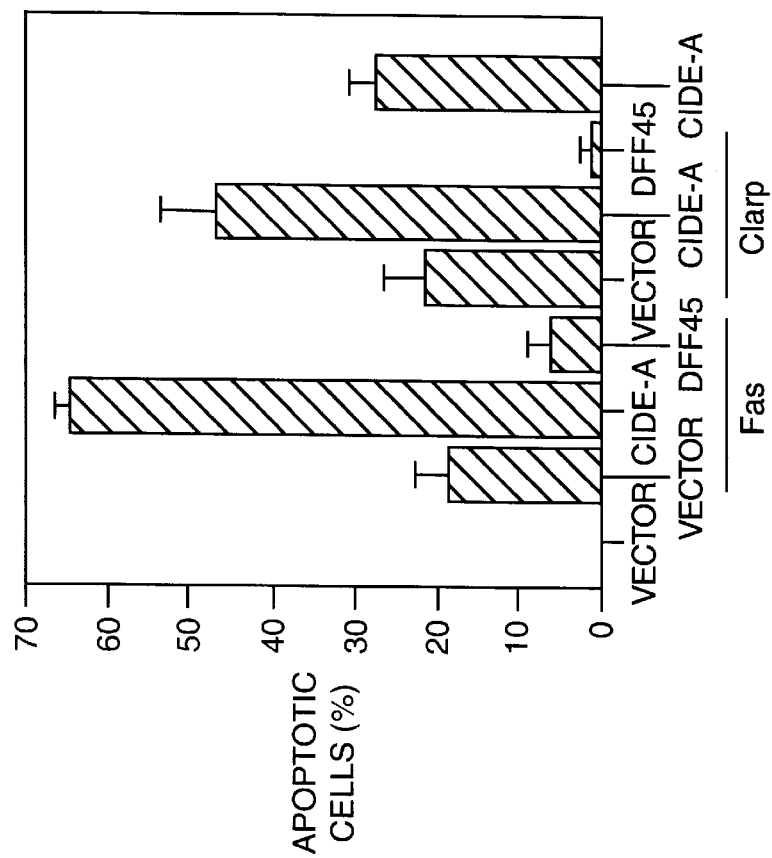
Figure 18A:
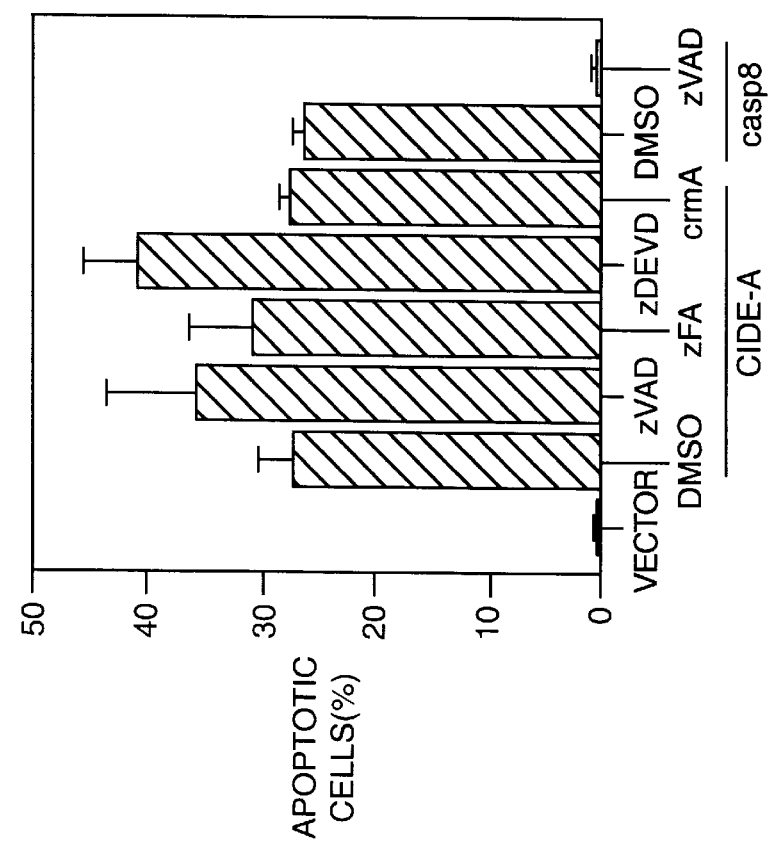

FIG. 18(A) shows caspase inhibitors cannot block CIDE-A-induced apoptosis. 293T cells were cotransfected with pcDNA3 vector alone, pcDNA3, pcDNA3-Flag-CIDE-A, pcDNA3-Flag-CIDE-A plus pcDNA3-crmA or pcDNA3-caspase-8-AU1. The caspase inhibitor, zVAD-fmk or zDEVD-fmk, or a control peptide, zFA-fmk dissolved in dimethylsulfoxide (DMSO) was added at 8 hrs post-transfection. No cell death was observed 8 hrs after transfection. Cell death assays were performed as mentioned for FIG. 16(B).

FIG. 18(B) shows Fas-, CLARP-Induced apoptosis is enhanced by CIDE-A and blocked by DFF45. 293T cells were cotransfected with CIDE-A or DFF-45 expression plasmids plus pcDNA3-Fas or pcDNA3-CLARP-HA, and Cell death assays were performed.

FIG. 19 shows the mutation analysis of CIDE-A.

Figure 19A:
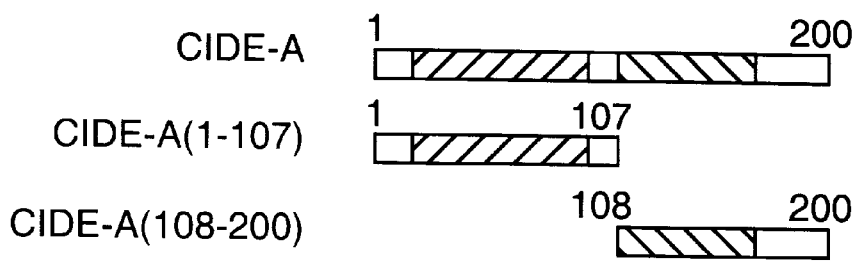

FIG. 19(A) is a schematic showing the CIDE-A mutants.

Figure 19B:
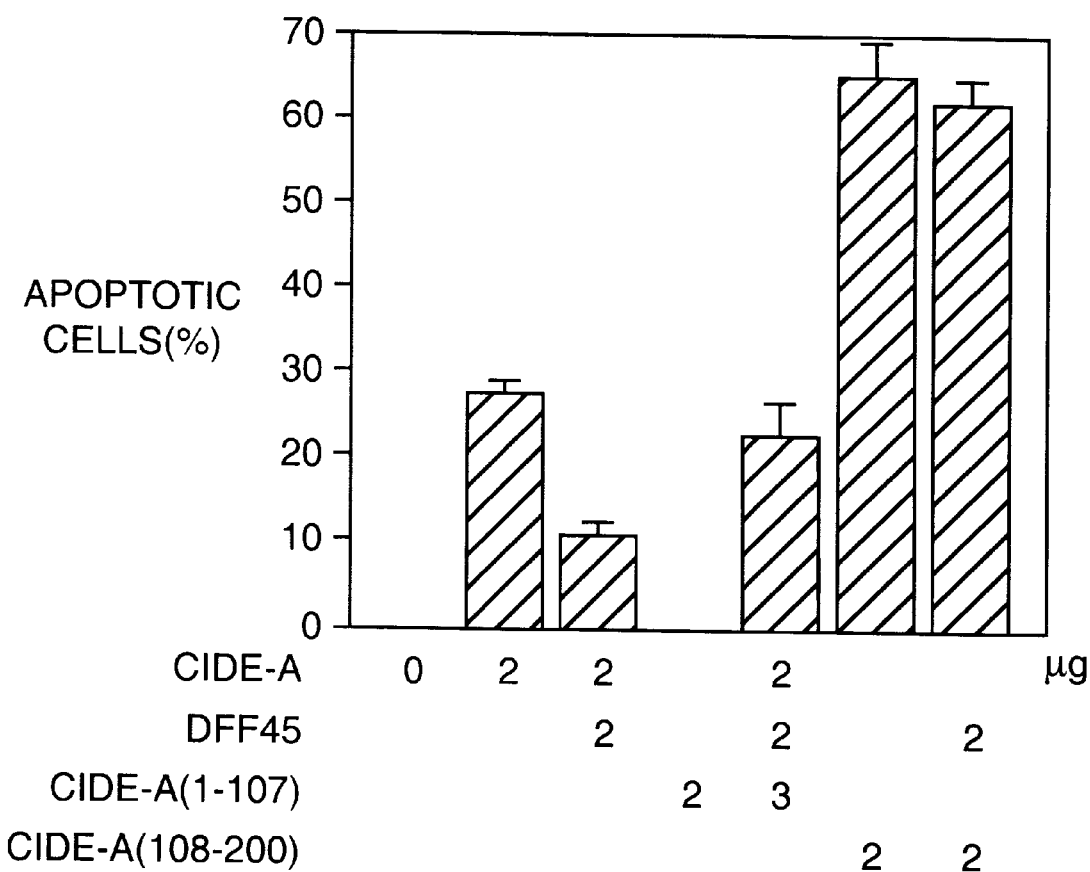

FIG. 19(B) shows the CIDE-C domain induced apoptosis but not CIDE-N, which is required for inhibition of CIDE-A-induced apoptosis by DFF-45. 293T cells were cotransfected with pcDNA3-Flag-CIDE-A, pcDNA3-Flag-CIDE-A (1–107), pcDNA3-Flag-CIDE-A (108–200), pcDNA3-Flag-DFF45 or vector control. 24 hr post-transfection, Flag-tagged proteins were detected with monoclonal anti-Flag antibody. Cell death assays were performed as described in the methodology.

Figure 19C:
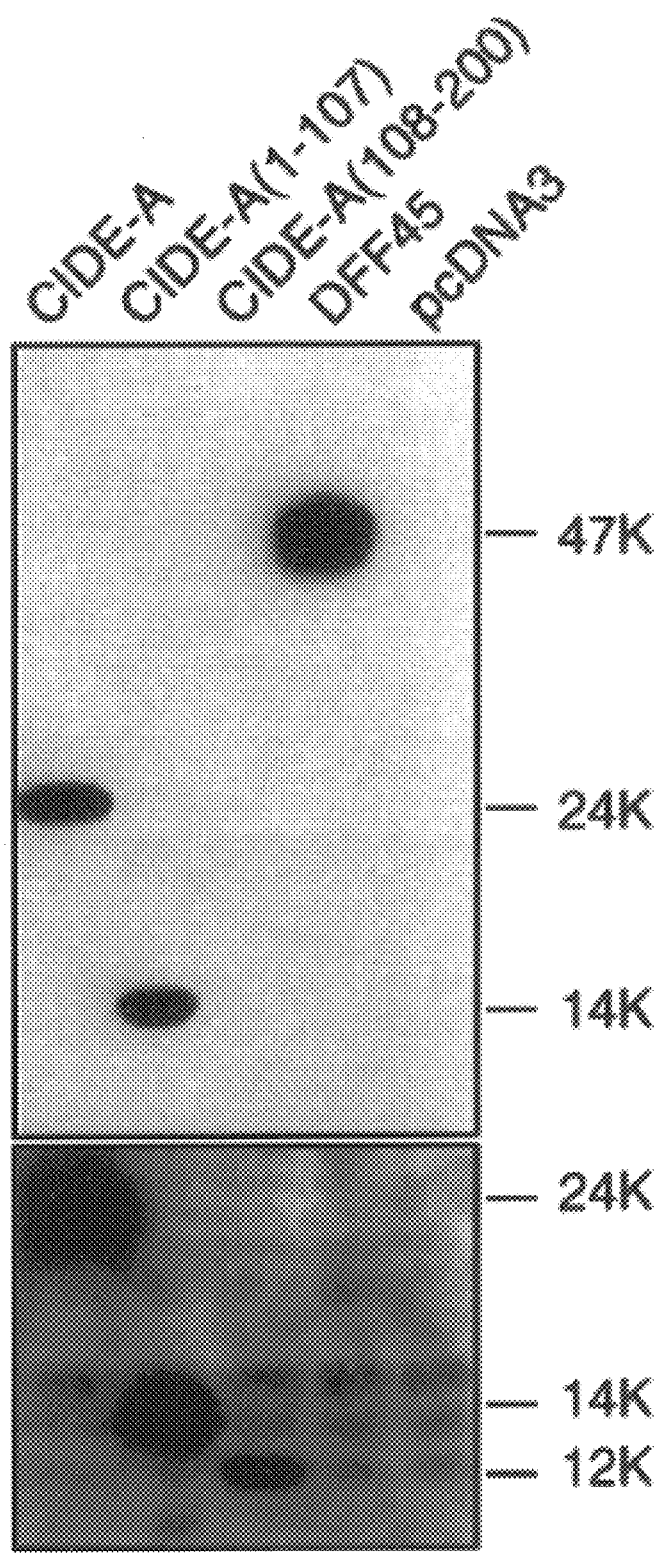

FIG. 19(C) shows the expression of CIDE-A, its mutants and DFF45. 293T cells were transfected as above and lyzed with NP-40 buffer, 24 hr post-transfection. Tagged proteins were detected with ECL-kit with X-ray film. 10 sec. exposed and 30 min-exposed images are as shown in upper and lower panels, respectively.

FIG. 20 shows the human and mouse CIPER cDNA and amino acid sequences.

FIG. 20(A) shows the human CIPER CDNA sequence (SEQ ID NO:35).

FIG. 20(B) shows the human CIPER amino acid sequence (SEQ ID NO:36).

FIG. 20(C) shows the mouse CIPER CDNA sequence (SEQ ID NO:37).

FIG. 20(D) shows the mouse CIPER amino acid sequence (SEQ ID NO:38).

FIG. 21 shows the human CLARP cDNA (SEQ ID NO:33) and amino acid sequences (SEQ ID NO:34). The nucleotide sequences which encodes human CLARP is available as AF005774, in GenBank.

FIG. 21(A) shows the human CLARP cDNA sequence (SEQ ID NO:33).

FIG. 21(B) shows the human CLARP amino acid sequence (SEQ ID NO:34).

DEFINITIONS

To facilitate understanding of the invention, a number of terms are defined below.

The abbreviations used herein are: ARC, Apoptosis Repressor with CARD domain; FADD, Fas-associated death domain protein; TNFR, Tumor necrosis pathway receptor, TRADD, TNFR-associated death domain protein; DFF, DNA fragmentation factor; DFF45, 45 kDa subunit of the DNA fragmentation factor [also known as ICAD]; DFF45, 40 kDa subunit of the DNA fragmentation factor [also known as CAD]; CAD, Caspase-activated DNase; ICAD, inhibitor of Caspase-activated DNase; CIDE, Cell Death Inducing DFF45-like effector; DREP-1, a *Drosophila melanogaster* homologue of DFF45; RICK, RIP-like interacting CLARP kinase [RICK is also referred to as CIPERK] CARD, caspase recruitment domain; CLARP, caspase-like protein with homology to caspase-8; CED-3, *Caenorrhabditis elegans* CED-4 and its mammalian homologue, Apaf-1; RICK-K38M, RICK ATP-binding site mutant.

The term "apoptosis" means non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The present invention contemplates oligonucleotides which will hybridize to protein of nucleic acid encoding RICK, ARC and CIDE. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane [Marmur and Lane, *Proc. Natl. Acad. Sci. USA* 46:453 (1960)] and Doty et al.[Doty et al., *Proc. Natl. Acad. Sci. USA* 46:461 (1960)] have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. [Wallace et al., *Biochimie* 67:755 (1985)]. In the case of radioactive oligonucleotide probes, only extremely high specific activities are found to show satisfactory results. [Studencki and Wallace, *DNA* 3:1 (1984); Studencki et al., *Human Genetics* 37:42 (1985)].

K. B. Mullis et al, U.S. Pat. Nos. 4,683,195 and 4,683, 202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. There can be numerous "cycles" to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "Polymerase Chain Reaction" (hereinafter PCR). Because the desired amplified segments of the target sequence become the predominant sequences (in terms of concentration) in the mixture, they are said to be "PCR amplified".

The present invention specifically contemplates using primers capable of hybridizing to a portion of the nucleic acid sequences encoding RICK, ARC and CIDE in a PCR reaction to identify homologues, as well as the orthologue gene in other species. Such primers are preferably less than fifty nucleotides in length (although longer primers can be used if desired).

The present invention also contemplates using probes capable of hybridizing to a portion of the nucleic acid sequences encoding RICK, ARC and CIDE. The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g., Green Fluorescent Protein (GFP).

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. Pat. No. 5,652,096, hereby incorporated by reference.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Perason and Lipman [Pearson and Lipman, Proc. Natl. Acad. Sci. (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (ARC, RICK, CIDE-A, CIDE-B, DREP-1)

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions(claimed in the present invention) with its various ligands and/or substrates.

The term "analog" as used herein refers to polypeptides which are comprised of a segment of at least 25 amino acids that has substantial identity to a portion of the deduced amino acid sequence of ARC, RICK, CIDE-A, CIDE-B or DREP-1. The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as positive or negative modulators of apoptosis by inclusion in screening assays described herein below.

GENERAL DESCRIPTION OF THE INVENTION

The invention generally relates to suitable methods and compositions for the identification of compounds that activate, inhibit and/or regulate the apoptotic signaling pathway, including identification of compounds that have therapeutic utility where cell growth or proliferation is aberrant, for example, as anti-neoplastic agents. The Description of the Invention involves: A) The Apoptosis Signaling Pathway; and B) Inhibitors and Activators of the Apoptosis Pathway.

A. The Apoptosis Signaling Pathway

Caspases: The apoptotic mechanism is controlled by a evolutionarily conserved genetic program which is activated in the dying cell [See Review by Rudin and Thompson, *Ann. Rev. Med.* 48:267–281 (1997)]. Several regulatory components of the apoptotic pathway have been identified in various living organisms including man [See Review by Rudin and Thompson, *Ann. Rev. Med.* 48:267–281 (1997)]. In mammals, a family of cysteine proteases (designated caspases) related to the *C. elegans* CED-3 protein appears to represent a major effector arm of the apoptotic program [V. Kidd, "Proteolytic Activities That Mediate Apoptosis," *Ann. Rev. Physiol.* 60:533–573 (1998)]. Caspase activation is induced by a wide array of death signals and leads to cleavage of target proteins and execution of the apoptotic program. To date, more than ten caspases have been identified and partially characterized. Several of these caspases, notably caspase-2, -3, -4, -6, -7, -8, -9 and -10 have been implicated in the induction of apoptosis. The caspases are synthesized as inactive precursors that are proteolytically processed to generate active subunits. Each caspase contains conserved sequences important for proteolytic activity cleaving after specific aspartic acid residues. The mammalian cell death proteases have been divided into proximal and distal caspases based on their sites of action in the proteolytic caspase cascade [G. M. Cohen, "Caspases: The Executioners of Apoptosis," *Biochem. J.* 326(6):1–16 (1997)]. Activation of apical caspases, such as caspase-8, through cell death receptors or other apoptotic stimuli leads to activation of downstream caspases, precipitous cleavage of target proteins and execution of the apoptotic program [M. P. Boldin el al., *Cell* 85:803–815 (1996)].

Little is known about the regulation of caspase activity during apoptosis. In the nematode *C. elegans*, activation of the cell death protease CED-3 is positively regulated by CED-4 and inhibited by CED-9, the homologue of Bcl-2 and Bcl-$X_L$, through direct protein-protein interactions [D. Wu et al., *J. Biol. Chem.* 272:21449–21454 (1997)]. Likewise, Apaf-1, a human protein that resembles *C. elegans* CED-4 interacts with caspase-9, a step that is required for the activation of the downstream protease caspase-3 [H. Zou et al., *Cell* 90:405–413 (1997)]. The prodomains of several apical caspases contain a protein module termed caspase recruitment domain (CARD) that is conserved in several apoptosis regulatory molecules including Apaf-1, RAIDD and cellular IAPs. The CARD has been proposed to play a regulatory role in apoptosis by allowing proteins such as Apaf-1 to associate with caspase-9 [P. Li et al., *Cell* 91:479–489 (1997)]. Two viral proteins, baculovirus p35 and cowpox virus CrmA inhibit apoptosis by directly targeting caspases [Q. Zhou et al., *J. Biol. Chem.* 272:7797–7800 (1997)]. The inhibitors of apoptosis proteins (IAP) comprise a family of apoptosis inhibitors found in baculoviruses, Drosophila and mammals [C. S. Duckett et al., *EMBO J.* 15:2695–2694 (1996)]. Mammalian IAP-1, -2 and XIAP directly bind and inhibit enzymatically active death proteases, caspase-3 and caspase-7, but not the upstream protease caspase-8 [Q. L. Devereaux et al., *Nature* 388:300–304 (1997)]. The present invention identifies and characterizes a human cDNA encoding a protein designated ARC, that functions as an inhibitor of apoptosis. The inhibitory effect of ARC is selective in that it repressed apoptosis induced by caspase-8 and *C. elegans* CED-3, but not that mediated by caspase-9. ARC inhibited apoptosis mediated by stimulation of death receptors such as CD95/Fas, TNFR1 and TRAMP, as well as that activated by FADD and TRADD, two signaling molecules of the CD95/Fas and TNFR1 pathways whose expression can activate apoptosis. Because these death receptors as well as FADD and TRADD mediate their apoptotic effect through the activation of the apical proteases caspase-8 and/or caspase-2 [A. M. Chinnaiyan et al., *Cell* 81:505–512 (1995); H. Hsu et al., *Cell* 19:495–504 (1995); A. M. Chinnaiyan et al., *J. Biol. Chem.* 271:4961–4965 (1996)]., ARC is likely to regulate death receptor-induced apoptosis via its interactions with caspase-2 and caspase-8.

While the usefulness of the present invention does not depend on the understanding of a precise mechanism, it is believed that there are at least two possible models that could explain the apoptosis inhibitory function of ARC. First, ARC might repress apoptosis by inhibiting caspase activation through direct binding to death proteases. ARC could act by inhibiting the processing of immature caspases and/or direct inhibition of the active caspase subunits. The observation that ARC did not interact with the C-terminal region that contains the catalytic domains of caspase-8 suggests that ARC acts by targeting the immature caspase form. Cleavage of ARC was not observed when interacting with caspases, implying a mechanism different from that of the baculovirus p35 protein [N.J. Bump et al., *Science* 269:1885–1888 (1995)]. Second, ARC could inhibit apoptosis by disrupting the association between death proteases and their activators such as FADD or RAIDD. A similar mechanism has been proposed for FLIP proteins, a caspase-related molecule that like ARC interacts with caspase-8 [M. Irmler et al., *Nature* 388:190–195 (1997)]. The interaction between ARC and caspases appear to be mediated via the corresponding CARD or the structurally-related DED domains. Thus, ARC associated with caspase-2, caspase-8 and CED-3 but not with caspase-3, a death protease that lacks such a domain [G. M. Cohen, *Biochem J.* 326:1–16 (1997)]. Furthermore, mutant analysis of caspase-8 showed that the N-terminal region containing DEDs was required for its interaction with ARC. However, ARC did not interact with CARD-containing caspase-1 or caspase-9. Significantly, RAIDD has been reported to bind caspase-2 but not caspase-1 [H. Duan and V. M. Dixit, *Nature* 385:86–89 (1977)] although both caspases have CARD domains.

The expression of ARC was highly restricted to skeletal muscle and heart suggesting that ARC plays a role in the regulation of apoptosis in muscle tissues. Striated myofibers in skeletal muscle and heart are long lived cells. However, little is known about the mechanisms that inhibit apoptosis in muscle cells and are responsible for their long-term survival. Bcl-2 and Bcl-XL, two members of the Bcl-2 family, promote survival but they are expressed at low or undetectable levels in skeletal muscle [R. Matsuda et al., *J. Biochem.* 118:959–964 (1995)]. Thus, ARC expression may play a role in maintaining myofiber survival in skeletal muscle and heart tissues. Several inherited diseases including muscular dystrophy and spinal muscle atrophy are characterized by degeneration of muscle fibers through apoptosis and necrosis [Rudin and Thompson, *Ann. Rev. Med.* 48:267–281 (1997)]. Furthermore, dystrophic muscle of the mdx mouse and BIO14.6 hamster undergo apoptosis, degeneration and subsequently necrosis as disease progresses [R. Matsuda et al., *J. Biochem.* 118:959–964 (1995)]. Similarly, acquired conditions such as inflammatory myopathies, myocardial infarction and overload-induced myopathy have been shown to have a component of apoptotic cell death [S. Bialik et al., *J. Clin. Invest.* 100:1363–1372 (1977); E. Teiger et al., *J. Clin. Invest.* 97:2891–2897 (1996)]. It is apparent therefore that ARC could regulate apoptosis associated with these muscle cell diseases. In addition, the identification of ARC in the present invention, lays the foundation for the development of novel therapeutic approaches, including those that involve direct delivery of ARC to the areas of insult via gene therapy or through drugs capable of enhancing the activity or expression of endogenous ARC.

DNA fragmentation: To date, the downstream events that follow caspase activation leading to DNA fragmentation are still poorly understood. Several intracellular substrates including poly(ADP-ribose) polymerase [D. W. Nicholson et al., "Identification and inhibition of the ICE/CED-3 protease necessary for mammalian apoptosis," *Nature* 376:37–43 (1995)], sterol-regulatory element-binding proteins (SREBPs) [X. Wang et al., "Purification of an interleukin-1 beta converting enzyme-related cysteine protease that cleaves sterol regulatory element-binding proteins between the leucine zipper and transmembrane domains.," *J. Biol. Chem.* 270(30):18044–18050 (1995)], the U1-associated 70 kDa protein, the DNA-dependent protein kinase [L. A. Casciola-Rosen et al., "Specific cleavage of the 70-kDa protein component of the U1 small nuclear ribonucleoprotein is a characteristic biochemical feature of apoptotic cell death," *J. Biol. Chem.* 269:30757–30760 (1994); Q. Song et al., "DNA-dependent protein kinase catalytic subunit: a target for an ICE-like protease in apoptosis," *EMBO J.* 15:3238–3246 (1996)] and the retinoblastoma B protein (RB) [B. An and Q. P. Dou, "Cleavage of retinoblastoma protein during apoptosis: an interleukin 1 beta-converting enzyme-like protease as candidate," *Cancer Res.* 56:438–442 (1996) are cleaved by activated caspases. However, it is unclear whether the cleavage of any of these proteins plays a pivotal role in the induction of apoptosis. Recently, a heterodimeric protein, designated DNA fragmentation factor (DFF) that mediates DNA fragmentation of isolated nuclei has been purified through cellular fractionation experiments [X. Liu et al., "Apaf-1, a human protein homologous to *C. elegans* CED-4, participates in cytochrome c-dependent activation of caspase-3," *Cell* 90:405–413 (1997)]. DFF is composed of 45 and 40 kDa subunits, of which only the cDNA encoding the 45 kDa subunit has been cloned [X. Liu et al., "Apaf-1, a human protein homologous to *C. elegans* CED-4, participates in cytochrome c-dependent activation of caspase-3," *Cell* 90:405–413 (1997)]. DFF45, but not DFF40, is cleaved by active caspase-3 into three proteolytic fragments, a step that appears to be required for DFF to mediate DNA fragmentation in vitro [X. Liu et al., "Apaf-1, a human protein homologous to *C. elegans* CED-4, participates in cytochrome c-dependent activation of caspase-3," *Cell* 90:405–413 (1997)]. However, the effector moiety of DFF that is activated by caspase-3 remains poorly understood. Furthermore, it is unclear whether DFF is necessary for induction of DNA fragmentation and apoptosis in vivo. DFF is devoid of nuclease activity when incubated with naked DNA suggesting that DFF mediates DNA fragmentation by an indirect mechanism perhaps as a component of a signaling cascade that ultimately leads to DNA fragmentation. To understand the role of DFF in apoptosis, public databases were searched for novel proteins with homology to DFF45.

The present invention, identifies CIDE-A and CIDE-B, two members of a family of proteins that activate apoptosis in mammalian cells. Another member of the family is FSP27, a protein associated with terminal differentiation of fat cells [U. Danesch et al., "Cloning and transcriptional regulation of a novel adipocyte-specific gene, FSP27. CAAT-enhancer-binding protein (C/EBP) and C/EBP-like proteins interact with sequences required for differentiation-dependent expression," *J. Biol. Chem.* 267:7185–7193 (1992)]. The expression of FSP27 is regulated by the tumor necrosis pathway, but it is unknown if FSP27 is involved in the regulation of cell death [P. M. Williams et al., "CCAAT/enhancer binding protein expression is rapidly extinguished in TA1 adipocyte cells treated with tumor necrosis factor," *Mol. Endocrinol.* 6:1135–1141(1992)]. CIDEs and FSP27 contain an N-terminal region with homology to DFF45, a subunit of DFF [X. Liu et al., "Apaf-1, a human protein homologous to *C. elegans* CED-4, participates in cytochrome c-dependent activation of caspase-3," *Cell* 90:405–413 (1997)].

CIDE-A and CIDE-B activate apoptosis and appear to function as positive effectors of the apoptotic pathway. Recent studies have provided insight into the effector mechanism that mediates DNA fragmentation and clues as to how CIDEs could function in apoptosis. Two proteins, CAD and ICAD, have been identified as downstream regulators of DNA fragmentation [M. Enari et al., "Cleavage of CAD inhibitor in CAD activation and DNA degradation during apoptosis," *Nature* 391:43–50 (1998); H. Sakahira et al., "Cleavage of CAD inhibitor in CAD activation and DNA degradation during apoptosis," *Nature* 391:96–99 (1998)]. ICAD exhibits high homology to DFF45 and appears to represent the mouse orthologue of DFF45 [M. Enari et al., "Cleavage of CAD inhibitor in CAD activation and DNA degradation during apoptosis," *Nature* 391:43–50 (1998)]. ICAD interacts with and inhibits the activity of CAD, a 40 kDa protein that exhibits DNase activity and likely represents the mouse counterpart of DFF40 [M. Enari et al., "Cleavage of CAD inhibitor in CAD activation and DNA degradation during apoptosis," *Nature* 391:43–50 (1998)]. Apoptotic stimuli that activate caspase-3 can cleave ICAD/DFF45, leading to the release and activation of CAD [M. Enari et al., "Cleavage of CAD inhibitor in CAD activation and DNA degradation during apoptosis," *Nature* 391:43–50 (1998)], a hypothesis that is compatible with the finding that caspase-3 is required for activation of DFF [X. Liu et al., "Apaf-1, a human protein homologous to *C. elegans* CED-4, participates in cytochrome c-dependent activation of caspase-3," *Cell* 90:405–413 (1997)]. CIDEs could function as signaling components that regulate the ability of CAD to mediate DNA fragmentation. In this model, CIDEs act as upstream regulators of CAD or alternatively they could be co-factors of CAD required for DNase activity. In this regard, CAD has been shown to exhibit DNase activity when expressed in mammalian cells or in an in-vitro reticulocyte system in the presence of ICAD and caspase-3 [M. Enari et al, "Cleavage of CAD inhibitor in CAD activation and DNA degradation during apoptosis," *Nature* 391:43–50 (1998)]. The observation that DNA fragmentation activity induced by CIDEs was not affected by caspase inhibitors is consistent with a model in which CIDEs and CAD act in concert downstream from caspases to mediate DNA fragmentation. However, one cannot rule out an alternative model in which CIDEs could be part of a DFF45-inhibitable pathway that leads to the activation of a DNase activity distinct from CAD.

The C-terminal region of CIDEs appears to contain the effector domain since this region was necessary and sufficient for killing activity. The N-terminal region of CIDEs which is homologous to that of DFF45 could regulate the killing activity of CIDEs perhaps through homophilic interactions. These could involve association of CIDEs with DFF45 or with other proteins containing domains with homology to the N-terminal region of DFF45. This hypothesis is supported by these observations. First, the region of CIDEs with homology to DFF45 was required for DFF45 to inhibit CIDE-mediated apoptosis. Second, the killing activity of the CIDE-A mutant (108–200) was greater than that of the wild type protein, suggesting that CIDE-A is negatively regulated through its N-terminal region that has homology to DFF45. Finally, a mutant form of CIDE-A (1–107) that contained the region with homology to DFF45 antagonized the DFF45 inhibition of CIDE-A-induced apoptosis.

CIDEs induce DNA fragmentation as well as other morphological features of apoptosis including nuclear condensation and membrane blebbing. Two possibilities can be envisioned to explain these observations. First, DNA cleavage elicited by CIDEs could result in secondary activation of effectors responsible for morphological features of apoptosis observed upon CIDE expression. Alternatively, CIDEs could directly engage cytosolic and/or nuclear targets in addition to those responsible for DNA fragmentation.

In addition, DREP-1, a Drosophila protein related to DFF45, is also provided in the present invention. DREP-1 protein may represent the fly homologue of DFF45/ICAD. Three observations support the notion that DREP-1 is the fly homologue of DFF45/ICAD. First, DFF45/ICAD and DREP-1 share significant amino acid and structural homology. The similarity between DREP-1 and DFF45/ICAD was most significant at the N-termini but also extended to their C-terminal regions. Second, two aspartic acid residues known to be part of a caspase-3 recognition site in DFF45/ICAD, were also conserved in DREP-1. These two aspartic residues in DFF45/ICAD are cleaved during the activation of DFF by caspase-3 [X. Liu et al., "Apaf-1, a human protein homologous to *C. elegans* CED-4, participates in cytochrome c-dependent activation of caspase-3," *Cell* 90:405–413 (1997)] and are important for the release of ICAD from CAD [M. Enari et al., "Cleavage of CAD inhibitor in CAD activation and DNA degradation during apoptosis," *Nature* 391:43–50 (1998); H. Sakahira et al., "Cleavage of CAD inhibitor in CAD activation and DNA degradation during apoptosis," *Nature* 391:96–99 (1998)]. Finally, both DFF45 and DREP-1 can inhibit apoptosis induced by CIDEs. These results suggest that DREP-1 is the Drosophila orthologue of DFF45/ICAD and plays an essential role in programmed cell death. The conservation of DFF45/ICAD in flies suggest an important role for these proteins in both vertebrate and invertebrate apoptosis.

Thus, the identification of the CIDE-family of death activator proteins in the present invention, lays the foundation for the development of novel therapeutic approaches, especially in the treatment of diseases associated with aberrant cell growth and proliferation, for e.g., as neoplastic agents.

Kinases involved in the Fas-induced Death pathway: One important mediator of immunologically relevant cell death is the Fas antigen/APO-1 (also known as CD95) ("Fas/APO-1"), originally identified as the target of monoclonal antibodies that could kill multiple cell types [Trauth et al., *Science* 245:301 (1989); Yonehara et al., *J. Exp. Med.*, 169:1747 (1989)]. Cloning of cDNA, followed by sequence analysis [Itoh et al., *Cell* 66:233 (1991); Watanabe-Fukanaga et al., *J. Immunol.* 148:1274 (1992a); Oehm et al., *J. Biol.Chem.* 267:10709 (1992)] showed Fas/APO-1 to be a member of a family of transmembrane receptors that includes the low affinity nerve growth factor ("NGF") receptor, the tumor necrosis factor receptors ("TNFR1," "TNFR2"), and a variety of immune cell receptors including CD40, OX40, CD40, CD27, and 4-1BB ([see Smith et al., *Cell* 76:959 (1994)]. In addition to Fas/APO-1, several members of this family have been shown to regulate or induce cell death, e.g., p55 TNFR (TNFR1) [Tartaglia et al., *Proc. Natl. Acad. Sci.* 88:9292 (1991); Tartaglia et al., *Cell* 73:213 (1993b)] and p75 TNFR (TNFR2) [Heller et al., *Cell* 70:47 (1992); Heller et al., *Cell* 73:216 (1993); Clement and Stamenkovic, *J. Exp. Med.* 180:557 (1994)].The surface CD95 death receptor (also known as Fas or APO1), a member of the tumor necrosis factor (TNF) superfamily, is widely expressed and plays a critical role in the regulation and homeostasis of the immune system [S. Nagata, *Cell* 88:355–365 (1997)]. Activation of CD95 by Fas ligand (FasL), a trimeric cell surface protein, leads to rapid induction of apoptosis [S. Nagata, *Cell* 88:355–365 (1997)]. The intracellular domain of CD95 and related death receptors contains a death domain that was originally described in the tumor necrosis factor (TNF)-receptor-1 [S. Nagata, *Cell* 88:355–365 (1997)]. The death domain of CD95 and TNFR-1 is responsible for signaling cell death [S. Nagata, *Cell* 88:355–365 (1997)].

A major step forward in understanding early events in CD95 signaling was the discovery of molecules that are recruited to the CD95 receptor complex, following ligand induced receptor oligomerization. The Fas-associated protein with death domain, FADD, (also known as MORT-1), is a cytoplasmic adapter protein that contains a C-terminal death domain that interacts with the death domain of CD95 [M.P. Boldin et al., *J. Biol. Chem.* 270:7795–7798 (1995)]. CD95 utilizes FADD to link cytoplasmic receptor sequences to caspase-8 (also known as FLICE, MACH and Mch5) [M. Muzio et al., *Cell* 85:817–827 (1996)]. Both FADD and caspase-8 interact through conserved death effector domains (DED) located in the pro-domain of caspase-8 and N-terminal region of FADD [M. Muzio et al., *Cell* 85:817–827 (1996)]. Following ligand induced oligomerization, the CD95 receptor recruits caspase-8 to the receptor signaling complex through FADD, an event that leads to the processing and release into the cytosol of caspase-8 [J. P. Medema et al., *EMBO J.* 16:2794 –2804 (1997)]. Active caspase-8 induces a cascade of caspases and the rapid demise of the cell [S. Nagata, *Cell* 88:355–365 (1997)].

RIP is a protein kinase that was identified by its ability to interact with the intracytoplasmic region of CD95 [B. Z. Stanger et al., *Cell* 81:513–523 (1995)]. RIP contains a death domain that was shown to mediate the interaction with CD95 [B. Z. Stanger et al., *Cell* 81:513–523 (1995)]. However, it has proven difficult to show interaction between RIP and CD95 in vivo [B. Z. Stanger et al., *Cell* 81:513–523 (1995)]. Furthermore, in some systems RIP mediates activation of NF-kB but not CD95-initiated apoptosis [A. T. Ting et al., *EMBO J.* 15:6189–6196 (1996)], indicating that a kinase other than RIP could be involved in the regulation of CD95-mediated apoptosis. The present invention identifies and characterizes RICK, a novel protein kinase containing a caspase recruitment domain, that interacts with CLARP and FADD and regulates apoptosis signaling upstream of caspase 8. The N-terminus of RICK contains a serine/threonine catalytic kinase domain, and its C-terminal region contains a caspase recruitment domain (CARD) with amino acid homology to the pro-domains of CED-3 related mammalian caspases, *Caenorhabditis elegans* CED-4 and its mammalian homologue, Apaf-1. The RICK and RICK-K38M compositions and fragments thereof, can be used in the development of drug screening assays for the identification of inhibitors of CD95/Fas/APO-1 mediated apoptosis, as mentioned in the section describing preferred embodiments and Uses of the Invention.

For clarity, an abbreviated scheme of the Cell Death Pathway is shown in Schematic A which helps to understand the sites where RICK, ARC and CIDEs may act to regulate cell death.

Schematic A

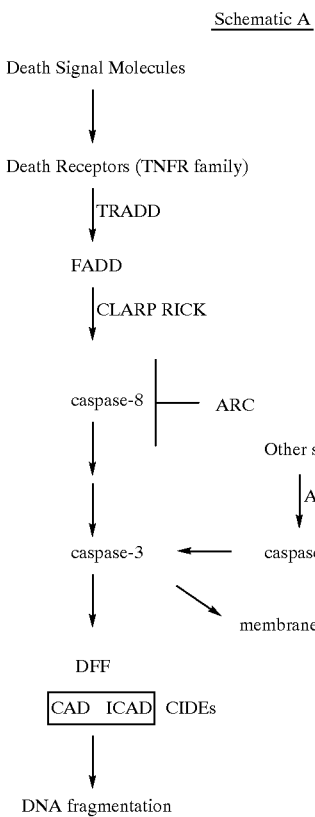

B. Inhibitors and Activators Of The Apoptosis Pathway

The present invention provides the following novel compositions:

(1) CIDEs, [Cell Death Inducing DFF45-like effector], a novel family of Cell Death Activators with homology to the 45kDa subunit of the DNA fragmentation factor [DFF45]. DFF45 is cleaved by caspase-3 during apoptosis. Three compositions that show homology to DFF45 were identified; a) CIDE-A, b) CIDE-B, c) DREP-1. The mammalian genes CIDE-A and CIDE-B, encoding highly related proteins (39% and 29% amino acid identity, respectively, with the N-terminus of DFF45), activate apoptosis in mammalian cells, which is inhibited by DFF45 but not by caspase inhibitors. In addition, DREP-1, a Drosophila melanogaster homologue of DFF45 inhibits CIDE-A-mediated apoptosis. The findings indicate that DFF45 is evolutionarily conserved and implicates CIDEs as DFF45-inhibitable effectors that promote cell death and DNA fragmentation. The CIDEs can be used for the treatment of diseases and/or cancer, as DFF45-inhibitable effectors that promote cell death and DNA fragmentation.

(2) ARC, [Apoptosis Repressor with CARD domain], a novel inhibitor of apoptosis, that is expressed primarily in skeletal muscle and heart tissue, and that interacts selectively with caspases. This human protein (consisting of 208 amino acids), inhibits the enzymatic activity of caspase-8 in 293T calls, and attenuates apoptosis induced by FADD and TRADD and that triggered by stimulation of death receptors coupled to caspase-8, including CD95/Fas, TNFR1, and TRAMP/DR3. The expression of human ARC was primarily restricted to to skeletal muscle and cardiac tissue. Delivery of ARC by gene transfer or enhancement of its endogenous activity may provide a novel strategy for the treatment of diseases that are characterized by inappropriately increased cell death in muscle tissue.

(3) RICK, [RIP-like interacting CLARP kinase], a novel protein kinase (predicted protein of 531 amino acids) containing a caspase recruitment domain (CARD) in its C-terminal region, interacts specifically with CLARP [caspase-like protein with homology to caspase-8] and regulates apoptosis mediated by CD95/Fas receptor pathway. This protein kinase has considerable amino acid homology with the prodomains of CED-3 related mammalian caspases, *Caenorrhabditis elegans* CED-4 and its mammalian homologue, Apaf-1. This protein kinase potentiates apoptosis induced by caspase-8 and caspase-10 and augments the enzymatic activity of caspase-8. In addition, a RICK ATP-binding site mutant (RICK-K38M) was engineered, in which the lysine residue was replaced by methionine at position 38. This mutant functions as a dominant-negative inhibitor of CD95-mediated apoptosis by reducing auto-phosphorylation mediated by the wild-type in 293T cells, in vitro. These compositions can be used in the development of drug screening assays for the identification of inhibitors of CD95/Fas/APO-1 mediated apoptosis.

DETAILED DESCRIPTION OF PREFERRED EMBODIMENTS AND USES OF THE INVENTION

The various apoptosis activator and inhibitor compositions that have been identified in the present invention are useful for the diagnosis and treatment of a wide array of diseases associated with dysregulation of apoptosis, including but not limited to cancer, neurodegeneration, autoimmunity, heart disease, and other disorders.

In preferred embodiments, the CIDEs and fragments thereof can be used for the treatment of diseases and/or cancer, as DFF45-inhibitable effectors that promote cell death and DNA fragmentation.

In other preferred embodiments, ARC, a novel inhibitor of apoptosis that specifically inhibits certain caspases, such as caspase-8. Overexpression of ARC or fragments thereof in an in vitrocell system can be used for identifying other similar inhibitors that block the enzymatic activity of caspase-8 and thereby block CD95-mediated apoptosis. Also, the present invention lays the foundation for the potential use of ARC by gene transfer or by enhancement of its endogenous activity for the treatment of diseases that are characterized by inappropriately increased cell death in muscle tissue.

In yet other preferred embodiments, RICK and RICK-K38M compositions and fragments thereof, can be used in the development of drug screening assays for the identification of inhibitors of CD95/Fas/APO-1 mediated apoptosis, as mentioned below.

Drug Screening Assays And Other Uses Of The Invention

In preferred embodiments, the present invention provides the DNA encoding the protein RICK[CIPERK], an important element in the signal transduction pathway mediating programmed cell death. Various diseases, including AIDS, neurodegenerative disorders, toxin-induced liver disease, involve abnormal increases in apoptosis. A specific inhibitor of an essential step in the biochemical machinery that mediates apoptosis is needed. Such an inhibitor would be a drug candidate for therapeutic use against apoptosis-associated diseases. Because RICK interaction with (i.e., binding to) intracellular factors such as CLARP, FADD, or fragments thereof, appears to be an essential step in triggering apoptosis, inhibitors of RICK binding to intracellular apoptosis factors, are potential drug candidates. RICK (or a fragment thereof) is an essential component in any screening method for discovery of such RICK binding inhibitors. Thus, the compositions RICK, the RICK-K38M (and in particular, fragments of RICK) are useful in drug screening assays designed to identify drugs that interfere with the specific binding of RICK kinase with its substrates, including but not limited to FADD and/or CLARP as well as RICK kinase activity, and thereby block the activation of downstream signaling molecules in the cell death pathway.

In other embodiments, the invention provides an isolated FADD and/or CLARP polypeptide, or a fragment thereof, having RICK kinase-specific binding affinity. The invention provides nucleic acids encoding the RICK polypeptide and RICK fragments as part of expression vectors for introduction into cells. The invention provides methods of identifying intracellular molecules which interact with RICK or RICK fragments, as well as exogenous agents (i.e., drugs) which disrupt the binding of RICK and/or fragments thereof to such intracellular targets.

The claimed polypeptide RICK, the RICK-K38M and RICK fragments thereof, find particular use in screening assays for agents or lead compounds for agents useful in the diagnosis, prognosis or treatment of diseases associated with dysregulation of the apoptotic signaling pathway. For e.g., but not limited to diseases that are associated with increased apoptosis; AIDS, neurodegenerative disorders (e.g., Alzheimer's disease, Parkinson's disease, amyotrophic lateral sclerosis, retinitis pigmentosa), aplastic anemia, ischemic injury (e.g., myocardial infarction, stroke, reperfusion injury), and toxin-induced (e.g., alcohol induced) liver disease. One such assay involves forming mixtures of 1) RICK(or fragments thereof) and 2)an intracellular RICK-binding substrate, in the presence or absence of 3) a prospective drug candidate. The mixtures are made under conditions that permit the binding of the intracellular RICK-binding substrate to RICK (or fragments thereof) and the mixtures are then analyzed for the presence of such binding. A difference in such binding in the presence of such a drug candidate indicates that the agent is capable of modulating the binding of RICK (or fragments thereof) to an intracellular RICK-binding substrate. The assays of the present invention provide for facile high-throughput screening of compounds suspected to be able to inhibit such binding (e.g., compound libraries, peptide libraries, and the like) to identify potential drug candidates.

An example of a drug screening assay, that can be employed to test for potential drug candidates that inhibit the specific binding of RICK kinase with its substrate FADD and/or protein CLARP, is given below. The suspect drug candidates are tested whether they block the binding of CLARPand/or FADD to the full length RICK and incubated for 1 hour with the indicated amount or different doses of the drug candidate. In parallel assays, the RICK-K38M is used as control. (For details see methodology and in particular FIG. 11, 12 and Example 10 in the Experimental Section)

Another example of a drug screening assay, that can be employed to test for potential drug candidates that inhibit the ability of RICK to phosphorylate itself, or FADD, or any other protein or peptide. The suspect drug candidates are tested whether they block the ability of RICK to phosphorylate. In parallel assays, the RICK-K38M is used as control.

RICK inhibitor screening methods, including cell-free methods and cellular methods, can be used in the practice of this invention. Cellular screening methods within the scope of this invention can involve transient expression vectors or stable transformation. Various RICK inhibitor screening protocols can be designed, according to well-known principles, by one of ordinary skill in the art.

Cell-free screening methods for inhibitors of RICK death domain-mediated binding involve the use of isolated RICK and an RICK interaction partner, e.g., isolated CLARP and/or FADD and/or CD95 or a polypeptide comprising the appropriate binding domain of one of these proteins. Soluble forms of RICK and RICK interaction partners can be utilized in cell free RICK inhibitor screening protocols.

Preferably, RICK inhibitor screening is carried out in a cellular system, using a reporter strain of cultured mammalian cells, transformed with one or more vectors encoding RICK, and other assay components, as necessary.

Preferably, an RICK-encoding sequence is cloned into a recombinant DNA vector, where it is expressed under the control of an inducible promoter, e.g., a heat shock promoter. [See, e.g., Wurm et al., *Proc. Natl. Acad. Sci. U.S.A*. 83:5414 (1986)]. Following induction of RICK expression, cell death is measured in experimental treatments involving the presence of an inhibitor candidate, and in appropriate positive and negative controls.

Various assays for cell death are known in the art, including the neutral red uptake method [Wallach, *J. Immunol*. 132:2464 (1984)], the crystal violet method [N. Itoh et al., *Cell* 26:233–243) (1991)], or microscopic inspection of cells for visual signs of apoptosis.

Because overexpression of RICK can be used to induce apoptotic cell death, RICK may be useful as a tool in gene therapy in at least two different ways: (1) to control the number of cells bearing a specific gene; and (2) to act as an anti-tumor agent in forms of cancer therapy that are dependent on the delivery of a lethal gene to neoplastic cells. In both applications, overexpression of RICK to cause apoptotic cell death is preferable to approaches employing death-inducing genes that result in in vivo generation of toxic agents or that interfere with cell cycle progression.

Cell ablation through RICK expression is advantageous because apoptotic death affects both mitotically active and mitotically quiescent cells. In contrast, chemotherapeutic agents and many gene therapy-based treatments for tumors require the target cell to be replicating in order for the treatment to be effective.

RICK genes that may be used in gene therapy are preferably under the control of an exogenously regulatable promoter. An exogenously regulatable promoter is a promoter that can be induced by a specific set of environmental conditions, such as the increase in the concentration of a specific inducer. Examples of exogenously regulatable promoters and inducing conditions include: induction of a metallothionein promoter by zinc ions [Makarove et al., *Nucleic Acids Res*. 22:1504–1505 (1994)], removal of tetracycline, thereby activating a synthetic promoter based on the action of a tetracycline repressor-VP16 chimera [Gossen et al., *Proc. Natl. Acad. Sci. U.S.A*. 89:5547–5551 (1992)], addition of ecdysone [Christopherson et al., *Proc. Natl. Acad. Sci. U.S.A*. 89:6314–6318 (1992)], or the synthetic progesterone antagonist mifepristone [Wang et al., *Proc. Natl. Acad. Sci. U.S.A*. 91:8180–8184 (1994)].

Antibodies

The RICK-encoding DNA of this invention enables one of ordinary skill in the art to produce anti-RICK antibodies. The RICK-encoding DNA is used to construct a vector encoding a fusion protein comprising an RICK moiety and an isolation-facilitating moiety, i.e., a moiety that can be readily isolated from contaminating proteins in an extract from a host cell used to express the fusion protein. A preferred isolation-facilitating moiety is maltose binding protein. DNA encoding maltose binding protein is commercially available. A binding reagent specific for the isolation-facilitating moiety is used for convenient and efficient isolation of the RICK fusion protein. For example, amylose chromatography is preferred for isolation of a fusion protein comprising maltose binding protein moiety. Following isolation, the RICK fusion protein is used to produce RICK-specific antibodies (polyclonal or monoclonal), according to standard methods, known to a person skilled in the art.

The anti-RICK antibodies of the invention have several uses. For example, they may be used as reagents for preparation of affinity chromatography media. Once the anti-RICK antibodies of this invention are in hand, preparation of RICK affinity chromatography media can be carried out according to conventional methods known to a person skilled in the art, using commercially available reagents. The RICK-specific affinity chromatography media can be used to isolate full-length RICK from natural sources or from host cells transformed with recombinant DNA encoding RICK. The anti-RICK antibodies of the invention are also useful as analytical-scale laboratory reagents for research on the physiology and cell biology of apoptosis. For example, immunohistochemical techniques, based on anti-RICK monoclonal antibodies are likely to be valuable tools for embryologists seeking ways to observe the rate and/or distribution of apoptosis in the normal morphological development of metazoan animals.

The anti-RICK antibodies of the invention are also useful as diagnostic immunoassay reagents for measuring RICK levels in tissue samples from patients suspected of having an apoptosis-related disease or abnormality. Information on RICK levels in selected cells or tissues is a useful diagnostic or prognostic indicator in any situation where the rate of programmed cell death is important. The type of tissue sampled for the diagnostic test will vary, depending on the signs and symptoms of the patient and the suspected disease or abnormality.

If the tissue sample is highly homogenous with respect to cell type, it may be preferable to carry out the RICK immunoassay on an extract from a homogenate. Alternatively, it may be preferable to use an immunohistochemical assay involving anti-RICK antibodies. An immunohistochemical assay is preferable when the tissue sample is heterogeneous with respect to cell type. An immunohistochemical assay will yield information on the distribution of differing RICK levels in a cross section of tissue, or differing RICK levels in various types of blood cells in a blood sample.

Although inhibitors of RICK binding to intracellular apoptosis factors would be expected to have therapeutic utility only for disease states involving increased apoptosis, information on the level of RICK in a tissue sample may have diagnostic/prognostic utility for any apoptosis-related disease, regardless of whether apoptosis was increased or decreased in that disease. Examples of diseases associated with decreased apoptosis include cancer (in particular, follicular lymphomas, carcinomas with p53 mutations, hormone-dependent tumors, e.g., breast cancer, prostate cancer, ovarian cancer), autoimmune disorders (e.g., systemic lupus erythematosus, immune-mediated glomerulonephritis), viral infections, herpes viruses, poxviruses, adenoviruses).

The anti-RICK antibodies of the present invention can be used in various diagnostic immunoassay formats known in the art. Exemplary immunoassay formats are competitive radioimmunoassay, ELISA, Western blot analysis and microcapillary devices comprising immobilized antibody. [See, e g., Dafforn et al, Clin. Chem. 36:1312 (19900; Li et al., Anal. Biochem. 166:276 (1987); Zuk et al., U.S. Pat. No. 4,435,504; Zuk et al., Clin. Chem. 31:1144 (1985); Tom et al, U.S. Pat. No. 4,366,241; and Clark, PCT published application WO 93/03176].

The RICK-encoding DNA of this invention can be used as an in situ hybridization reagent to assess transcription of RICK genes and observe RICK RNA processing, for diagnostic purposes or research purposes.

A wide variety of host/expression vector combinations can be employed for expressing RICK-encoding DNA of this invention. The expression of RICK-encoding DNA in a cellular screening assay is preferably in a eukaryotic cell, under the control of eukaryotic expression control sequences. More preferably, the eukaryotic cell is a cultured mammalian cell. If the expression of recombinant RICK-encoding DNA is merely for the production of isolated recombinant RICK, however, a prokaryotic host/expression vector system or a eukaryotic host/expression system can be used.

EXPERIMENTAL

The following examples serve to illustrate certain preferred embodiments and aspects of the present invention and are not to be construed as limiting the scope thereof. In the experimental disclosure which follows, the following methodologies apply:

METHODOLOGY

The methods employed for the identification and characterization of the different activators and inhibitors of apoptosis of the present invention are as follows:
(a) Methods employed for Identification of ARC Isolation of ARC and construction of expression plasmids: The partial nucleotide sequences of cDNAs encoding peptides with homology to the CARD of caspase-9 (amino acids 1–80) were found in EST databases of GenBank using the TBLASTN program. The entire nucleotide sequence of a eDNA containing a 1.0 Kb insert corresponding to EST clones 322821, 546171 and 588443 was determined by dideoxy-sequencing. The entire open reading frame of ARC from EST clone 322821 was tagged at the C-terminus with FLAG or HA sequences and cloned into the expression vector pcDNA3 (Invitrogen) to produce pcDNA3-ARC-Flag or pcDNA3-ARC-HA. The human caspase-8 (amino acids 1–215) and caspase-8 (amino acids 216–496) were fused at the C-terminus with HA tag sequences and cloned into pcDNA3 to produce pcDNA3 -N-caspase-8-HA or pcDNA3-C-caspase-8-HA, respectively. The authenticity of all constructs was confirmed by dideoxy sequencing. pcDNA3-caspase-1-Flag, pcDNA3-caspase-3-Flag, pcDNA3-caspase-8-AU1, pcDNA3-caspase-8-mt(C377S)-AU1, pcDNA3-caspase-9-Flag, pcDNA3-Ced-3-Flag, pcDNA3-FADD-AU1, pcDNA3-HA-TRADD pcDNA3-CLARP-myc and pcDNA3-p35 were previously described (10,24–25). pcDNA3-FAS and pcDNA3-TNFR1-Flag were obtained from Genentech.

Northern Blot Analysis: A 1.0 kb fragment containing the ARC coding sequence was radiolabeled by random priming using a commercial kit (Boeringer Mannheim) and applied for analysis of human multiple poly-(A)$^+$ mRNA blots (Clontech Laboratories) according to the manufacturer's instructions.

Transfection, Expression, Immunoprecipitation And Immunodetection Of Tagged Proteins: $5 \times 10^6$ human 293T cells were transfected with expression plasmids by a calcium phosphate method as described previously [N. Inohara el al., EMBO J. 16:1686–1694 (1997)]. Briefly, 2 μg of pcDNA3 or pcDNA3-ARC-Flag or -HA was co-transfected with 3 μg of pcDNA3 or caspase expression plasmids. Total amount of transfected plasmid DNA was always 5 μg. 293T cells were harvested after 22 hr and lysed with 0.2% NP-40 isotonic lysis buffer [Z. N. Oltvai et al., Cell 74:609–619 (1993)]. For immunoprecipitation, 1 μg of soluble protein was incubated with 10 μg/ml of polyclonal anti-Flag, monoclonal anti-AU1 or polyclonal anti-HA antibody for 2 hr at 4° C. and tagged proteins were immunoprecipitated with Protein A-Sepharose 4B (Zymed Laboratories Inc., San Francisco, Calif.). Immunoprecipitates were subjected to 12% SDS-polyacrylamide electrophoresis and immunoblotted with anti-Flag, anti-AU1 or anti-HA antibodies.

β-galactosidase apoptosis assay and Caspase-8 enzymatic assay: $5 \times 10^5$ 293T cells were transfected with 0.3 μg of pcDNA3-β-gal plus each expression plasmid in triplicate. Cells were fixed 16 hrs after transfection, stained for β-galactosidase and assayed for morphological features of apoptosis [M. Muira et al., Cell 75:653–660 (1993)]. Statistical significance was determined by one-way ANOVA followed by Student-Neuman-Keuls post-doc comparisons. For caspase-8 enzymatic assay, $1.5 \times 10^6$ human 293T cells were co-transfected with pcDNA3, pcDNA3-ARC-Flag, pcDNA3-caspase-8 and pcDNA3-caspase-8-mt by a calcium phosphate method. Total amount of transfected plasmid DNA was always 2.5 μg. 293T cells were harvested 18hr after transfection and lysed with 0.2% NP-40 isotonic lysis buffer. Tagged proteins were immunoprecipitated and caspase activity was measured as described [N. Inohara et al., Proc. Natl. Acad. Sci. USA 94:10717–10722 (1997)].

(b) Methods employed for Identification of RICK

Isolation of Rick cDNA: The partial nucleotide sequences of cDNAs encoding peptides with homology to CIPER-1 were found in EST databases of GenBank using the TBLASTN program. The entire nucleotide sequence of EST clone 591081, 239957 and 633044 was determined by dideoxy-sequencing.

Northern Blot Analysis: The entire cDNA insert of EST clone 591081 was radiolabeled by random priming using a commercial kit (Boeringer Maniheim) and applied for analysis of human poly(A)+ RNA blots from various tissues (Clontech Laboratories) according to the manufacturer's instructions.

Construction of Expression Plasmids: The entire cDNA insert (1.8 kbp) of EST clone 591081 was cloned into the EcoRl and NotI sites of pcDNA3 (Invitrogen) to produce pcDNA3-RICK. The entire open reading frame of RICK was inserted into the XbaI and ApaI sites of pcDNA3-Flag to produce N-terminal Flag-tagged CIPER-1. Deletion mutants of RICK (Δ53, Δ247, ,Δ366–531) were constructed by digestion of the pcDNA3-Flag-RICK construct with restriction enzymes AflI, NdeI, XbaI and XbaI/ApaI, respectively. The human caspase-10 cDNA was cloned into the BamHI and XhoI sites of pcDNA3-AU1 to produce C-terminal AU1-tagged caspase-10. pcDNA3-p35, pcDNA3-caspase-8-AU1 and pcDNA3-caspase-8-mt-AU1 were previously described [N. Inohara et al, Proc. Natl. Acad. Sci. U.S.A. 94:10717–10722 (1997)]. The human caspase-1, caspase-2, caspase-10 cDNAs were cloned into the BamHI and XhoI sites of pcDNA3-AU1 to C-terminal AU1-tagged AU1 proteins. The human CLARP cDNA, its alternative splicing form CLARP-N and the mutant CLARP-C, were cloned into the BamHI and XhoI sites of pcDNA3-HA to produce C-terminal HA-tagged proteins.

Transfection, Expression, Immunoprecipitation and Immunodetection of Tagged Proteins: $5 \times 10^6$ human 293T cells were transfected with expression plasmids by a calcium phosphate method as described [N. Inohara et al., Proc. Natl. Acad. Sci. U.S.A. 94:10717–10722 (1997)]. The total amount of transfected plasmid DNA was adjusted with pcDNA3 plasmid to be the same within individual experiments. After transfection, 293T cells were harvested at different times and lysed with 0.2% NP-40 isotonic lysis buffer [N. Inohara et al., Proc. Natl. Acad. Sci. U.S.A. 94:10717–10722 (1997)]. The B lymphocyte-derived BJAB cell line was stably trasnfected by electroporation with pcDNA3 or pcDNA3-Flag-RICK (K38M). After selection with puromycin (1 μg/ml), bulk cell lines were tested for RICK protein expression with anti-Flag antibody by flow cytometric analysis. For immunoprecipitation, 1 mg of soluble protein was incubated with 10 μg/ml of polyclonal anti-Flag, anti-myc or control antibody overnight at 4° C. and tagged proteins were immunoprecipitated with Protein A-Sepharose 4B (Zymed Laboratories Inc.). Immunoprecipitated proteins or total lysates were subjected to 12% SDS-polyacrylamide electrophoresis and immunoblotted with monoclonal antibodies (mAb) to HA (Boeringer Mannheim) or Flag (Kodak).

Apoptosis Assays: $5 \times 10^5$ 293T cells were co-transfected with 0.2 μg of pcDNA3-β-gal plus each expression plasmid in triplicate by the calcium phosphate method as reported [N. Inohara et al., Proc. Natl. Acad. Sci. U.S.A. 94:10717–10722 (1997)]. In some experiments, 20 μM of the caspase inhibitor zVAD-fmk (Enzyme Systems Products) or 12.5 μl of medium from COS-6 cells producing Fas ligand (Immunex Corporation, Seattle, Wash.) was added at 8 hrs after transfection. At 18 or 24 hours after transfection, cells were fixed, stained for β-galactosidase as described [N. Inohara et al., Proc. Natl Acad. Sci. U.S.A. 94:10717–10722 (1997)] and assayed for morphological features of apoptosis. At least 300 hundred blue-staining cells were counted. BJAB apoptosis induced by anti-Apol mAb was determined by flow cytometric analysis of nuclei stained with propidium iodide as described [R. Merino et al., J. Immunol. 155:3830–3838 (1995)]. Statistical significance was determined by one-way ANOVA followed by Student-Neuman-Keuls post-doc comparisons.

Caspase Enzymatic Assay: The human FADD cDNA was cloned into the BamHI and XhoI sites of pcDNA3-myc to produce C-terminal myc-tagged FADD. $5 \times 10^6$ 293T cells were transfected with 5 μg of pcDNA3, pcDNA3-caspase-8-AU1 or pcDNA3-caspase-8-mt-AU1 [N. Inohara et al., Proc. Natl. Acad. Sci. U.S.A. 94:10717–10722 (1997)] plus 5 μg of pcDNA3, pcDNA3-FADD-myc or pcDNA3- Flag-RICK. At 16 hours after transfection, cells were harvested and lysed with NP-40 buffer [N. Inohara et al., Proc. Natl. Acad. Sci. U.S.A. 94:10717–10722 (1997)]. AU1-tagged proteins were immunoprecipitated with mAb to AU1 and the Ac-DEVD-AMC cleavage activity was measured as previously described [N. Inohara et al., Proc. Natl. Acad. Sci. U.S.A. 94:10717–10722 (1997)].

Autophosphorylation of RICK: $5 \times 10^6$ human 293T cells were transfected with 8 μg of pcDNA3, pcDNA3-Flag-RICK or pcDNA3-Flag-RICK-K38M. Flag-RICK proteins were immunoprecipitated mAb to Flag. Kinase assay was performed as described [L. del Peso et al., Science 278:687–689 (1997)]. As control experiment, one twentieth of total lysate was immunoblotted with mAb to Flag.

(c) Methods employed for Identification of the CIDE Family of Proteins

Isolation of the DFF45-related genes: cDNA clones of mouse CIDE-A, human CIDE-A, mouse CIDE-B, DREP-1 were found in GenBank expression sequencing tag (EST) database, using the TBLASTN program. The EST clones 337992 (mCIDE-A), 351557 (mCIDE-A and mCIDE-A*), 152917 (hCIDE-A), 551880, 790532 (mCIDE-B), LD15946, LD16627 (DREP-1) and 525788 (hDFF45), which encode whole proteins were obtained from IMAGE Consortium and their nucleotide sequences were determined by dideoxy sequencing.

Northern Blot Analysis: The entire cDNA inserts of EST clones 337992 (mCIDE-A) and 790532 (mCIDE-B) were radiolabeled by random priming using a commercial kit (Boeringer Mannheim) and applied for analysis of human poly(A)$^+$ RNA blots from various tissues (Clontech Laboratories) according to the manufacturer's instructions.

Construction of Expression Plasmids: The entire cDNA inserts of EST clones 337992 (mCIDE-A), 351557 (mCIDE-A*), 790532 (mCIDE-B), LD15946 (DREP-1) and 525788 (hDFF45) were cloned into the EcoRI and NotI sites of pcDNA3 (Invitrogen) to produce expression plasmids. To produce tagged proteins, we constructed pcDNA3-Flag and pcDNA3-HA which are derivatives of pcDNA3 (Invitrogen) and share common restriction enzyme sites for cloning. The entire open reading frame of mCIDE-A, mCIDE-A*, mCIDE-B, DREP-1 and hDFF45 were inserted into the XbaI and ApaI sites of pcDNA3-Flag to produce N-terminal Flag-tagged proteins. Deletion mutants, CIDE-A (1–107) and CIDE-A (108–200) were constructed by a two-step PCR mutagenesis method as described [N. Inohara et al., "harakiri, a novel regulator of cell death, encodes a protein that activates apoptosis and interacts selectively with survival-promoting proteins Bcl-2 and Bcl-X$_L$," EMBO J. 16:1686–1694 (1997b)]. pcDNA3-crmA, pcDNA3-caspase-8-AU1 were previously described [N. Inohara et al., "CLARP, a death effector domain-containing protein interacts with caspase-8 and regulates apoptosis," Proc. Natl. Acad. Sci. USA 94:10717–10722 (1997a)]. The human CLARP was cloned into the BamHI and XhoI sites of pcDNA3-HA to C-terminal HA-tagged CLARP protein. The authenticity of all constructs was confirmed by dideoxy sequencing and the expression of tagged proteins was confirmed by Western blot using mAbs to Flag (Kodak) and HA (Boeringer Mannheim).

Transfection, Expression, and Immunodetection of Tagged proteins: 5×10$^6$ human 293T cells [F. Numa et al., "Elevated levels of syndecan-1 expression confer potent serum-dependent growth in human 293T cells," Cancer Res. 55:4676–4680 (1995)] were transfected with expression plasmids by a calcium phosphate method as described [N. Inohara et aL, "CLARP, a death effector domain-containing protein interacts with caspase-8 and regulates apoptosis," Proc. Natl. Acad. Sci. USA 94:10717–10722 (1997a)].

The total amount of transfected plasmid DNA was adjusted with pcDNA3 plasmid to be always the same within individual experiments. After transfection, 293T cells were harvested at 24 hours and lysed with 0.2% NP-40 isotonic lysis buffer [N. Inohara et al., "harakiri, a novel regulator of cell death, encodes a protein that activates apoptosis and interacts selectively with survival-promoting proteins Bcl-2 and Bcl-X$_L$," EMBO J. 16:1686–1694 (1997b)].

Total lysates were subjected to 12% SDS-polyacrylamide electrophoresis and immunoblotted with mAbs to Flag (Kodak).

Apoptosis Assays, fluorescence staining of nuclear DNA and DNA fragmentation assay: 5×10$^5$ 293T cells were co-transfected with 0.2 µg of pcDNA3-β-gal plus each expression plasmid in triplicate by the calcium phosphate method as reported [N. Inohara et al, "CLARP, a death effector domain-containing protein interacts with caspase-8 and regulates apoptosis," Proc. Natl. Acad. Sci. USA 94:10717–10722 (1997a)].

MCF7 were cotransfected with vector control or CIDE-A and β-galactosidase-expressing reporter construct by Lipofectamine (Gibco BRL) according to the manufacturer's instructions. In some experiments, 20 µM zVAD-fmk (benzyloxycarbonyl-Val-Ala-Asp-(OMe)-fluoromethylketone), zFA-fmk (benzyloxycarbonyl-Phe-Ala-(OMc)-fluoromethylketone) and zDEVD-fmk (benzyloxycarbonyl-Asp-Glu-Val-Asp-(OMe)-fluoromethylketone) were added into medium at 8 hr after transfection. zFA-fmk, zVAD-fmk and zDEVD-fmk were obtained from Enzyme Systems. At 24 hours after transfection, cells were fixed, stained for β-galactosidase as described [N. Inohara et al., "CLARP, a death effector domain-containing protein interacts with caspase-8 and regulates apoptosis," Proc. Natl. Acad. Sci. USA 94:10717–10722 (1997a)] and assayed for morphological features of apoptosis. At least 300 hundred blue-staining cells were counted. Statistical significance was determined by one-way ANOVA followed by Student-Neuman-Keuls post-doc comparisons.

Nuclear staining with acridine-orange was performed as described [N. Inohara et al., "harakiri, a novel regulator of cell death, encodes a protein that activates apoptosis and interacts selectively with survival-promoting proteins Bcl-2 and Bcl-X$_L$.," EMBO J. 16:1686–1694 (1997b)]. Genomic DNA was extracted and analyzed for DNA fragmentation as described [X. Liu et al., "Apaf-1, a human protein homologous to C. elegans CED-4, participates in cytochrome c-dependent activation of caspase-3," Cell 90:405–413 (1997)].

EXAMPLE 1

Figures 1A, 1B, 1C:
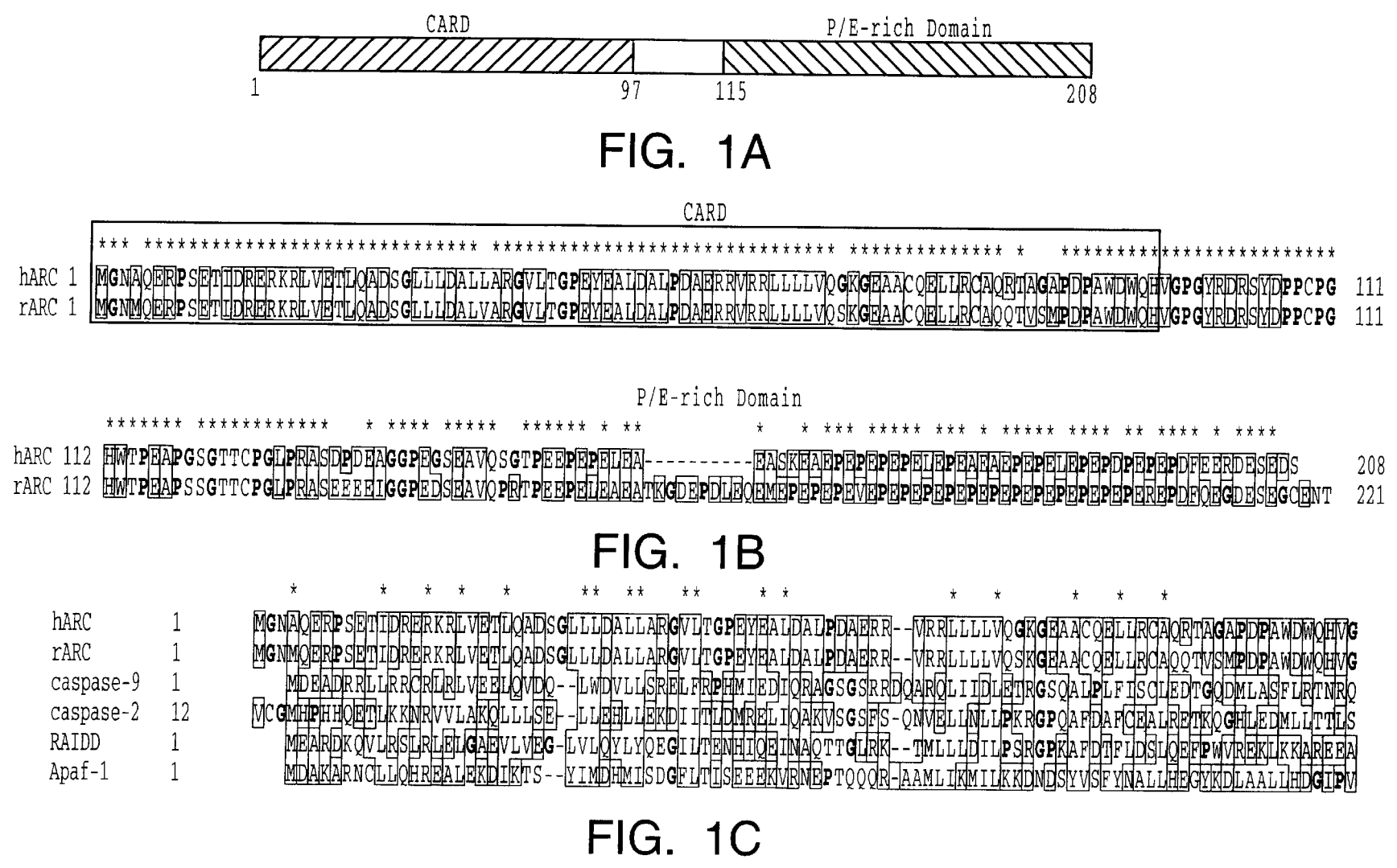

In this example, the identification of ARC, a human protein with homology to the pro-domains of caspases and Apaf-1 is described. To identify novel apoptosis-regulatory proteins, the GenBank data base was screened for cDNAs encoding proteins with homology to the CARD of caspase-9 (amino acid residues 1–80) by computer homology search. Several human expressed-sequence tags (ESTs) containing overlapping nucleotide sequences with significant amino acid homology to caspase-9 were identified. The longest CDNA (EST clone 322821) was 1.0 Kb, and its nucleotide sequence revealed an open reading frame that encoded a protein of 208 amino acids with a predicted relative molecular mass of 22,629 (See FIG. 1A). This human protein was designated as ARC (poptosis epressor with CARD). The amino acid sequence of human ARC was highly homologous (82% identical) to a predicted 221 amino acid rat protein of unknown function whose cDNA was identified through a screening for proteins containing glutamate-proline repeats [R. Geertman et al., Biochem. Biophys. Acta 1306:147–152 (1996)]. Alignment analysis revealed that both human and rat ARC are proteins containing an N-terminal CARD [K. Hofmann et al., Trends Biochem. Sci. 22:155–156 (1997)], and a C-terminal region rich in proline and glutamic acid residues (See FIG. 1B). The CARD of human and rat ARC have significant amino acid similarity to the CARDs from caspase-2, caspase-9, RAIDD and Apaf-1 (See FIG. 1C).

EXAMPLE 2

Figure 2:
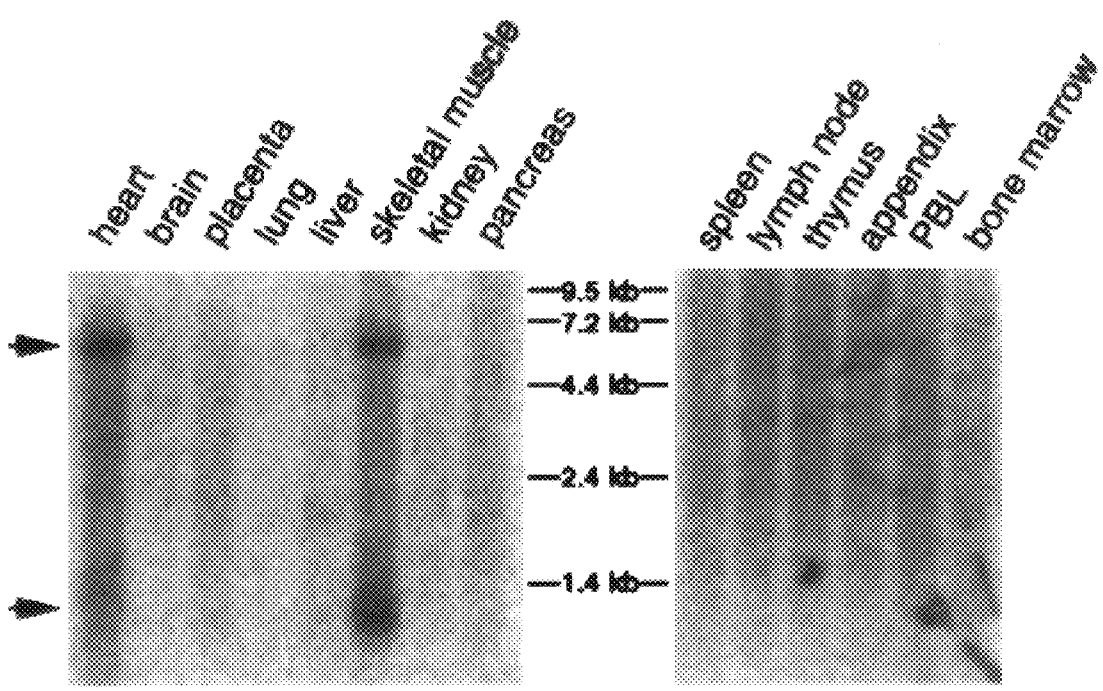
FIG. 2 shows the expression of ARC in human tissues by Northern blot analysis. Poly(A)$^+$ RNAs from various tissues were hybridized with a probe 20 corresponding to the entire human ARC cDNA.

In this example, the expression of human ARC in skeletal muscle and heart tissue is described. Northern blot analysis was performed to assess the expression of arc mRNA in various human tissues. Hybridization with an ARC probe showed two transcripts of approximately 5.5 Kb and 1.0 Kb in skeletal muscle and heart but not in brain, placenta, lung, liver, kidney, pancreas or various lymphoid-hematopoietic tissues (See FIG. 2). The 1.0 kb transcript represented the cDNA analyzed in the experiments of the present invention. The 5.5 Kb mRNA transcript may represent a RNA form of ARC derived by alternative splicing, usage of an alternative poly adenylation sites or cross-hybridization of the probe with sequences of a related gene.

EXAMPLE 3

In this example, experiments are described that demonstrate overexpression of ARC inhibits apoptosis induced by caspases as well as that mediated by stimulation of death receptor pathways. In addition, this example shows ARC suppresses apoptosis, by inhibiting the enzymatic activity of caspase-8.

Figure 3B:
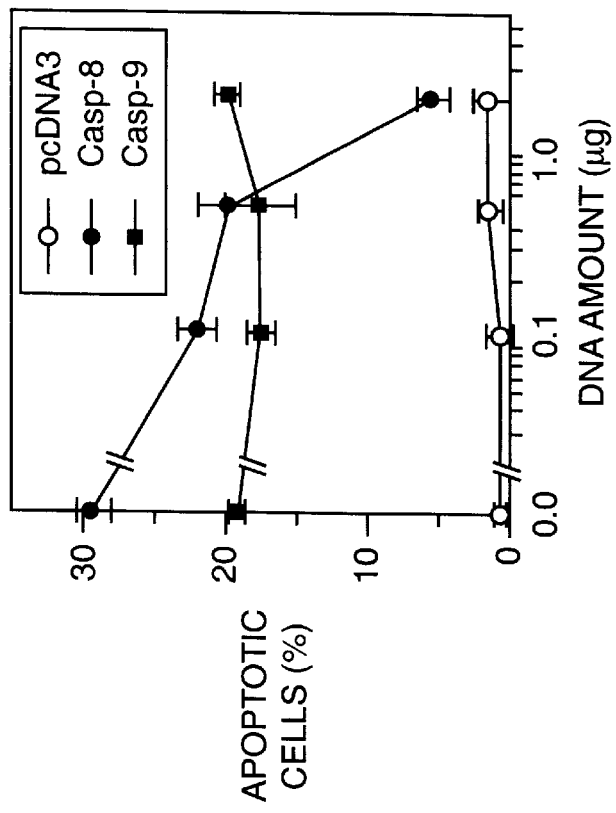
FIG. 3(B) shows ARC inhibits caspase-induced apoptosis in a dose-dependent manner.
Figure 3A:
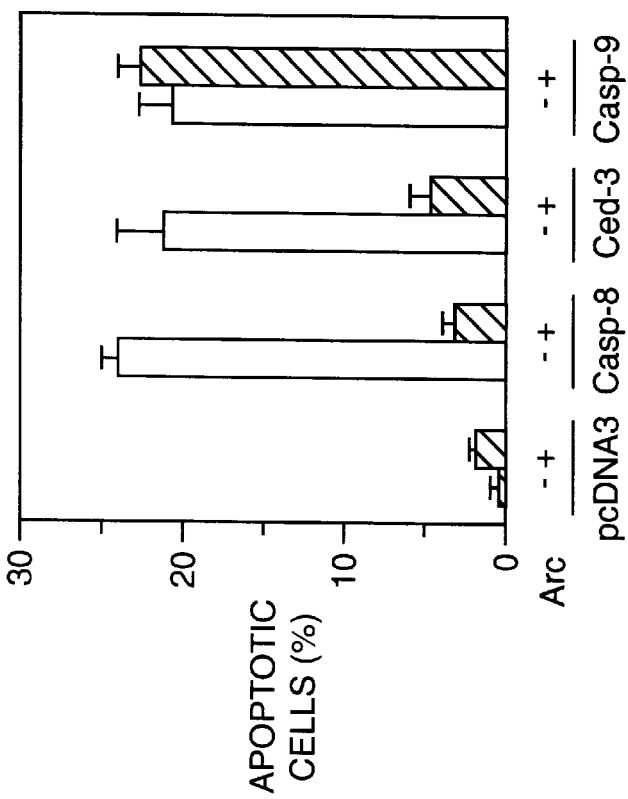
FIG. 3(A) Caspases were co-transfected with ARC (pcDNA3-ARC-Flag, closed bar) or without ARC (pcDNA3, open bar), and scored for percentage of apoptotic cells.

To elucidate the physiological function of ARC, an expression construct producing ARC was introduced into human kidney epithelial 293T cells and subsequently observed for features of apoptosis. Expression of ARC did not induce apoptosis of 293T cells (data not shown). Because the N-terminal region of ARC exhibited homology to the prodomains of several apical caspases, it was reasoned that ARC might regulate the killing activity of caspases. To test that, plasmids producing several caspases known to activate cell death were co-expressed with ARC in 293T cells. Expression of ARC inhibited apoptosis induced by caspase-8 and *C. elegans* CED-3 ($p<0.01$) but not that mediated by caspase-9 (See FIG. 3A). Further experiments revealed that ARC inhibited caspase-8-induced killing in a dose-dependent manner (See FIG. 3B).

Figure 4A:
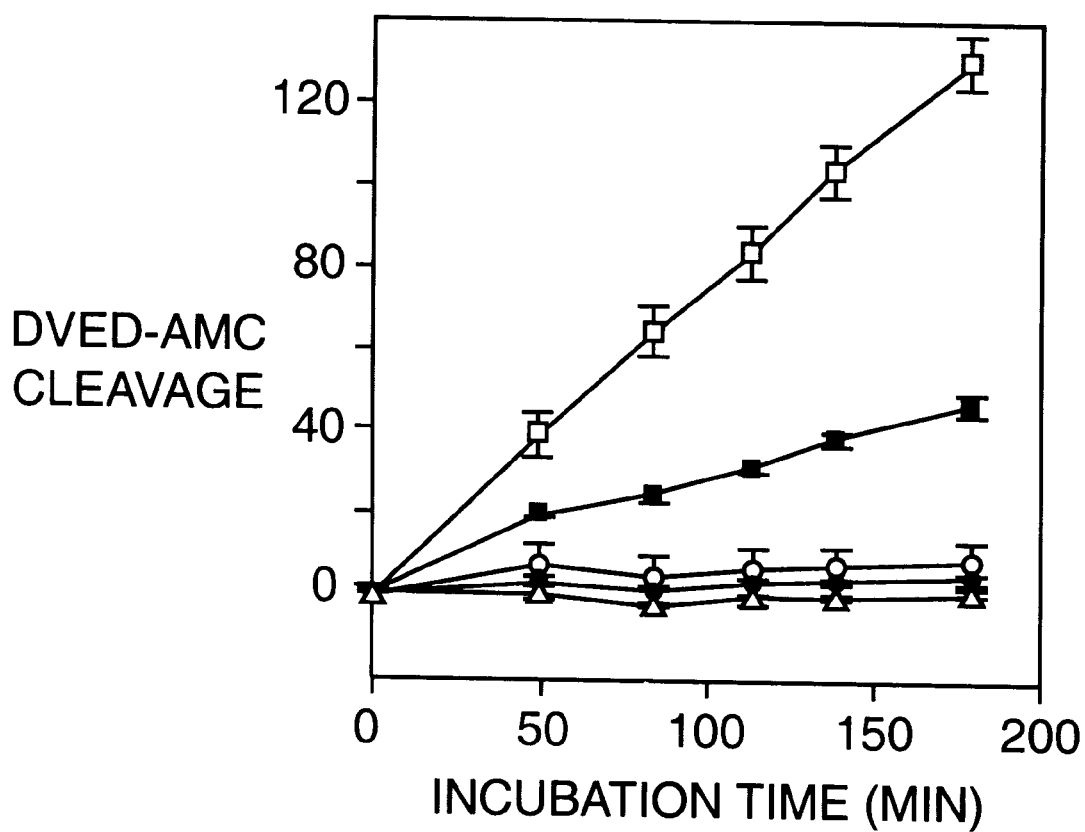
FIG. 4(A) shows ARC suppresses the enzymatic activity of caspase-8 in 293T cells. [293T cell were co-transfected with pcDNA3-caspase-8-AU1 or pcDNA3-caspase-8-mut and pcDNA3-ARC-Flag or pcDNA3]. Caspase-8 in cell extracts was immunoprecipitated with anti-AU1 antibody and immunoprecipitates were incubated with the fluorogenic substrate DEVD-AMC. ○:pcDNA3 alone; ●:pcDNA3-ARC-HA alone; □:pcDNA3-caspase-8-AU1 alone; ■:pcDNA3-caspase-8-AU1 and pcDNA3-ARC-HA; ▲:pcDNA3-caspase-8-mt-AU1 alone.
Figure 4B:
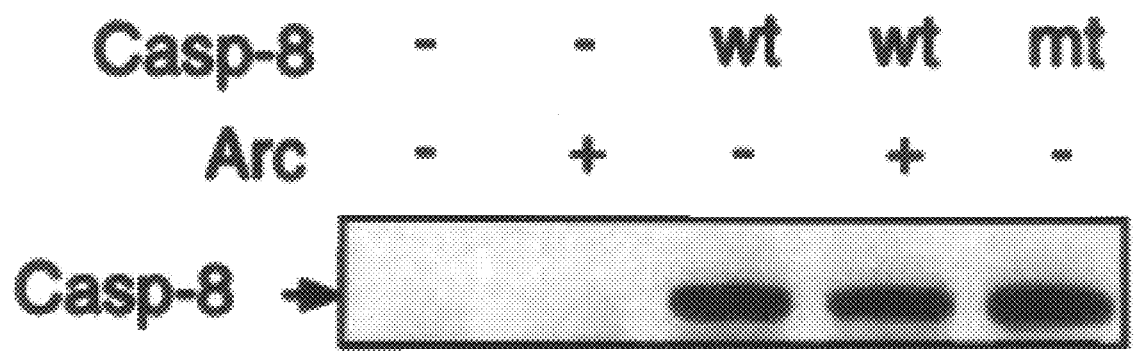
FIG. 4(B) is a representative immunoblot showing detection of AU1-tagged caspase-8 and caspase-8-mt in immunoprecipitates with anti-AU1 by immunoblotting.

Since, stimulation of several members of the TNF family of receptors including TNF-R1, CD95/Fas and TRAMP/DR3 induce apoptosis through engagement of the apical protease caspase-8 [K. Hofmann et al., *Trends Biochem. Sci.* 22:155–156 (1997); M. Muzio et al., *Cell* 85:817–827 (1996); A. M. Chinnaiyan et al., *Science* 274:990–992 (1996)]; experiments were performed to assess the regulation by ARC of apoptosis induced by signaling molecules that function upstream of caspase-8 in the death receptor pathways. As shown in FIG. 3C, ARC inhibited apoptosis induced by FADD and TRADD, two signaling molecules of CD95/Fas and TNF-R1 pathways respectively ($p<0.01$), whose stimulation leads to activation of caspase-8 and apoptosis [A. M. Chinnaiyan et al., *Cell* 81:505–512 (1995); H. Hsu et al., *Cell* 19:495–504 (1995); F. C. Kischkel et al., *EMBO J.* 14:5579–5588 (1995); A. M. Chinnaiyan et al., *J. Biol. Chem.* 271:4961–4965 (1996)]. In addition, ARC inhibited apoptosis induced by CLARP, a caspase-like protein that interacts with caspase-8 [N. Inohara et al., *Proc. Natl. Acad. Sci. USA* 94:10717–10722 (1997)]. Consistent with the results shown in FIG. 3C, expression of ARC partially but significantly inhibited apoptosis induced by stimulation of CD95/Fas, TNF-R1 and TRAMP/DR3 receptors ($p<0.01$) (FIG. 3D). The experiments described above indicated that ARC inhibits apoptosis induced by several caspases including caspase-8. Thus, experiments were performed to test whether ARC could regulate the enzymatic activity of caspase-8, a function that is required for caspase-8 to activate apoptosis [M. P. Boldin et al., *Cell* 85:803–815 (1996); M. Muzio et al., *Cell* 85:817–827 (1996)]. To examine if ARC regulates the enzymatic activity of caspase-8 in intact cells, 293T cells were transiently transfected with expression plasmids producing Flag-tagged caspase-8 and ARC or control plasmid. Caspase-8 was immunoprecipitated with anti-Flag antibody and the immunoprecipitates were assayed for caspase activity using the fluorogenic substrate DVED-AMC. Enzymatic analysis showed that ARC inhibited the enzymatic activity of caspase-8 (FIG. 4A). In control experiments, immunoprecipitates from cells transfected with control plasmid or constructs expressing ARC alone or a caspase-8 mutant with a single amino acid change (Cys to Ser) in the conserved active pentapeptide did not exhibit detectable enzymatic activity (FIG. 4A). Immunoblotting with anti-Flag antibody revealed that extracts assayed for caspase activity expressed similar levels of caspase-8 (FIG. 4B).

EXAMPLE 4

In this example, representative data is shown that demonstrates that the CARD domain of ARC is sufficient for inhibiting apoptosis.

Figure 5B:
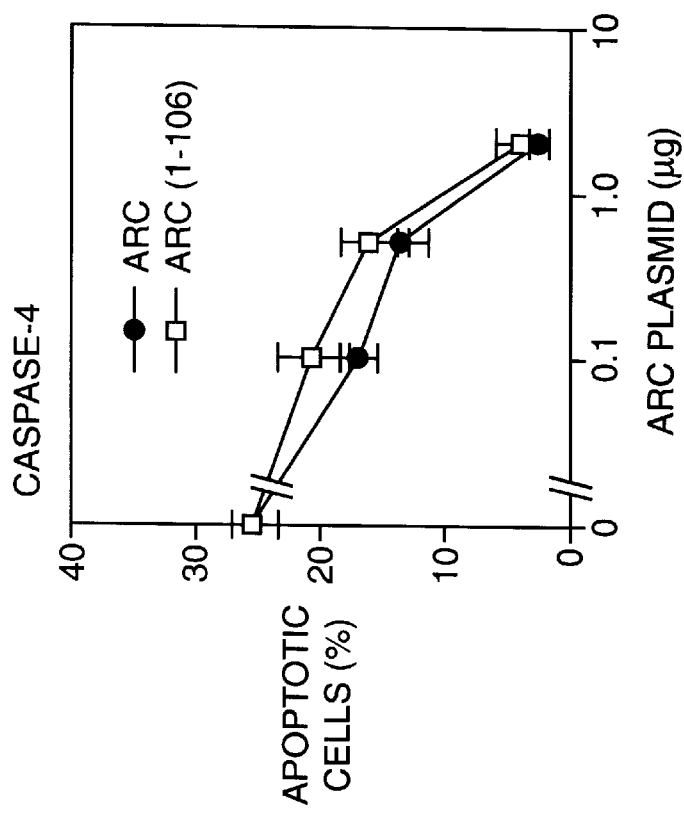
FIG. 5 show both full length and a truncated form of ARC inhibits apoptopsis to a similar extent.
FIGS. 5(A) and (B) shows the % Apoptoptic cells in transfected 293T cells. Apoptotic cells were visualized with β-galactosidase substrate and scored for morphological features of apoptosis induced by caspase-8 and caspase-4 respectively.
Figure 5A:
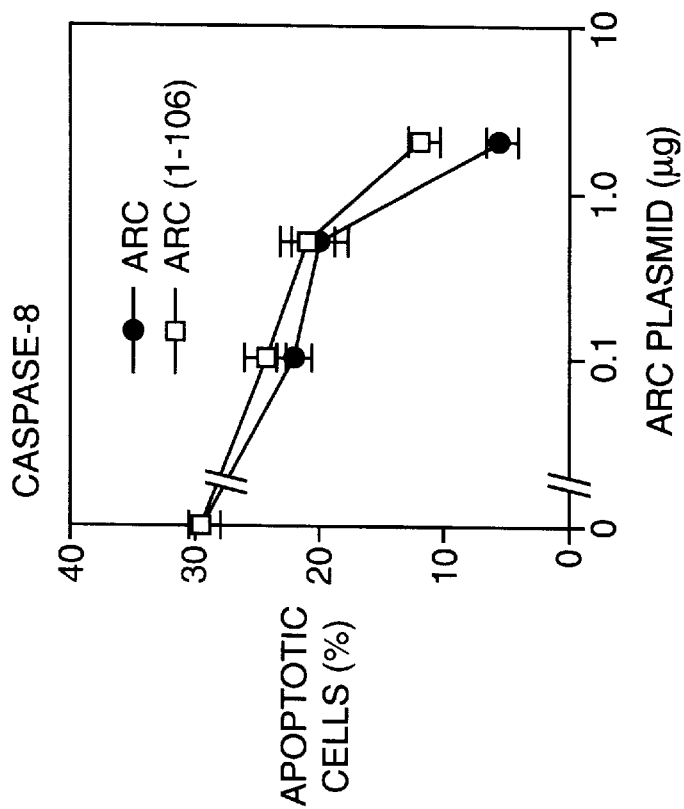

Next, comparative experiments were performed with a full length and a truncated form of ARC that expressed the CARD domain (amino acid 1–106) to suppress caspase-induced apoptosis. As shown in FIGS. 5A and 5B, there was no significant difference in the ability of the full length and the truncated forms of ARC to suppress apoptosis induced by either caspase-8 or caspase-4. This data indicated that the CARD domain was sufficient for inhibiting apoptosis.

EXAMPLE 5

Figure 6A:
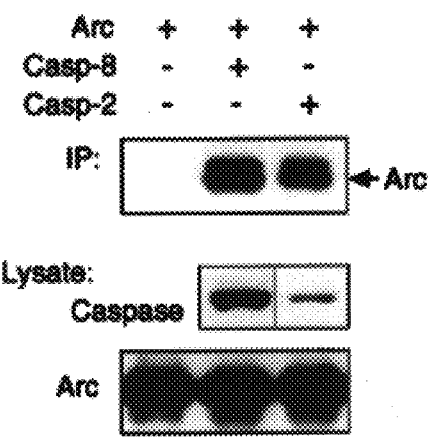
FIG. 6(A) is a representative immunoblot showing lysates of 293T cells that were transfected with plasmids AU1-tagged caspase-2 or -8 and HA-tagged ARC, that were immunoprecipitated with anti-AU1 antibody and immunoblotted with anti-HA antibody (upper panel); anti-AU1 (middle panel) or anti-HA antibody (lower panel).
Figure 6B:
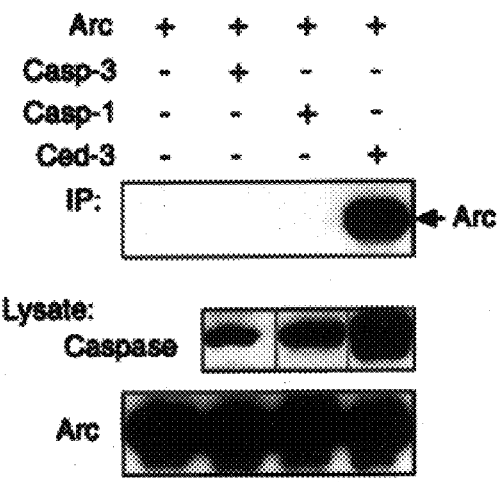
FIGS. 6(B) and (C) are representative immunoblots showing lysates of 293T cells transfected with plasmids Flag-tagged caspase-1, -3, -9 or CED-3 and HA-tagged ARC, that were immunoprecipitated with anti-Flag antibody and immunoblotted with anti-HA antibody (upper panels), anti-Flag (middle panels) or anti-HA antibody (lower panels).
Figure 6C:
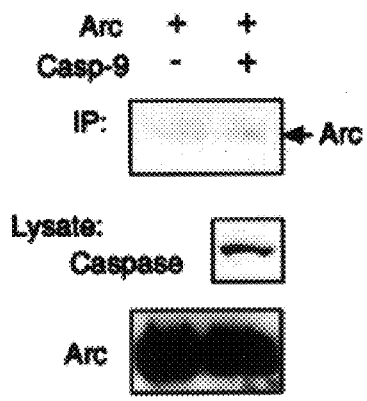
FIG. 6 shows ARC interacts with caspase-2, -8, and Ced-3 but not with caspase-1, -3, -9.
FIG. 6(D) shows lysates of 293T cells that were transfected with plasmids HA-tagged N-caspase-8 or C-caspase-8 and Flag-tagged ARC, and immunoprecipitated with anti-HA antibody and immunoblotted with anti-Flag antibody (upper panel), anti-HA (middle panel) or anti-Flag antibody (lower panel).
Figure 6D:
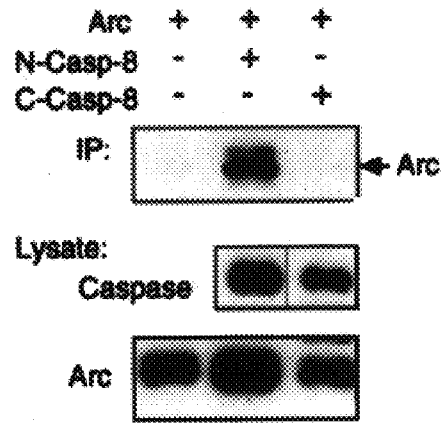

In this example, experiments are described that demonstrate ARC interacts with caspase-2, caspase-8, *C. elegans* CED-3 but not with caspase-1, caspase-3 or caspase-9. The inhibition of caspase-mediated function by ARC suggested that ARC might physically interact with caspases. To determine if ARC associates with caspases, 293T cells were transiently co-transfected with expression plasmids producing caspase-1, caspase-2, caspase-3, caspase-8, caspase-9, *C. elegans* CED-3 or control empty vector and Flag or HA tagged ARC. Immunoblotting of ARC complexes immunoprecipitated with anti-Flag antibody revealed that ARC was co-immunoprecipitated with caspase-2, caspase-8 and CED-3 but not with caspase-1, caspase-3 or caspase-9 (See FIGS. 6A–C). Analysis of total lysates by immunoblotting revealed that lack of interaction between ARC and caspase-1, caspase-3 or caspase-9 was not due to inappropriate expression of these proteins in cell extracts (See FIGS. 6B, C). Further analysis of caspase-8 deletion mutants revealed that ARC associated with the N-terminal death effector domain (DED) but not with the C-terminal region that contains the catalytic domain of caspase-8 (FIG. 6D). Furthermore, ARC did not associate with several apoptosis regulatory molecules including FADD, RAIDD, Bcl-$X_L$, and c-IAP-2 (data not shown), further supporting the specificity of the ARC interactions.

EXAMPLE 6

Figures 8A, 8B, 8C:
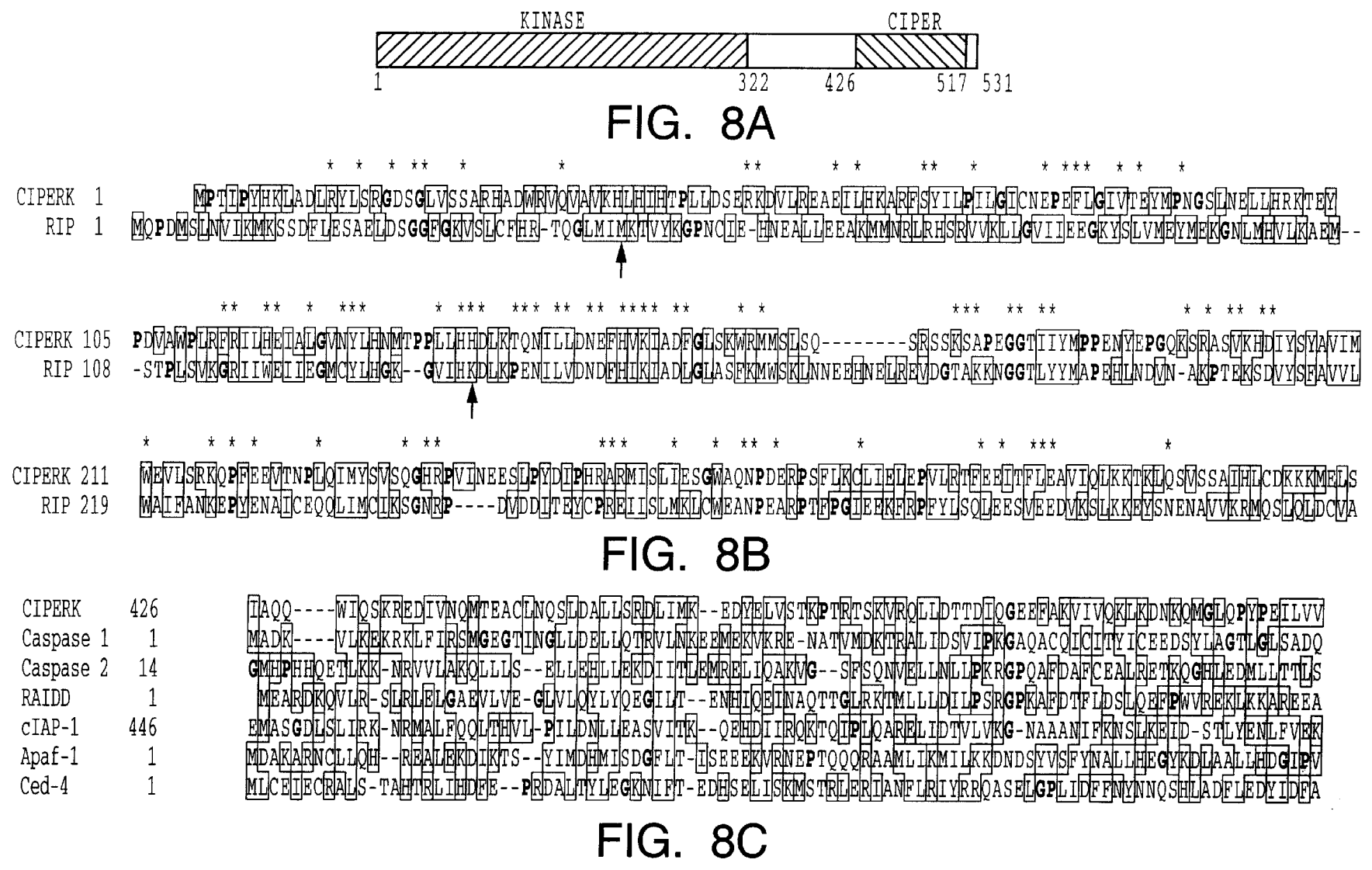

In this example, identification of RICK, a novel protein kinase containing a caspase recruitment domain is described. To identify potential RIP-related genes, public databases of expressed-sequence tags (ESTs) were searched for clones with homology to the catalytic domain of RIP. Three ESTs encoding novel overlapping peptides were identified with significant amino acid homology to the kinase domain of RIP. Sequence analysis of the three cDNAs demonstrated that the three clones represented fragments of the same gene. The longest CDNA clone had an 1.8 kb insert and an open reading frame encoding a protein of 531 amino acids with an estimated molecular size of 60,332 Da (FIG. 7). This protein has been designated as RICK (RIP-like interacting CLARP kinase). Analysis of the RICK amino acid sequence revealed that it contains an N-terminal serine-threonine kinase catalytic domain with significant amino acid similarity to the kinase catalytic domain of RIP (FIGS. 8A and 8B). Unlike RIP, the C-terminal region of RICK had significant similarity to the pro-domain of several caspases including caspase-1 and -2 (FIG. 8B). In addition, the same C-terminal fragment of RICK (residues 426–517) had significant amino acid similarity to regions from other apoptosis-regulatory proteins including RAIDD, cIAP-1, the N-terminus of Apaf-1 [H. Zou et al., Cell 90:405–413 (1997)] and its C. elegans homologue CED-4 (FIG. 8C). The region of homology between RICK and CED-3-like caspases/CED-4/Apaf-1/RAIDD/cIAP corresponds to a domain previously named caspase recruitment domain (CARD) [K. Hofmann et al., Trends. Biochem. Sci. 22:155–156 (1997)].

EXAMPLE 7

Figure 9:
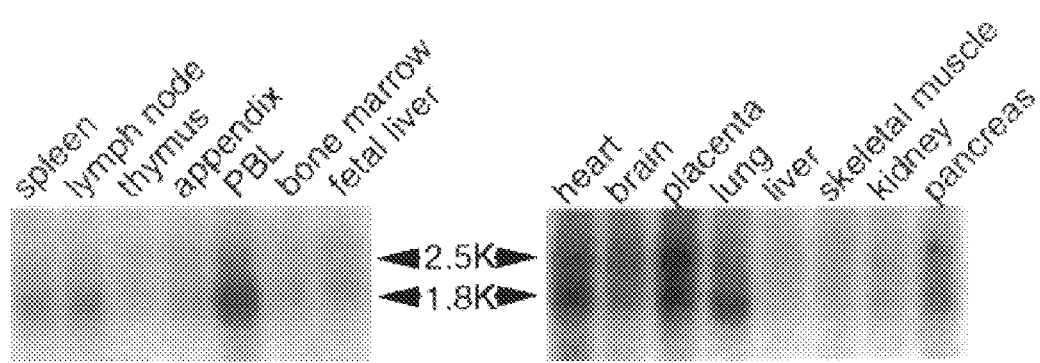
FIG. 9 is a Northern blot analysis, showing the tissue distribution of human RICK. PBL denotes peripheral blood lymphocytes.

In this example, experiments are described that demonstrate RICK is expressed in multiple human tissues. Northern blot analysis was performed to determine the distribution of RICK RNA transcripts in various human tissues. RICK was detected in heart, brain, placenta lung, pancreas, spleen, lymph node, and peripheral blood lymphocytes as two transcripts of 2.5 and 1.8 kb (FIG. 9). Further analysis revealed that the difference in RICK mRNA transcripts is due to differential polyadenylation.

EXAMPLE 8

In this example, experiments are described that demonstrate RICK potentiates apoptosis induced by caspase-8 and caspase-10. To elucidate the physiological function of RICK, expression constructs producing Flag-tagged RICK, native RICK or control proteins were introduced into 293T which were subsequently observed for features of apoptosis. Expression of caspase-8 and -10, two caspases known to be activated during CD95 signaling [M. Muzio et al., Cell 85:817–827 (1996); J. P. Medema et al., EMBO J. 16:2794 –2804 (1997); T. Fernandes-Alnemri et al., Proc. Natl. Acad Sci. USA 93:7464–7469 (1996)], induced significant apoptosis but RICK did not (FIG. 10A). Significantly, expression of RICK augmented apoptosis promoted by caspase-8 and caspase-10 (FIG. 10A). The enhancement of caspase-8-mediated apoptosis induced by RICK required a catalytic active caspase-8 since RICK did not augment the level of apoptosis induced by caspase-8-mt, a mutant caspase-8 protein with a single amino acid change (Cys377 to Ser) in the conserved active pentapeptide (FIG. 10A). Furthermore, caspase-8-induced apoptosis potentiated by RICK was inhibited by the broad-based caspase inhibitors zVAD-fmk and baculovirus p35 (FIG. 10A).

The potentiation of caspase-8-mediated apoptosis by RICK suggested that RICK could enhance the activation of caspase-8. To measure the protease activity associated with caspase-8, lysates from 293T cells co-transfected with AUI-tagged caspase-8 and Flag-tagged RICK were incubated with anti-AU1 antibody to immunoprecipitate caspase-8, and the immunoprecipitates were assayed for enzymatic activity using the Ac-DEVD-AMC (Acetyl-Asp-Glu-Val-Asp-amino-4-methylcoumarin) fluorogenic substrate [N. Inohara et al., Proc. Natl. Acad. Sci. U.S.A. 94:10717–10722 (1997)]. The analysis showed that RICK enhanced the enzymatic activity of wild-type (wt) caspase-8 but not that of caspase-8-mt (FIG. 10B). Moreover, the caspase-promoting activity induced by RICK was similar to that observed when caspase-8 was co-expressed with FADD (FIG. 10B), a protein known to activate caspase-8 [M. P. Boldin et al., Cell 85:803–815 (1996); M. Muzio et al., Cell 85:817–827 (1996)]. This example shows RICK potentiates apoptosis mediated by caspase 8 by augmenting the enzymatic activity of caspase-8.

EXAMPLE 9

In this example, experiments are described that show a RICK ATP-binding site mutant as a dominant-negative inhibitor of CD95-mediated apoptosis. The results presented in example 8 suggested that RICK could be involved in the regulation of apoptosis induced by CD95 receptor stimulation. Catalytically inactive mutants of serine threonine kinases often act as dominant negative inhibitors of the active kinase. Therefore, a mutant form of RICK (RICK-K38M) was engineered in which the lysine of the putative adenosine triphosphate (ATP)-binding site at position 38 was replaced by a methionine. To test if this mutant could regulate CD95-mediated apoptosis, expression constructs producing Flag-tagged RICK-K38M or empty vector were stably transfected into BJAB, a human B cell line that undergoes apoptosis upon CD95 stimulation [A. M. Chinnaiyan et al., Cell 81:505–512 (1995)]. To minimize clonal variation, bulk BJAB cell lines expressing RICK-K38M or control were selected with puromycin and analyzed two weeks after transfection. BJAB expressing the RICK-K3 8M mutant were significantly less sensitive to anti-APO1-induced apoptosis than BJAB cells transfected with control plasmid (FIG. 10C, p<0.001). Protein analysis revealed that BJAB transfected with RICK-K38M expressed the Flag-tagged RICK mutant protein (FIG. 10C, inset). These results indicated that the RICK-K38M mutant inhibits apoptosis induced by CD95 stimulation and suggested that RICK is involved in regulation of the CD95 signaling pathway. To confirm defective kinase function of RICK-K38M mutant, the wild type and mutant RICK proteins were expressed in 293T cells and immunoprecipitated with mAb to Flag. The K38M mutation in RICK dramatically decreased its auto-phosphorylation in vitro (FIG. 10D).

Moreover, deletion mutant forms of RICK were engineered to further characterize their abilities to regulate apoptosis (FIG. 11A). Deletion mutants of the N-terminal region spanning the catalytic kinase domain (Δ53, Δ247 and Δ364) failed to potentiate apoptosis of 293T cells induced by Fas, Fas plus FasL or caspase-8 (FIG. 11A). In addition, a deletion mutant missing the C-terminal 165 amino acids that span the CARD domain did not enhance apoptosis (FIG. 11B). Immunoblotting analysis revealed that wt and mutant forms of RICK were expressed ruling out loss of function due to inappropriate levels of expression (FIG. 11C). These results indicated that both the kinase catalytic domain and the C-terminal region containing the CARD domain are required for enhancement of apoptosis by RICK.

EXAMPLE 10

In this example, experiments are described that show RICK interacts with the C-terminal Domain of CLARP, a caspase-like protein with homology to caspase-8, and is a kinase that is involved in the regulation of apoptosis induced by the CD95 receptor pathway. The presence of the CARD domain suggested that RICK could promote apoptosis by interacting with signaling molecules of the CD95 death pathway. To test this, expression constructs producing several HA-tagged apoptosis-regulatory proteins and Flag-tagged RICK were transiently co-transfected into 293T cells. Cell lysates were immunoprecipitated with anti-Flag antibody and co-immunoprecipitated proteins were analyzed by immunoblotting with anti-HA antibody. The analysis shown in FIG. 9D revealed that RICK co-immunoprecipitated with CLARP, a caspase-related protein also known as Casper, c-FLIP$_L$, I-FLICE, FLAME-1, CASH$_L$ and MRIT that interacts with FADD and caspase-8 [N. Inohara et al., *Proc. Natl. Acad. Sci. U.S.A.* 94:10717–10722 (1997); Y. V. Goltsev et al., *J. Biol Chem.* 272:19641–19644 (1997); S. Hu et al., *J. Biol. Chem.* 272:17255–17257 (1997); M Irmler et al., *Nature* 388:190–195 (1997); H. B. Shu et al., *Immunity* 6:751–763 (1997); S. M. Srinivasula et al., *J. Biol. Chem.* 272:18542–18545 (1997); D. K. M. Han et al. *Proc. Natl. Acad. Sci. U.S.A.* 94:11333–11338 (1997)1. The interaction between CLARP and RICK was specific in that RICK did not associate with multiple apoptosis regulatory proteins including caspase-1, caspase-2, caspase-3, caspase-4, caspase-8, CED-3, CED-4, Bcl-XL, TRAF2, c-IAP-1, c-IAP-2 or RAIDD[2].

CLARP is comprised of two N-terminal DEDs fused to a C-terminal caspase-like domain [N. Inohara et al., *Proc. Natl. Acad. Sci. U.S.A.* 94:10717–10722 (1997); Y. V. Goltsev et al., *J. Biol. Chem.* 272:19641–19644 (1997); S. Hu et al., *J. Biol. Chem.* 272:17255–17257 (1997); M Irmler et al., *Nature* 388:190–195 (1997); H. B. Shu et al., *Immunity* 6:751–763 (1997); S. M. Srinivasula et al., *J. Biol. Chem.* 272:18542–18545 (1997); D. K. M. Han et al. *Proc. Natl. Acad. Sci. U.S.A.* 94:11333–11338 (1997)]. Two mutant forms of CLARP were engineered to determine the regions of CLARP required for its interaction with RICK. One mutant containing the N-terminal DED modules (CLARP-N) corresponds to c-FLIP$_s$/CASH$_s$/MRITβ1, a protein form generated by differential RNA splicing [Y. V. Goltsev et al., *J. Biol. Chem.* 272:19641–19644 (1997); M Irmler et al., *Nature* 388:190–195 (1997); D. K. M. Han et al. *Proc. Natl. Acad. Sci. U.S.A.* 94:11333–11338 (1997)], whereas the other mutant (CLARP-C) contained the C-terminal caspase-like domain (residues 246–480). RICK interacted with the C-terminal caspase-like domain but not with the N-terminal DED-containing domain of CLARP (FIG. 11D). Thus, RICK interacts with the C-terminal caspase-like domain of CLARP.

Upon activation, the CD95 receptor recruits FADD and caspase-8 into a death-inducing signaling complex (DISC) that is induced or enhanced by CD95 receptor oligomerization and activation [M. P. Boldin et al., *Cell* 85:803–815 (1996); M. Muzio et al., *Cell* 85:817–827 (1996)]. CLARP has been shown to bind to caspase-8 and FADD [N. Inohara et al., *Proc. Natl. Acad. Sci. U.S.A.* 94:10717–10722 (1997); Y. V. Goltsev et al., *J. Biol. Chem.* 272:19641–19644 (1997); S. Hu et al., *J. Biol. Chem.* 272:17255–17257 (1997); M Irmler et al., *Nature* 388:190–195 (1997); H. B. Shu et al., *Immunity* 6:751–763 (1997); S. M. Srinivasula et al., *J. Biol. Chem.* 272:18542–18545 (1997); D. K. M. Han et al. *Proc. Natl. Acad. Sci. U.S.A.* 94:11333–11338 (1997)]. Thus, CLARP could function as an adapter molecule to link RICK to proximal components of the CD95 signaling complex. RICK-K38M, a mutant in which the lysine of the putative adenosine triphosphate (ATP)-binding site at position 38 was replaced by a methionine, functioned as an inhibitor of CD95-mediated apoptosis. Identical mutations in the ATP-binding site of several serine threonine kinases lead to catalytically inactive proteins that act as dominant negative mutants. Thus, these results suggest that RICK is a kinase that is involved in the regulation of apoptosis induced by the CD95 receptor pathway.

Since, CLARP is known to interact with FADD, suggesting that CIPERK could be involved in the phosphorylation of FADD. Therefore, next it was determined whether expression of CIPERK can regulate the phosphorylation of FADD in vivo. Expression plasmids producing HA-CLARP, Flag-CIPERK and AU1-FADD were transiently transfected into 293T cells, and the expression of FADD was monitored by immunoblotting with anti-AU1 antibody. Transfection of plasmids producing either FADD or FADD plus CIPERK induced the expression of two closely migrating AU1-tagged FADD proteins of ~27 kDa (FIG. 12A). In contrast, co-expression of FADD, CIPERK and CLARP induced the expression of two additional FADD bands migrating at ~30 kDa (FIG. 12A), previously shown to represent phosphorylated FADD [B. Z. Stanger et al., *Cell* 81:513–523 (1995)]. Treatment of the FADD immunoprecipitates with recombinant calf intestinal phosphatase eliminated the upper ~30 kDa bands indicating that they represent phosphorylated FADD (FIG. 12A). The increased induction of FADD phosphorylation by CLARP was specific in that was not observed when FADD was co-expressed with only CIPERK and caspase-8 (FIG. 12A). Furthermore, FADD phosphorylation was induced by ectopic expression of CD95 (FIG. 12B), a stimulus known to induce CD95 oligomerization and activation [J. P. Medema et al., *EMBO J.* 16:2794–2804 (1997); B. Z. Stanger et al., *Cell* 81:513–523 (1995)].

Because RICK induced the phosphorylation of FADD in the presence of CLARP, it was hypothesized that FADD is a protein substrate of RICK. To determine whether RICK could phosphorylate FADD directly, recombinant FADD was purified and incubated with RICK or control immunoprecipitates from 293T cells expressing wt or mutant RICK [S. M. Srinivasula et al *J. Biol. Chem.* 272:18542–18545 (1997)]. RICK induced phosphorylation of FADD, whereas RICK-K38M, a mutant in which the lysine of the putative adenosine triphosphate (ATP)-binding site at position 38 was replaced by a methionine did not (FIG. 12C). Phosphorylation of FADD was specific in that RICK failed to phosphorylate the heavy and light chains of immunoglobulin included in the immunoprecipitate that was detected by Ponceau S staining [K. Hofmann et al., *Trends. Biochem. Sci.* 22:155–156 (1997)]. Immunoblotting analysis revealed that the amounts of wt RICK and mutant CIPER-K38M as well as recombinant FADD were equivalent (FIG. 12C). Further functional analysis was performed to assess the role of RICK in the regulation of apoptosis mediated by molecules of the CD95 signaling pathway. Expression of wt RICK enhanced apoptosis induced by FADD, CLARP and caspase-8, whereas the RICK-K38M mutant did not (FIG. 12D). These results indicate that the kinase catalytic activity is essential for the regulation of apoptosis by RICK. The C-terminal caspase-like domain of CLARP interacts with RICK, while the N-terminal domain that contains the DED modules is involved in the interaction with FADD [M. Irmler et al., *Nature* 388:190–195 (1997)]. Thus, it was proposed that CLARP can function as an adaptor molecule to link RICK with FADD and the CD95 signaling complex. Because RICK can induce the phosphorylation of FADD in vivo and in vitro, these results indicated that CLARP recruits RICK to the CD95-signaling complex where it can phosphorylate FADD. The proposed model is consistent with the observation that optimal FADD phosphorylation induced by RICK requires the expression of CLARP. Upon activation, the CD95 receptor recruits FADD and caspase-8 into a death-inducing signaling complex (DISC) that is induced or enhanced by CD95 receptor oligomerization and activation [B. Z. Stanger et al., Cell 81:513–523 (1995)]. Enhancement of CD95-induced apoptosis by RICK required a catalytically active RICK suggesting that phosphorylation induced by RICK is essential for its apoptosis-promoting function. However, more definitive assessment of the role of FADD phosphorylation on CD95-mediated apoptosis will require analysis of FADD mutants deficient in phosphorylation. The phosphorylation of FADD is likely to result in a conformation change in FADD. This could lead to increased activation of caspase-8 which is consistent with our observation that RICK increases the activity of caspase-8. Activated caspase-8 is known to trigger a cascade of caspases and rapid cell death [M. Muzio et al., Cell 85:817–827 (1996)]. TNFR1 and DR3/WSL-1 also interacts with FADD via another DED-containing adaptor molecule termed TRADD [D. K. M. Han et al., Proc. Natl. Acad. Sci. U.S.A. 94:11333–11338 (1997)]. It is possible, therefore, that TNFR1- and DR3/WSL-1-induced apoptosis is also regulated by RICK. Thus RICK may represent a common kinase involved in the regulation of apoptosis induced by several death receptors.

EXAMPLE 11

This example shows that expression of RICK in cells leads to induction of NFkB whereas co-expression of both RICK and TNFRI enhances the activation of NFkB (See FIG. 13).

EXAMPLE 12

In this example, the identification of mammalian CIDEs and Drosophila DREP-1 are described. To identify potential DFF45-related genes, EST database of GenBank was searched for clones with homology to DFF45 [X. Liu et al., "Apaf-1, a human protein homologous to C. elegans CED-4, participates in cytochrome c-dependent activation of caspase-3," Cell 90:405–413 (1997)]. Two types of mouse ESTs encoding two distinct peptides with statistically significant amino acid homology to DFF45 were identified (P<2×10$^{-3}$) by TBLASTN program. Subsequent sequence analysis revealed that the ESTs represented two different genes with open reading frames encoding highly homologous proteins of 200 and 219 amino acids (FIG. 14). These mouse genes were designated CIDE-A and CIDE-B (for cell death-inducing DFF45-like effector A and B). In addition, a human EST clone with 83% amino acid identity with mouse CIDE-A was identified and it appeared therefore to represent the human homologue of CIDE-A (FIG. 14). Analysis of the nucleotide sequence of both human and mouse CIDE-A cDNAs revealed two potential in-frame translation initiation sites separated by 51 nucleotides. These two potential initiation codons produce a protein of 217 amino acids (designated CIDE-A*) and a protein identical to CIDE-A* but lacking its 17 most N-terminal amino acids (designated CIDE-A). BLAST search revealed that CIDE-A and -B were novel molecules highly homologous to FSP27 (FIG. 14(B)), a protein of unknown function whose expression is associated with terminal differentiation of fat cells [U. Danesch et al., "Cloning and transcriptional regulation of a novel adipocyte-specific gene, FSP27. CAAT-enhancer-binding protein (C/EBP) and C/EBP-like proteins interact with sequences required for differentiation-dependent expression," J. Biol. Chem. 267:7185–7193 (1992)]. The homology of CIDE-A, CIDE-B and FSP27 with DFF45 was restricted to a N-terminal region designated here as CIDE-N domain which showed 39%, 29% and 38% amino acid identity respectively with DFF45. Another region of CIDE-A and CIDE-B, termed CIDE-C domain, located in their C-termini shared amino acid homology (54% and 53% identity, respectively) with FSP27 but not with DFF45 (FIG. 11). To determine if DFF45 related molecules are conserved in other species, the invertebrate EST database of GenBank were searched for clones with homology to DFF45. A Drosophila melanogaster gene was identified encoding a peptide with significant homology to DFF45, and was designated as DREP-1. The similarity between DREP-1 and DFF45, CIDE-A and CIDE-B was most significant at the N-termini. Significantly, The C-terminus of DREP-1 has homology to that of DFF45 but not to CIDE-A, CIDE-B and FSP27 (FIGS. 14(B) and (D)). Importantly, two aspartic acid residues known to be part of a caspase-3 recognition site in DFF45 [X. Liu et al., "Apaf-1, a human protein homologous to C. elegans CED-4, participates in cytochrome c-dependent activation of caspase-3," Cell 90:405–413 (1997)] were also conserved in Drosophila DREP-1 [FIG. 14(D)].

EXAMPLE 13

In this example, the experiments performed demonstrate differential expression of CIDE-A and -B mRNA in human tissues. By Northern blot analysis the distribution of CIDE-A and CIDE-B RNA transcripts in various human tissues was determined. Expression of CIDE-A was detected in heart and at a lower level in skeletal muscle, brain, lymph node, thymus, appendix and bone marrow as a 1.3 Kb transcript. A smaller transcript of 1.0 Kb was expressed at low levels in the placenta. In addition, another transcript of approximately 7.0 Kb was detected with the CIDE-A probe in kidney and at a lower level in heart, brain, placenta and lung (FIG. 15(A)). The expression pattern of CIDE-B was different from that of CIDE-A. Hybridization with a CIDE-B probe revealed a major transcript of 1.3 Kb in adult and fetal liver (FIG. 15(B)). In addition, another transcript of approximately 2.5 Kb was detected at lower levels in spleen, peripheral blood lymphocytes, bone marrow and fetal liver (FIG. 15(B)). CIDE-A but not CIDE-B mRNA was expressed in 293T embryonic kidney, MCF-7 breast carcinoma and SHEP neuroblastoma cells (data not shown).

EXAMPLE 14

In this example, experiments are described that show CIDE-A and -B but not DFF45 activate apoptotic cell death. To elucidate the physiological function of CIDE proteins, expression constructs producing CIDE-A, CIDE-B and DFF45 were introduced into 293T cells and subsequently observed for features of apoptosis. CIDE-A-, but not DFF45-transfected cells, displayed morphological features of adherent cells undergoing apoptosis such as becoming rounded with plasma membrane blebbing, condensed nuclei and detachment from the dish (data not shown). In addition, CIDE-A, but not DFF45, induced nuclear condensation and fragmentation, a feature characteristic of apoptosis [FIG. 16(A)]. Expression of both CIDE-A, CIDE-A*, the products of the two potential initiation codons, induced significant killing of 293T cells in a dose dependent manner as well as CIDE-B (FIG. 16(B)). In contrast, expression of DFF45 or the related-protein DREP-1 did not induce apoptosis (FIG. (16B)). In addition to 293T cells, expression of CIDE-A induced significant apoptotic cell death in MCF-7 cells as compared to control plasmid (FIG. 16(C), P<0.001). In addition, CIDE-A and CIDE-B induced apoptosis in SHEP cells (data not shown). These results were confirmed in cells transfected with plasmids expressing untagged CIDE-A*, CIDE-A, CIDE-B, DREP-1 and DFF45 indicating that the untagged and Flag-tagged proteins exhibit the same activities when transfected in cells (data not shown). Western blot analysis revealed that CIDE-A, CIDE-A*, CIDE-B, DREP-1 and DFF45 were expressed in cells, indicating that the lack of expression did not account for the inability of DFF45 to induce apoptosis (data not shown). These results indicated that CIDE-A and CIDE-B proteins, but not DFF45, induces apoptosis in mammalian cells. Thus, CIDE-A and CIDE-B exhibit non-overlapping pattern of expression in human tissues.

EXAMPLE 15

In this example, the experimental results demonstrate that CIDE-A and -B-induced apoptosis is inhibited by DFF45 and Drosophila DREP-1. To determine if DFF45 modulates the ability of CIDEs to induce cell death, the CIDE proteins were co-expressed in 293T cells and the level of apoptosis was measured. Expression of DFF45 inhibited significantly the killing activity of CIDE-A and CIDE-B (FIG. 17(A), P<0.001). Furthermore, the Drosophila DREP-1 protein also suppressed the ability of CIDE-A to induce apoptosis, further suggesting that DREP-1 is a homologue of DFF45 (FIG. 17(A), P<0.001).

EXAMPLE 16

In this example, the experimental results demonstrate expression of CIDE-A induces oligonucleosomal DNA fragmentation that is inhibited by DFF45 in 293T cells. Since, activation of DFF induces DNA fragmentation of isolated nuclei in vitro [X. Liu et al., "Apaf-1, a human protein homologous to *C. elegans* CED-4, participates in cytochrome c-dependent activation of caspase-3," *Cell* 90:405–413 (1997)], next, it was tested whether expression of CIDE-A or DFF45 could induce DNA fragmentation in 293T cells. Consistent with the results presented in FIG. 17(A), CIDE-A and caspase-8 (positive control) promoted the fragmentation of genomic DNA into oligonucleosomal fragments (FIG. 17(B)). Moreover, DNA fragmentation induced by CIDE-A was inhibited by DFF45 (FIG. 17(B)).

EXAMPLE 17

This example demonstrates apoptosis induced by CIDE-A is unaffected by caspase inhibitors zVAD-fmk, zDEVD-fmk or the cowpox protein CrmA. Next it was determined whether apoptosis activated by CIDE-A expression is caspase-dependent. In these experiments, 293T cells were transfected with constructs producing CIDE-A in the presence or absence of caspase inhibitors and the level of apoptosis in the cells was evaluated. The killing activity of CIDE-A was unaffected by the broad spectrum caspase peptide inhibitors zVAD-fmk and zDEVD-fmk or CrmA, a product of the cowpox virus that inhibits caspases (FIG. 18(A)). In control experiments, apoptosis induced by caspase-8 was inhibited by the same concentration of zVAD-fmk (FIG. 18(A)).

EXAMPLE 18

This example demonstrates apoptosis mediated by CD95/Fas is partially inhibited by DFF45. Since, an important pathway that transmits signals leading to cell death in mammals is that activated through the CD95/Fas receptor [S. Nagata, "Apoptosis by death factor," *Cell* 88:355–365 (1997)], next it was tested whether CIDE-A and DFF45 could modulate apoptosis induced by CD95/Fas signaling. As shown in FIG. 18(B), expression of CIDE-A enhanced the apoptotic activities induced by Fas signaling and CLARP, a caspase-like protein (also called CASPER/cFlip$_L$/I-FLICE/FLAME-1/CASH) that interacts with caspase-8, a component of the CD95/Fas pathway [N. Inohara et al., "CLARP, a death effector domain-containing protein interacts with caspase-8 and regulates apoptosis," *Proc. Natl. Acad. Sci. USA* 94:10717–10722 (1997a)]. In contrast, DFF45 inhibited apoptosis induced by Fas and CLARP (FIG. 18(B)).

EXAMPLE 19

This example demonstrates that the C-terminal region of CIDE-A is necessary and sufficient for killing whereas its N-terminus is required for DFF45 to inhibit CIDE-A-induced apoptosis. Two mutant forms of CIDE-A were engineered to further characterize the ability of CIDE-A to induce apoptosis. Mutant CIDE-A (1–107) contained the N-terminal half of the protein with homology to DFF45, whereas mutant CIDE-A (108–200) contained the C-terminal half (FIG. 19(A)). CIDE-A (108–200) was capable of inducing apoptosis, whereas the CIDE-A (1–107) mutant did not (FIG. 19(B)), indicating that the killing activity of CIDE-A resides in its C-terminal half. While apoptosis induced by wild-type CIDE-A was inhibited by DFF45 (FIGS. 17A and 17B), apoptosis of the CIDE-A (108–199) mutant was not inhibited by DFF45 (FIG. 19(B)) implying that the N-terminal region was required for the inhibition by DFF45. Significantly, the killing activity of the CIDE-A mutant (108–200) was greater than that elicited by wild-type CIDE-A (FIG. 19(B)), suggesting that the CIDE-A activity could be negatively regulated by endogenous proteins such as DFF45 through its N-terminal region (residues 1–107). Consistent with the latter, expression of the mutant CIDE-A (1–107) protein antagonized the inhibition of CIDE-A-induced apoptosis by DFF45 (FIG. 19(B)). Immunoblot analysis revealed that wild-type CIDE-A and mutant CIDE-A (1–107) proteins were expressed at comparable levels whereas the expression of the CIDE-A (108–200) mutant that exhibited killing activity was detected at lower levels (FIG. 19(C), lowere panel), perhaps due to the high level of apoptosis induced by the latter mutant form of CIDE-A (FIG. 19(B)). These results indicated that the C-terminus of CIDE-A is necessary and sufficient for killing while the N-terminal region with homology to DFF45 is required for DFF45 to inhibit CIDE-A-mediated apoptosis.

We claim:

1. A purified protein consisting of the sequence set out in FIG. 7A (SEQ ID NO:1).
2. The purified protein of claim 1, wherein said purified protein is bound to a substrate.
3. The purified protein of claim 2, wherein said substrate comprises caspase-like apoptosis-regulating protein.
4. The purified protein of claim 1, wherein said protein is in a complex comprising caspase-like apoptosis-regulating protein and Fas-associated death domain protein.
5. The purified protein of claim 1, wherein said protein has an amino acid substitution at position 38.

* * * * *

SEQUENCE LISTING

<160> NUMBER OF SEQ ID NOS: 38

<210> SEQ ID NO 1
<211> LENGTH: 531

```
<212> TYPE: PRT
<213> ORGANISM: Homo sapiens

<400> SEQUENCE: 1

Met Pro Thr Ile Pro Tyr His Lys Leu Ala Asp Leu Arg Tyr Leu Ser
 1               5                  10                  15

Arg Gly Ala Ser Gly Thr Val Ser Ser Ala Arg His Ala Asp Trp Arg
            20                  25                  30

Val Gln Val Ala Val Lys His Leu His Ile His Thr Pro Leu Leu Asp
        35                  40                  45

Ser Glu Arg Lys Asp Val Leu Arg Glu Ala Glu Ile Leu His Lys Ala
    50                  55                  60

Arg Phe Ser Tyr Ile Leu Pro Ile Leu Gly Ile Cys Asn Glu Pro Glu
65                  70                  75                  80

Phe Leu Gly Ile Val Thr Glu Tyr Met Pro Asn Gly Ser Leu Asn Glu
                85                  90                  95

Leu Leu His Arg Lys Thr Glu Tyr Pro Asp Val Ala Trp Pro Leu Arg
            100                 105                 110

Phe Arg Ile Leu His Glu Ile Ala Leu Gly Val Asn Tyr Leu His Asn
        115                 120                 125

Met Thr Pro Pro Leu Leu His His Asp Leu Lys Thr Gln Asn Ile Leu
    130                 135                 140

Leu Asp Asn Glu Phe His Val Lys Ile Ala Asp Phe Gly Leu Ser Lys
145                 150                 155                 160

Trp Arg Met Met Ser Leu Ser Gln Ser Arg Ser Ser Lys Ser Ala Pro
                165                 170                 175

Glu Gly Gly Thr Ile Ile Tyr Met Pro Pro Glu Asn Tyr Glu Pro Gly
            180                 185                 190

Gln Lys Ser Arg Ala Ser Ile Lys His Asp Ile Tyr Ser Tyr Ala Val
        195                 200                 205

Ile Thr Trp Glu Val Leu Ser Arg Lys Gln Pro Phe Glu Asp Val Thr
    210                 215                 220

Asn Pro Leu Gln Ile Met Tyr Ser Val Ser Gln Gly His Arg Pro Val
225                 230                 235                 240

Ile Asn Glu Glu Ser Leu Pro Tyr Asp Ile Pro His Arg Ala Arg Met
                245                 250                 255

Ile Ser Leu Ile Glu Ser Gly Trp Ala Gln Asn Pro Asp Glu Arg Pro
            260                 265                 270

Ser Phe Leu Lys Cys Leu Ile Glu Leu Glu Pro Val Leu Arg Thr Phe
        275                 280                 285

Glu Glu Ile Thr Phe Leu Glu Ala Val Ile Gln Leu Lys Lys Thr Lys
    290                 295                 300

Leu Gln Ser Val Ser Ser Ala Ile His Leu Cys Asp Lys Lys Met
305                 310                 315                 320

Glu Leu Ser Leu Asn Ile Pro Val Asn His Gly Pro Gln Glu Glu Ser
                325                 330                 335

Cys Gly Ser Ser Gln Leu His Glu Asn Ser Gly Ser Pro Glu Thr Ser
            340                 345                 350

Arg Ser Leu Pro Ala Pro Gln Asp Asn Asp Phe Leu Ser Arg Lys Ala
        355                 360                 365

Gln Asp Cys Tyr Phe Met Lys Leu His His Cys Pro Gly Asn His Ser
    370                 375                 380

Trp Asp Ser Thr Ile Ser Gly Ser Gln Arg Ala Ala Phe Cys Asp His
385                 390                 395                 400
```

-continued

```
Lys Thr Thr Pro Cys Ser Ser Ala Ile Ile Asn Pro Leu Ser Thr Ala
                405                 410                 415
Gly Asn Ser Glu Arg Leu Gln Pro Gly Ile Ala Gln Gln Trp Ile Gln
            420                 425                 430
Ser Lys Arg Glu Asp Ile Val Asn Gln Met Thr Glu Ala Cys Leu Asn
        435                 440                 445
Gln Ser Leu Asp Ala Leu Leu Ser Arg Asp Leu Ile Met Lys Glu Asp
    450                 455                 460
Tyr Glu Leu Val Ser Thr Lys Pro Thr Arg Thr Ser Lys Val Arg Gln
465                 470                 475                 480
Leu Leu Asp Thr Thr Asp Ile Gln Gly Glu Glu Phe Ala Lys Val Ile
                485                 490                 495
Val Gln Lys Leu Lys Asp Asn Lys Gln Met Gly Leu Gln Pro Tyr Pro
            500                 505                 510
Glu Ile Leu Val Val Ser Arg Ser Pro Ser Leu Asn Leu Leu Gln Asn
        515                 520                 525
Lys Ser Met
    530
```

<210> SEQ ID NO 2
<211> LENGTH: 2502
<212> TYPE: DNA
<213> ORGANISM: Homo sapiens

<400> SEQUENCE: 2

```
ggcaccagtc tctagaaaag aagtcagctc tggttcggag aagcagcggc tggcgtgggc      60
catccgggga atgggcgccc tcgtgaccta gtgttgcggg gcaaaaaggg tcttgccggc     120
ctcgctcgtg caggggcgta tctgggcgcc tgagcgcgca gtgggagcct gggagccgc      180
cgcagcaggg ggcacacccg gaaccggcct gagcgcccgg gaccatgaac ggggaggcca     240
tctgcagcgc ccatgcccac cattccctac acaaactcg ccgacctgcg ctacctgagc      300
cgcggcgcct ctggcactgt gtcgtccgcc cgccacgcag actggcgcgt ccaggtggcc     360
gtgaagcacc tgcacatcca cactccgctg ctcgacagtg aaagaaagga tgtcttaaga     420
gaagctgaaa ttttacacaa agctagattt agttacattc ttccaatttt gggaatttgc     480
aatgagcctg aatttttggg aatagttact gaatacatgc caaatggatc attaaatgaa     540
ctcctacata ggaaaactga atatcctgat gttgcttggc cattgagatt cgcatcctg      600
catgaaattg cccttggtgt aaattacctg cacaatatga ctcctccttt acttcatcat     660
gacttgaaga ctcagaatat cttattggac aatgaatttc atgttaagat tgcagatttt     720
ggtttatcaa agtggcgcat gatgtccctc tcacagtcac gaagtagcaa atctgcacca     780
gaaggaggga caattatcta tatgccacct gaaaactatg aacctggaca aaaatcaagg     840
gccagtatca agcacgatat atatagctat gcagttatca catgggaagt gttatccaga     900
aaacagcctt ttgaagatgt caccaatcct ttgcagataa tgtatagtgt gtcacaagga     960
catcgacctg ttattaatga agaaagtttg ccatatgata tacctcaccg agcacgtatg    1020
atctctctaa tagaaagtgg atgggcacaa atcccagatg aaagaccatc tttcttaaaa    1080
tgtttaatag aacttgaacc agttttgaga acatttgaag agataacttt tcttgaagct    1140
gttattcagc taaagaaaac aaagttacag agtgtttcaa gtgccattca cctatgtgac    1200
aagaagaaaa tggaattatc tctgaacata cctgtaaatc atggtccaca agaggaatca    1260
tgtggatcct ctcagctcca tgaaaatagt ggttctcctg aaacttcaag gtccctgcca    1320
```

-continued

```
gctcctcaag acaatgattt tttatctaga aaagctcaag actgttattt tatgaagctg      1380
catcactgtc ctggaaatca cagttgggat agcaccattt ctggttctca aagggctgca      1440
ttctgtgatc acaagaccac tccatgctct tcagcaataa taaatccact ctcaactgca      1500
ggaaactcag aacgtctgca gcctggtata gcccagcagt ggatccagag caaaagggaa      1560
gacattgtga accaaatgac agaagcctgc cttaaccagt cgctagatgc ccttctgtcc      1620
agggacttga tcatgaaaga ggactatgaa cttgttagta ccaagcctac aaggacctca      1680
aaagtcagac aattactaga cactactgac atccaaggag aagaatttgc caaagttata      1740
gtacaaaaat tgaaagataa caaacaaatg ggtcttcagc cttacccgga atacttgtg       1800 gtttctagat caccatcttt aaatttactt caaaataaaa gcatgtaagt gactgttttt      1860
caagaagaaa tgtgtttcat aaaaggatat ttatatctct gttgctttga cttttttttat     1920 ataaaatccg tgagtattaa agctttattg aaggttcttt gggtaaatat tagtctccct      1980
ccatgacact gcagtatttt ttttaattaa tacaagtaaa aagttgaatt tggttgaatt      2040
tgctacatag ttcaattttt atgtctcttt tgttaacaga aaccacttt aaaggatagt       2100 aattattctt gtttataaca gtgccttaag gtatgatgta tttctgatgg aagccatttt      2160
cacattcatg ttcttcatgg attatttgtt acttgtctaa gatgcaattt gattttatga      2220
agtatatacc ctttacccac cagagacagt acagaatccc tgccctaaaa tcccaggctt      2280
aattgcccta caaggggtta ttaatttaaa actccattat taggattaca ttttaaagtt      2340
ttatttatga attcccttta aaaatgatat ttcaaaggta aaacaataca atataaagaa      2400
aaaaataaat atattaatac cggcttcctg tccccatttt taacctcagc cttccctact      2460
gtcaccaaca accaagctaa ataaagtcaa cagcctgatg tg                         2502
```

<210> SEQ ID NO 3
<211> LENGTH: 530
<212> TYPE: PRT
<213> ORGANISM: Homo sapiens

<400> SEQUENCE: 3

```
Met Pro Thr Ile Pro Tyr Lys Leu Ala Asp Leu Arg Tyr Leu Ser Arg
  1               5                  10                  15

Gly Ala Ser Gly Thr Val Ser Ser Ala Arg His Ala Asp Trp Arg Val
             20                  25                  30

Gln Val Ala Val Lys Met Leu His Ile His Thr Pro Leu Leu Asp Ser
         35                  40                  45

Glu Arg Lys Asp Val Leu Arg Glu Ala Glu Ile Leu His Lys Ala Arg
     50                  55                  60

Phe Ser Tyr Ile Leu Pro Ile Leu Gly Ile Cys Asn Glu Pro Glu Phe
 65                  70                  75                  80

Leu Gly Ile Val Thr Glu Tyr Met Pro Asn Gly Ser Leu Asn Glu Leu
                 85                  90                  95

Leu His Arg Lys Thr Glu Tyr Pro Asp Val Ala Trp Pro Leu Arg Phe
            100                 105                 110

Arg Ile Leu His Glu Ile Ala Leu Gly Val Asn Tyr Leu His Asn Met
        115                 120                 125

Thr Pro Pro Leu Leu His His Asp Leu Lys Thr Gln Asn Ile Leu Leu
    130                 135                 140

Asp Asn Glu Phe His Val Lys Ile Ala Asp Phe Gly Leu Ser Lys Trp
145                 150                 155                 160
```

```
Arg Met Met Ser Leu Ser Gln Ser Arg Ser Lys Ser Ala Pro Glu
            165                 170                 175

Gly Gly Thr Ile Ile Tyr Met Pro Pro Glu Asn Tyr Glu Pro Gly Gln
            180                 185                 190

Lys Ser Arg Ala Ser Ile Lys His Asp Ile Tyr Ser Tyr Ala Val Ile
            195                 200                 205

Thr Trp Glu Val Leu Ser Arg Lys Gln Pro Phe Glu Asp Val Thr Asn
210                 215                 220

Pro Leu Gln Ile Met Tyr Ser Val Ser Gln Gly His Arg Pro Val Ile
225                 230                 235                 240

Asn Glu Glu Ser Leu Pro Tyr Asp Ile Pro His Arg Ala Arg Met Ile
            245                 250                 255

Ser Leu Ile Glu Ser Gly Trp Ala Gln Asn Pro Asp Glu Arg Pro Ser
            260                 265                 270

Phe Leu Lys Cys Leu Ile Glu Leu Glu Pro Val Leu Arg Thr Phe Glu
            275                 280                 285

Glu Ile Thr Phe Leu Glu Ala Val Ile Gln Leu Lys Lys Thr Lys Leu
            290                 295                 300

Gln Ser Val Ser Ser Ala Ile His Leu Cys Asp Lys Lys Met Glu
305                 310                 315                 320

Leu Ser Leu Asn Ile Pro Val Asn His Gly Pro Gln Glu Glu Ser Cys
            325                 330                 335

Gly Ser Ser Gln Leu His Glu Asn Ser Gly Ser Pro Glu Thr Ser Arg
            340                 345                 350

Ser Leu Pro Ala Pro Gln Asp Asn Asp Phe Leu Ser Arg Lys Ala Gln
            355                 360                 365

Asp Cys Tyr Phe Met Lys Leu His His Cys Pro Gly Asn His Ser Trp
    370                 375                 380

Asp Ser Thr Ile Ser Gly Ser Gln Arg Ala Ala Phe Cys Asp His Lys
385                 390                 395                 400

Thr Thr Pro Cys Ser Ser Ala Ile Ile Asn Pro Leu Ser Thr Ala Gly
            405                 410                 415

Asn Ser Glu Arg Leu Gln Pro Gly Ile Ala Gln Gln Trp Ile Gln Ser
            420                 425                 430

Lys Arg Glu Asp Ile Val Asn Gln Met Thr Glu Ala Cys Leu Asn Gln
            435                 440                 445

Ser Leu Asp Ala Leu Leu Ser Arg Asp Leu Ile Met Lys Glu Asp Tyr
            450                 455                 460

Glu Leu Val Ser Thr Lys Pro Thr Arg Thr Ser Lys Val Arg Gln Leu
465                 470                 475                 480

Leu Asp Thr Thr Asp Ile Gln Gly Glu Glu Phe Ala Lys Val Ile Val
            485                 490                 495

Gln Lys Leu Lys Asp Asn Lys Gln Met Gly Leu Gln Pro Tyr Pro Glu
            500                 505                 510

Ile Leu Val Val Ser Arg Ser Pro Ser Leu Asn Leu Leu Gln Asn Lys
            515                 520                 525

Ser Met
    530

<210> SEQ ID NO 4
<211> LENGTH: 478
<212> TYPE: PRT
<213> ORGANISM: Homo sapiens

<400> SEQUENCE: 4
```

-continued

```
Val Leu Arg Glu Ala Glu Ile Leu His Lys Ala Arg Phe Ser Tyr Ile
  1               5                  10                  15
Leu Pro Ile Leu Gly Ile Cys Asn Glu Pro Glu Phe Leu Gly Ile Val
             20                  25                  30
Thr Glu Tyr Met Pro Asn Gly Ser Leu Asn Glu Leu Leu His Arg Lys
         35                  40                  45
Thr Glu Tyr Pro Asp Val Ala Trp Pro Leu Arg Phe Arg Ile Leu His
     50                  55                  60
Glu Ile Ala Leu Gly Val Asn Tyr Leu His Asn Met Thr Pro Pro Leu
 65                  70                  75                  80
Leu His His Asp Leu Lys Thr Gln Asn Ile Leu Leu Asp Asn Glu Phe
                 85                  90                  95
His Val Lys Ile Ala Asp Phe Gly Leu Ser Lys Trp Arg Met Met Ser
             100                 105                 110
Leu Ser Gln Ser Arg Ser Ser Lys Ser Ala Pro Glu Gly Gly Thr Ile
             115                 120                 125
Ile Tyr Met Pro Pro Glu Asn Tyr Glu Pro Gly Gln Lys Ser Arg Ala
         130                 135                 140
Ser Ile Lys His Asp Ile Tyr Ser Tyr Ala Val Ile Thr Trp Glu Val
145                 150                 155                 160
Leu Ser Arg Lys Gln Pro Phe Glu Asp Val Thr Asn Pro Leu Gln Ile
                 165                 170                 175
Met Tyr Ser Val Ser Gln Gly His Arg Pro Val Ile Asn Glu Glu Ser
             180                 185                 190
Leu Pro Tyr Asp Ile Pro His Arg Ala Arg Met Ile Ser Leu Ile Glu
         195                 200                 205
Ser Gly Trp Ala Gln Asn Pro Asp Glu Arg Pro Ser Phe Leu Lys Cys
    210                 215                 220
Leu Ile Glu Leu Glu Pro Val Leu Arg Thr Phe Glu Glu Ile Thr Phe
225                 230                 235                 240
Leu Glu Ala Val Ile Gln Leu Lys Lys Thr Lys Leu Gln Ser Val Ser
                 245                 250                 255
Ser Ala Ile His Leu Cys Asp Lys Lys Lys Met Glu Leu Ser Leu Asn
             260                 265                 270
Ile Pro Val Asn His Gly Pro Gln Glu Glu Ser Cys Gly Ser Ser Gln
         275                 280                 285
Leu His Glu Asn Ser Gly Ser Pro Glu Thr Ser Arg Ser Leu Pro Ala
    290                 295                 300
Pro Gln Asp Asn Asp Phe Leu Ser Arg Lys Ala Gln Asp Cys Tyr Phe
305                 310                 315                 320
Met Lys Leu His His Cys Pro Gly Asn His Ser Trp Asp Ser Thr Ile
                 325                 330                 335
Ser Gly Ser Gln Arg Ala Ala Phe Cys Asp His Lys Thr Thr Pro Cys
             340                 345                 350
Ser Ser Ala Ile Ile Asn Pro Leu Ser Thr Ala Gly Asn Ser Glu Arg
         355                 360                 365
Leu Gln Pro Gly Ile Ala Gln Gln Trp Ile Gln Ser Lys Arg Glu Asp
    370                 375                 380
Ile Val Asn Gln Met Thr Glu Ala Cys Leu Asn Gln Ser Leu Asp Ala
385                 390                 395                 400
Leu Leu Ser Arg Asp Leu Ile Met Lys Glu Asp Tyr Glu Leu Val Ser
                 405                 410                 415
```

```
Thr Lys Pro Thr Arg Thr Ser Lys Val Arg Gln Leu Leu Asp Thr Thr
            420                 425                 430

Asp Ile Gln Gly Glu Glu Phe Ala Lys Val Ile Val Gln Lys Leu Lys
            435                 440                 445

Asp Asn Lys Gln Met Gly Leu Gln Pro Tyr Pro Glu Ile Leu Val Val
            450                 455                 460

Ser Arg Ser Pro Ser Leu Asn Leu Leu Gln Asn Lys Ser Met
465                 470                 475

<210> SEQ ID NO 5
<211> LENGTH: 284
<212> TYPE: PRT
<213> ORGANISM: Homo sapiens

<400> SEQUENCE: 5

Tyr Asp Ile Pro His Arg Ala Arg Met Ile Ser Leu Ile Glu Ser Gly
  1               5                  10                  15

Trp Ala Gln Asn Pro Asp Glu Arg Pro Ser Phe Leu Lys Cys Leu Ile
             20                  25                  30

Glu Leu Glu Pro Val Leu Arg Thr Phe Glu Glu Ile Thr Phe Leu Glu
         35                  40                  45

Ala Val Ile Gln Leu Lys Lys Thr Lys Leu Gln Ser Val Ser Ser Ala
     50                  55                  60

Ile His Leu Cys Asp Lys Lys Met Glu Leu Ser Leu Asn Ile Pro
 65                  70                  75                  80

Val Asn His Gly Pro Gln Glu Glu Ser Cys Gly Ser Ser Gln Leu His
                 85                  90                  95

Glu Asn Ser Gly Ser Pro Glu Thr Ser Arg Ser Leu Pro Ala Pro Gln
            100                 105                 110

Asp Asn Asp Phe Leu Ser Arg Lys Ala Gln Asp Cys Tyr Phe Met Lys
        115                 120                 125

Leu His His Cys Pro Gly Asn His Ser Trp Asp Ser Thr Ile Ser Gly
    130                 135                 140

Ser Gln Arg Ala Ala Phe Cys Asp His Lys Thr Thr Pro Cys Ser Ser
145                 150                 155                 160

Ala Ile Ile Asn Pro Leu Ser Thr Ala Gly Asn Ser Glu Arg Leu Gln
                165                 170                 175

Pro Gly Ile Ala Gln Gln Trp Ile Gln Ser Lys Arg Glu Asp Ile Val
            180                 185                 190

Asn Gln Met Thr Glu Ala Cys Leu Asn Gln Ser Leu Asp Ala Leu Leu
        195                 200                 205

Ser Arg Asp Leu Ile Met Lys Glu Asp Tyr Glu Leu Val Ser Thr Lys
    210                 215                 220

Pro Thr Arg Thr Ser Lys Val Arg Gln Leu Leu Asp Thr Thr Asp Ile
225                 230                 235                 240

Gln Gly Glu Glu Phe Ala Lys Val Ile Val Gln Lys Leu Lys Asp Asn
                245                 250                 255

Lys Gln Met Gly Leu Gln Pro Tyr Pro Glu Ile Leu Val Val Ser Arg
            260                 265                 270

Ser Pro Ser Leu Asn Leu Leu Gln Asn Lys Ser Met
        275                 280

<210> SEQ ID NO 6
<211> LENGTH: 167
<212> TYPE: PRT
```

<213> ORGANISM: Homo sapiens

<400> SEQUENCE: 6

```
Ser Arg Lys Ala Gln Asp Cys Tyr Phe Met Lys Leu His His Cys Pro
 1               5                  10                  15

Gly Asn His Ser Trp Asp Ser Thr Ile Ser Gly Ser Gln Arg Ala Ala
            20                  25                  30

Phe Cys Asp His Lys Thr Thr Pro Cys Ser Ser Ala Ile Ile Asn Pro
        35                  40                  45

Leu Ser Thr Ala Gly Asn Ser Glu Arg Leu Gln Pro Gly Ile Ala Gln
    50                  55                  60

Gln Trp Ile Gln Ser Lys Arg Glu Asp Ile Val Asn Gln Met Thr Glu
65                  70                  75                  80

Ala Cys Leu Asn Gln Ser Leu Asp Ala Leu Leu Ser Arg Asp Leu Ile
                85                  90                  95

Met Lys Glu Asp Tyr Glu Leu Val Ser Thr Lys Pro Thr Arg Thr Ser
            100                 105                 110

Lys Val Arg Gln Leu Leu Asp Thr Thr Asp Ile Gln Gly Glu Glu Phe
        115                 120                 125

Ala Lys Val Ile Val Gln Lys Leu Lys Asp Asn Lys Gln Met Gly Leu
    130                 135                 140

Gln Pro Tyr Pro Glu Ile Leu Val Val Ser Arg Ser Pro Ser Leu Asn
145                 150                 155                 160

Leu Leu Gln Asn Lys Ser Met
                165
```

<210> SEQ ID NO 7
<211> LENGTH: 264
<212> TYPE: PRT
<213> ORGANISM: Homo sapiens

<400> SEQUENCE: 7

```
Met Pro Thr Ile Pro Tyr Lys Leu Ala Asp Leu Arg Tyr Leu Ser Arg
 1               5                  10                  15

Gly Ala Ser Gly Thr Val Ser Ser Ala Arg His Ala Asp Trp Arg Val
            20                  25                  30

Gln Val Ala Val Lys His Leu His Ile His Thr Pro Leu Leu Asp Ser
        35                  40                  45

Glu Arg Lys Asp Val Leu Arg Glu Ala Glu Ile Leu His Lys Ala Arg
    50                  55                  60

Phe Ser Tyr Ile Leu Pro Ile Leu Gly Ile Cys Asn Glu Pro Glu Phe
65                  70                  75                  80

Leu Gly Ile Val Thr Glu Tyr Met Pro Asn Gly Ser Leu Asn Glu Leu
                85                  90                  95

Leu His Arg Lys Thr Glu Tyr Pro Asp Val Ala Trp Pro Leu Arg Phe
            100                 105                 110

Arg Ile Leu His Glu Ile Ala Leu Gly Val Asn Tyr Leu His Asn Met
        115                 120                 125

Thr Pro Pro Leu Leu His His Asp Leu Lys Thr Gln Asn Ile Leu Leu
    130                 135                 140

Asp Asn Glu Phe His Val Lys Ile Ala Asp Phe Gly Leu Ser Lys Trp
145                 150                 155                 160

Arg Met Met Ser Leu Ser Gln Ser Arg Ser Ser Lys Ser Ala Pro Glu
                165                 170                 175

Gly Gly Thr Ile Ile Tyr Met Pro Pro Glu Asn Tyr Glu Pro Gly Gln
```

-continued

```
            180                 185                 190
Lys Ser Arg Ala Ser Ile Lys His Asp Ile Tyr Ser Tyr Ala Val Ile
        195                 200                 205

Thr Trp Glu Val Leu Ser Arg Lys Gln Pro Phe Glu Asp Val Thr Asn
        210                 215                 220

Pro Leu Gln Ile Met Tyr Ser Val Ser Gln Gly His Arg Pro Val Ile
225                 230                 235                 240

Asn Glu Glu Ser Leu Pro Tyr Asp Ile Pro His Arg Ala Arg Met Ile
                245                 250                 255

Ser Leu Ile Glu Ser Gly Trp Ala
                260
```

<210> SEQ ID NO 8
<211> LENGTH: 208
<212> TYPE: PRT
<213> ORGANISM: Homo sapiens

<400> SEQUENCE: 8

```
Met Gly Asn Ala Gln Glu Arg Pro Ser Glu Thr Ile Asp Arg Glu Arg
1               5                   10                  15

Lys Arg Leu Val Glu Thr Leu Gln Ala Asp Ser Gly Leu Leu Leu Asp
            20                  25                  30

Ala Leu Leu Ala Arg Gly Val Leu Thr Gly Pro Glu Tyr Glu Ala Leu
        35                  40                  45

Asp Ala Leu Pro Asp Ala Glu Arg Arg Val Arg Arg Leu Leu Leu Leu
    50                  55                  60

Val Gln Gly Lys Gly Glu Ala Ala Cys Gln Glu Leu Leu Arg Cys Ala
65                  70                  75                  80

Gln Arg Thr Ala Gly Ala Pro Asp Pro Ala Trp Asp Trp Gln His Val
                85                  90                  95

Gly Pro Gly Tyr Arg Asp Arg Ser Tyr Asp Pro Pro Cys Pro Gly His
            100                 105                 110

Trp Thr Pro Glu Ala Pro Gly Ser Gly Thr Thr Cys Pro Gly Leu Pro
        115                 120                 125

Arg Ala Ser Asp Pro Asp Glu Ala Gly Gly Pro Glu Gly Ser Glu Ala
    130                 135                 140

Val Gln Ser Gly Thr Pro Glu Glu Pro Glu Pro Glu Leu Glu Ala Glu
145                 150                 155                 160

Ala Ser Lys Glu Ala Glu Pro Glu Pro Glu Pro Glu Pro Glu Leu Glu
                165                 170                 175

Pro Glu Ala Glu Ala Glu Pro Glu Pro Glu Leu Glu Pro Glu Pro Asp
            180                 185                 190

Pro Glu Pro Glu Pro Asp Phe Glu Glu Arg Asp Glu Ser Glu Asp Ser
        195                 200                 205
```

<210> SEQ ID NO 9
<211> LENGTH: 940
<212> TYPE: DNA
<213> ORGANISM: Homo sapiens

<400> SEQUENCE: 9

```
agcctgagga ggagacagga cagagcgtct ggaactgcag gaggacaccg agttccccgt    60
gttggcctcc aggtcctgtg cttgcggagc cgtccggcgg ctgggatcga gccccgacaa   120
tgggcaacgc gcaggagcgg ccgtcagaga ctatcgaccg cgagcggaaa cgcctggtcg   180
agacgctgca ggcggactcg ggactgctgt tggacgcgct gctggcgcgg ggcgtgctca   240
```

```
ccgggccaga gtacgaggca ttggatgcac tgcctgatgc cgagcgcagg gtgcgccgcc      300
tactgctgct ggtgcagggc aagggcgagg ccgcctgcca ggagctgcta cgctgtgccc      360
agcgtaccgc gggcgcgccg gaccccgctt gggactggca gcacgtgggt ccgggctacc      420
gggaccgcag ctatgaccct ccatgcccag ccactggacg ccggaggca cccggctcgg       480 ggaccacatg ccccggggttg cccagagctt cagaccctga cgaggcgggg ggccctgagg     540
gctccgaggc ggtgcaatcc gggaccccgg aggagccaga gccagagctg aagctgagg      600 cctctaaaga ggctgaaccg gagccggagc cagagccaga gctggaaccc gaggctgaag     660
cagaaccaga gccggaactg gagccagaac cggacccaga gcccgagccc gacttcgagg    720
aaagggacga gtccgaagat tcctgaaggc cagagctctt gacaggcggt gccccgccca    780
tgctggatag gacctgggat gctgctggag ctgaatcgga tgccaccaag gctcggtcca    840
gcccagtacc gctggaagtg aataaactcc ggagggtcgg acgggacctg ggctctctcc    900
aaaaaaaaaa aaaaaaaaaa aaaaaaaaaa aaaaaaaaaa                           940
```

<210> SEQ ID NO 10
<211> LENGTH: 106
<212> TYPE: PRT
<213> ORGANISM: Homo sapiens

<400> SEQUENCE: 10

```
Met Gly Asn Ala Gln Glu Arg Pro Ser Glu Thr Ile Asp Arg Glu Arg
  1               5                  10                  15

Lys Arg Leu Val Glu Thr Leu Gln Ala Asp Ser Gly Leu Leu Leu Asp
             20                  25                  30

Ala Leu Leu Ala Arg Gly Val Leu Thr Gly Pro Glu Tyr Glu Ala Leu
         35                  40                  45

Asp Ala Leu Pro Asp Ala Glu Arg Arg Val Arg Arg Leu Leu Leu Leu
     50                  55                  60

Val Gln Gly Lys Gly Glu Ala Ala Cys Gln Glu Leu Leu Arg Cys Ala
 65                  70                  75                  80

Gln Arg Thr Ala Gly Ala Pro Asp Pro Ala Trp Asp Trp Gln His Val
                 85                  90                  95

Gly Pro Gly Tyr Arg Asp Arg Ser Tyr Asp
                100                 105
```

<210> SEQ ID NO 11
<211> LENGTH: 102
<212> TYPE: PRT
<213> ORGANISM: Homo sapiens

<400> SEQUENCE: 11

```
Pro Pro Cys Pro Gly His Trp Thr Pro Glu Ala Pro Gly Ser Gly Thr
  1               5                  10                  15

Thr Cys Pro Gly Leu Pro Arg Ala Ser Asp Pro Asp Glu Ala Gly Gly
             20                  25                  30

Pro Glu Gly Ser Glu Ala Val Gln Ser Gly Thr Pro Glu Pro Glu
         35                  40                  45

Pro Glu Leu Glu Ala Glu Ala Ser Lys Glu Ala Glu Pro Glu Pro Glu
     50                  55                  60

Pro Glu Pro Glu Leu Glu Pro Glu Ala Glu Ala Glu Pro Glu Pro Glu
 65                  70                  75                  80

Leu Glu Pro Glu Pro Asp Pro Glu Pro Glu Pro Asp Phe Glu Glu Arg
                 85                  90                  95
```

Asp Glu Ser Glu Asp Ser
            100

<210> SEQ ID NO 12
<211> LENGTH: 219
<212> TYPE: PRT
<213> ORGANISM: Homo sapiens

<400> SEQUENCE: 12

Met Glu Ala Ala Arg Asp Tyr Ala Gly Ala Leu Ile Arg Pro Leu Thr
 1               5                  10                  15

Phe Met Gly Ser Gln Thr Lys Arg Val Leu Phe Thr Pro Leu Met His
            20                  25                  30

Pro Ala Arg Pro Phe Arg Val Ser Asn His Asp Arg Ser Ser Arg Arg
        35                  40                  45

Gly Val Met Ala Ser Ser Leu Gln Glu Leu Ile Ser Lys Thr Leu Asp
    50                  55                  60

Ala Leu Val Ile Ala Thr Gly Leu Val Thr Leu Val Leu Glu Glu Asp
65                  70                  75                  80

Gly Thr Val Val Asp Thr Glu Glu Phe Phe Gln Thr Leu Gly Asp Asn
                85                  90                  95

Thr His Phe Met Ile Leu Glu Lys Gly Gln Lys Trp Met Pro Gly Ser
            100                 105                 110

Gln His Val Pro Thr Cys Ser Pro Pro Lys Arg Ser Gly Ile Ala Arg
        115                 120                 125

Val Thr Phe Asp Leu Tyr Arg Leu Asn Pro Lys Asp Phe Ile Gly Cys
    130                 135                 140

Leu Asn Val Lys Ala Thr Met Tyr Glu Met Tyr Ser Val Ser Tyr Asp
145                 150                 155                 160

Ile Arg Cys Thr Gly Leu Lys Gly Leu Leu Arg Ser Leu Leu Arg Phe
                165                 170                 175

Leu Ser Tyr Ser Ala Gln Val Thr Gly Gln Phe Leu Ile Tyr Leu Gly
            180                 185                 190

Thr Tyr Met Leu Arg Val Leu Asp Asp Lys Glu Glu Arg Pro Ser Leu
        195                 200                 205

Arg Ser Gln Ala Lys Gly Arg Phe Thr Cys Gly
    210                 215

<210> SEQ ID NO 13
<211> LENGTH: 1049
<212> TYPE: DNA
<213> ORGANISM: Homo sapiens

<400> SEQUENCE: 13
ggccgccgca ctttaagagg ctgtgcaggc agacagacct ccaggcccgc tagggatcc    60 gcgccatgga ggccgcccgg gactatgcag gagccctcat caggcccctg acatttatgg   120
gatcacagac taagcgagtc ctgttcaccc cgctcatgca tccagctcgc cctttccggg   180
tctccaacca tgacaggagc agccggcgtg gggtgatggc aagcagcctg caggagctca   240
tcagcaagac tctggatgcc ctcgtcatcg ctaccggact ggtcactctg gtgctggagg   300
aagatggcac cgtggtggac acagaagagt tctttcagac cttgggagac aacacgcatt   360
tcatgatctt ggaaaaagga cagaagtgga tgccgggcag ccagcacgtc cccacttgct   420
cgccgccgaa gaggtcggga atagcgagag tcaccttcga cttgtacagg ctgaacccca   480
aggacttcat cggctgcctt aacgtgaagg ccaccatgta tgagatgtac tccgtgtcct   540

-continued

```
acgacatccg gtgcacggga ctcaagggcc tgctgaggag tctgctgcgg ttcctgtcct    600
actccgccca ggtgacggga cagtttctca tctatctggg cacatacatg ctccgggtgc    660
tggatgacaa ggaagagcgg ccatccctcc ggtcacaagc caagggcagg ttcacgtgtg    720
gatagggatg caggctgtcg ccggctcttg agccaaacac tgtgtttcgt ttggctcaat    780
gacgaatgtt gaagatgctt ttatgttctg agccacatgc acttggaggc cgctggtcac    840
gctgctcagg agtggtgccc agaaaaggaa agggcttggt ggtacatgaa gtgggggcaa    900
gtgggcaggg tgccctgggg gggaggcata gagggccctg ggggtcatgg gaagcgnacn    960
cgcagcaggc gtgcccagga gcgtgtgcat gtgtcagagc catttggtcc atcatctcct   1020
gcaataaacc catcgcaaga atgaccttc                                    1049
```

<210> SEQ ID NO 14
<211> LENGTH: 107
<212> TYPE: PRT
<213> ORGANISM: Homo sapiens

<400> SEQUENCE: 14

```
Met Glu Ala Ala Arg Asp Tyr Ala Gly Ala Leu Ile Arg Pro Leu Thr
 1               5                  10                  15

Phe Met Gly Ser Gln Thr Lys Arg Val Leu Phe Thr Pro Leu Met His
            20                  25                  30

Pro Ala Arg Pro Phe Arg Val Ser Asn His Asp Arg Ser Ser Arg Arg
        35                  40                  45

Gly Val Met Ala Ser Ser Leu Gln Glu Leu Ile Ser Lys Thr Leu Asp
    50                  55                  60

Ala Leu Val Ile Ala Thr Gly Leu Val Thr Leu Val Leu Glu Glu Asp
65                  70                  75                  80

Gly Thr Val Val Asp Thr Glu Glu Phe Phe Gln Thr Leu Gly Asp Asn
                85                  90                  95

Thr His Phe Met Ile Leu Glu Lys Gly Gln Lys
            100                 105
```

<210> SEQ ID NO 15
<211> LENGTH: 93
<212> TYPE: PRT
<213> ORGANISM: Homo sapiens

<400> SEQUENCE: 15

```
Trp Met Pro Gly Ser Gln His Val Pro Thr Cys Ser Pro Pro Lys Arg
 1               5                  10                  15

Ser Gly Ile Ala Arg Val Thr Phe Asp Leu Tyr Arg Leu Asn Pro Lys
            20                  25                  30

Asp Phe Ile Gly Cys Leu Asn Val Lys Ala Thr Met Tyr Glu Met Tyr
        35                  40                  45

Ser Val Ser Tyr Asp Ile Arg Cys Thr Gly Leu Lys Gly Leu Leu Arg
    50                  55                  60

Ser Leu Leu Arg Phe Leu Ser Tyr Ser Ala Gln Val Thr Gly Gln Phe
65                  70                  75                  80

Leu Ile Tyr Leu Gly Thr Tyr Met Leu Arg Val Leu Asp
                85                  90
```

<210> SEQ ID NO 16
<211> LENGTH: 217
<212> TYPE: PRT
<213> ORGANISM: Mus musculus

<400> SEQUENCE: 16

| | | | | | | | | | | | | | | | |
|---|---|---|---|---|---|---|---|---|---|---|---|---|---|---|---|
|Met|Glu|Thr|Ala|Arg|Asp|Tyr|Ala|Gly|Ala|Leu|Ile|Arg|Pro|Leu|Thr|
|1| | | |5| | | | |10| | | | |15| |

Phe Met Gly Leu Gln Thr Lys Lys Val Leu Leu Thr Pro Leu Ile His
                  20                  25                30

Pro Ala Arg Pro Phe Arg Val Ser Asn His Asp Arg Ser Ser Arg Arg
        35                  40                        45

Gly Val Met Ala Ser Ser Leu Gln Glu Leu Ile Ser Lys Thr Leu Asp
 50                  55                      60

Val Leu Val Ile Thr Thr Gly Leu Val Thr Leu Val Leu Glu Glu Asp
65               70                 75              80

Gly Thr Val Val Asp Thr Glu Glu Phe Phe Gln Thr Leu Arg Asp Asn
              85                  90               95

Thr His Phe Met Ile Leu Glu Lys Gly Gln Lys Trp Thr Pro Gly Ser
            100                  105              110

Lys Tyr Val Pro Val Cys Lys Gln Pro Lys Lys Ser Gly Ile Ala Arg
        115                  120                  125

Val Thr Phe Asp Leu Tyr Arg Leu Asn Pro Lys Asp Phe Leu Gly Cys
     130                  135                  140

Leu Asn Val Lys Ala Thr Met Tyr Glu Met Tyr Ser Val Ser Tyr Asp
145              150                155              160

Ile Arg Cys Thr Arg Phe Lys Ala Val Leu Arg Asn Leu Leu Arg Phe
            165                  170              175

Met Ser Tyr Ala Ala Gln Met Thr Gly Gln Phe Leu Val Tyr Ala Gly
        180                  185              190

Thr Tyr Met Leu Arg Val Leu Gly Asp Thr Glu Glu Gln Pro Ser Pro
     195                  200              205

Lys Pro Ser Thr Lys Gly Trp Phe Met
    210                  215

<210> SEQ ID NO 17
<211> LENGTH: 1114
<212> TYPE: DNA
<213> ORGANISM: Mus musculus

<400> SEQUENCE: 17

| | | | | |
|---|---|---|---|---|
|gattcggcat gaggccaaat cctgggtttt tgggccctcg gtaccgtttg cgcacgaagg|60|
|ggcgtgtgcg acggacccag gccagggagc cagaactatt cgctgctcgc aggagcgcac|120|
|gctgtcgcca aggtcgggtc aagtcgtcgc ggggcgtggc tgatagggca gtgatttaag|180|
|agacgcggct ttgggacagg aggacccgca ccaatggaga ccgccaggga ctacgcggga|240|
|gccctcatca ggcccctgac attcatggga ttgcagacta agaaggtcct actgacccca|300|
|ctcatacatc cagctcgccc ttttcgagtt tcaaaccatg accgaagtag ccggcgtggg|360|
|gtgatggcca gcagcctgca ggaacttatc agcaagactc tggatgtctt agtcatcaca|420|
|actggcctgg ttacgctggt gctggaggag acggcaccg tggtgacac agaggagttc|480|
|tttcagacct taagggacaa cacgcatttc atgatcttgg aaaagggaca gaaatggaca|540|
|ccgggtagta agtatgtccc agtctgcaag caaccaaaga atcgggaat agccagagtc|600|
|accttcgacc tatacaggct gaaccccaag gacttcctcg gctgtctcaa tgtcaaagcc|660|
|acgatgtacg agatgtactc ggtgtcctac gacatccgat gcaccaggtt caaggccgtg|720|
|ttaaggaatc tgctgaggtt tatgtcctat gctgcacaga tgacgggaca gttcctggtc|780|

```
tatgcgggca catacatgct ccgagtactg ggcgatacag aagagcagcc atcccccaag    840
cctagcacca aaggctggtt catgtaacca gggcacagct acagaggccc agggaccctg    900
ctctctgtta taggctgtgg gatgccaggg gaaggaatgg gggtggtacc cagtgcaggg    960
ctgagtagca ggattcctgc aaaggaaagg cggcagaggg gcctttcaag cgctttagga   1020
agggatcaac agcggagtgt gtgggaactg cgtggatacg aatcagtttc tttggatcct   1080
tacatactgt aataaaccag tcacatgagt cgtc                                1114
```

<210> SEQ ID NO 18
<211> LENGTH: 219
<212> TYPE: PRT
<213> ORGANISM: Mus musculus

<400> SEQUENCE: 18

```
Met Glu Tyr Leu Ser Ala Phe Asn Pro Asn Gly Leu Leu Arg Ser Val
  1               5                  10                  15

Ser Thr Val Ser Ser Glu Leu Ser Arg Arg Val Trp Asn Ser Ala Pro
             20                  25                  30

Pro Pro Gln Arg Pro Phe Arg Val Cys Asp His Lys Arg Thr Val Arg
         35                  40                  45

Lys Gly Leu Thr Ala Ala Ser Leu Gln Glu Leu Leu Asp Lys Val Leu
     50                  55                  60

Glu Thr Leu Leu Leu Arg Gly Val Leu Thr Leu Val Leu Glu Glu Asp
 65                  70                  75                  80

Gly Thr Ala Val Asp Ser Glu Asp Phe Phe Gln Leu Leu Glu Asp Asp
                 85                  90                  95

Thr Cys Leu Met Val Leu Glu Gln Gly Gln Ser Trp Ser Pro Lys Ser
            100                 105                 110

Gly Met Leu Ser Tyr Gly Leu Gly Arg Glu Lys Pro Lys His Ser Lys
        115                 120                 125

Asp Ile Ala Arg Ile Thr Phe Asp Val Tyr Lys Gln Asn Pro Arg Asp
    130                 135                 140

Leu Phe Gly Ser Leu Asn Val Lys Ala Thr Phe Tyr Gly Leu Tyr Ser
145                 150                 155                 160

Met Ser Cys Asp Phe Gln Gly Val Gly Pro Lys Arg Val Leu Arg Glu
                165                 170                 175

Leu Leu Arg Gly Thr Ser Ser Gln Leu Gln Gly Leu Gly His Met Leu
            180                 185                 190

Leu Gly Ile Ser Ser Thr Leu Arg His Val Val Glu Gly Ala Asp Arg
        195                 200                 205

Trp Gln Trp His Gly Gln Arg His Leu His Ser
    210                 215
```

<210> SEQ ID NO 19
<211> LENGTH: 1167
<212> TYPE: DNA
<213> ORGANISM: Mus musculus

<400> SEQUENCE: 19

```
attcggatcc atgcacttta ccagggctaa gatctcagct ttatacaaaa aagcaagaac     60
aacagagaag cacccagccc caaagcaaca gggagagagt cacctccccc atccctctgc    120
atggagtacc tttcagcctt caacccaat ggcctgctaa ggtcagtatc cactgtgagc    180
tcggagttaa gccgtagggt ctggaactca gctcctccac ctcagcgacc cttccgtgtc    240
tgtgatcata agcggacagt ccggaaagga ctgacagctg ccagcctcca agaactgcta    300
```

-continued

```
gataaggtcc tggagacctt gctgctacgt ggagtgctaa cactggtcct ggaggaggat      360
gggactgctg tggacagtga ggacttcttc cagctgctgg aggacgacac gtgcttgatg      420
gtgcttgagc agggccagag ctggagcccc aagagtggga tgttgtcata cggcctagga      480
cgggagaagc caaaacacag caaggacatc gcccgcatca ccttcgatgt gtacaagcaa      540
aatccccgag acctctttgg cagcctcaac gtgaaagcaa cattctatgg actctactcc      600
atgagctgtg atttccaagg agttggccct aaaagagtac tcagggagct cctccgtggg      660
acttcctcgc agctgcaagg cctgggccat atgctgctgg catctcctc cacccttcgc       720
catgtggtgg aggggctga tcgatggcag tggcacgggc agagacacct ccactcctaa       780
tgagatcatg ctttgagcct gtgctgaaag actggttcca tgtgacacag agggtagta      840
aaggcaccat caggcttggg gtctgcagtg tacctaggta accaagctga ctccatccta      900
acagatgtgc acactgcctt gttcctctgg cctgtacatc ttcctgaaga atgctacctg      960
tcttccctcc actcctgcct tccacatacc ctgcagaacc acagccttgt cccctgcatc     1020
ctgatcccac cgtaatcgct gcttcatata ggttttttact gacgcctacc cctaagatcc    1080
tgcataccaa cggccactgt ccctagcttt actacaagaa aactttcccc taaaaaataa     1140
aataaaaata tttccaagaa aaataaa                                         1167
```

<210> SEQ ID NO 20
<211> LENGTH: 299
<212> TYPE: PRT
<213> ORGANISM: Drosophila melanogaster

<400> SEQUENCE: 20

```
Met Glu Thr Ala Ala Asn Ser Gly Asp Ser Lys Lys Pro Phe Lys Val
  1               5                  10                  15

Lys Asp Val Thr Arg Asn Ile Lys Lys Ala Val Cys Ala Ser Ser Leu
             20                  25                  30

Glu Glu Ile Arg Ser Lys Val Ala Glu Lys Phe Glu Lys Cys Asp His
         35                  40                  45

Leu Pro Thr Ile His Leu Asp Ser Asp Gly Thr Glu Ile Asp Asp Glu
     50                  55                  60

Glu Tyr Phe Arg Thr Leu Asp Glu Asn Thr Glu Leu Val Ala Val Phe
 65                  70                  75                  80

Pro Gly Glu His Trp Ile Asp Pro Thr His Tyr Val Thr Ile Thr Thr
                 85                  90                  95

Pro His Gly Asn Glu Ala Gly Thr Gly Asn Gly Glu Leu Asn Gly Gly
            100                 105                 110

Gly Glu Gly Asp Thr Thr Asp Ala Asn Asn Ser Glu Ser Ala Arg Ile
        115                 120                 125

Arg Gln Leu Val Gly Gln Leu Gln Asn Asn Leu Cys Asn Val Ser Val
    130                 135                 140

Met Asn Asp Ala Asp Leu Asp Ser Leu Ser Asn Met Asp Pro Asn Ser
145                 150                 155                 160

Leu Val Asp Ile Thr Gly Lys Glu Phe Met Glu Gln Leu Lys Asp Ala
                165                 170                 175

Gly Arg Pro Leu Cys Ala Lys Arg Asn Ala Glu Asp Arg Leu Asn Leu
            180                 185                 190

Leu Lys Leu Lys Leu Leu Lys Ala Gly Ala Ile Phe Cys Ser Glu Arg
        195                 200                 205

Tyr Pro Glu Asp Ala Glu Ala Ile Asp Arg Glu Ile Gly Arg Gln Leu
```

```
                     210                 215                 220
Asn Glu Ala Glu Ser Gly Gln Met Ser Thr Thr Thr Ser Asn Thr
225                 230                 235                 240

Arg Thr Ile Glu Val Val Gln Cys Asp Asn Gln Asn Thr Thr Ile Thr
                245                 250                 255

Ile Thr Val Gly Glu Ala Thr Thr Thr Cys Ala Thr Ala Ser Gly Ala
            260                 265                 270

Met Gly Ser Ser Ala Ala Glu Ala Ala Ala Asn Glu Ala Asn Ala Asn
        275                 280                 285

Pro Asn Arg Asn Pro Asn Ala Asn Gly Asp Ile
    290                 295
```

<210> SEQ ID NO 21
<211> LENGTH: 2143
<212> TYPE: DNA
<213> ORGANISM: Drosophila melanogaster

<400> SEQUENCE: 21

```
ccggtgctca tcgcaacgaa agctccgctg cggacgcgag aaaatattgt taattcccat    60
ttgaagtgca gcttgtggaa ggaaattcca gtttgtttg ttcggacgcc gagtgcaagt   120
gcaagaagca agcgaaaagt aatcaaatct atagaaaagt catttaatgt ggagcaatta   180
agcctggaaa taaagtgcat agtgaataag taatttagtt ggagcaaaca aagccatgga   240
gactgcagcg aactcgggcg actccaaaaa gcctttcaaa gtcaaggacg taacacgcaa   300
cattaagaag gctgtctgcg cctccagtct ggaggagatc cgcagcaagg tggcggagaa   360
gttcgagaag tgcgaccacc tgcccaccat ccacctggac tccgacggca cggagatcga   420
tgatgaggag tactttcgca ccctcgacga gaatacggaa ctggtggccg tctttcccgg   480
agaacattgg atcgatccca ctcactacgt gacgataacc actccacatg caacgaggc   540
aggaactgga acggagagc tgaacggagg aggcgagggc gacaccaccg atgccaacaa   600
ctcggagtcg gctcgcatcc gccagttggt gggccagctg cagaacaacc tctgcaacgt   660
gtccgtgatg aacgatgccg atctggactc actctccaac atggatccca actcgttggt   720
ggacatcacg ggaaaggagt ttatggagca gctcaaggat gcgggaaggc cattgtgtgc   780
caagcggaat gccgaggatc gtttaaatct gctgaagctg aagctattga agctggtgc    840
cattttctgc tcggaacgtt atcccgagga tgcggaggcc attgaccggg agattggacg   900
gcagttgaac gaggcggaga gtggacagat gagcaccaca acgacgagca acacccgcac   960
catcgaggtg gtgcagtgcg acaatcaaaa cacgacgata acaattacgg tgggcgaggc  1020
caccaccact tgcgccacag ccagtggagc gatgggatcc tccgctgccg aagcggctgc  1080
caatgaggcc aatgccaatc aaatagaaa tccaaatgcc aacggcgaca tctgactgcc  1140
cattttgggc agtcttaggt aaagtctgcc ggcgaaaac taacgcaact gggtgcgcca  1200
atcaaaatca agagccaaaa ggatataccg aagacatcag tcctgcaaca ttgggttaac  1260
ataaatcgta tttgtagcat gtaattaggc actgcgaaat cagcaaaaac gaaacgggaga  1320
cgaaatcaat cattgaaaat gcttcatagt atctaagagc aaatgaaagt taacgaacaa  1380
tacacgtact agatttaaac accgggtcac gaggctcaag agaacaagag gcccgcgcag  1440
atttgaaaag tcttttagca atcacagtca gcggaatcgt atttaaccgc atatacacga  1500
gttcacacca agccgtacta gtagaataat aatcaaaggt tagcgaaata agtattatac  1560
ttgaggtaga atcccacaac cagagcgaac cccaattgga tggagttgtc ccaggaaact  1620
```

```
gttgatttgc ttaccgtgta aattgtgtta cgaatagtag gtagagtgga aacgcacatc    1680
aaatattgtt tttagaccaa tgccattgtg aatgtcattc gttaaaggcc aattgagact    1740
gactgaattt atgtgtaata ggttttttcg tggtttgagc ggttcgggaa agatcggatg    1800
gaagcctcca gcgctgctgc cctgtcctcc cagaatcccc cgtcttcccc gcccctaagc    1860
gacagcgcaa acattgttag ctaattaaac aataatggaa cacaataacg caaattgcaa    1920
ttgcccaatc aaagttggta actgtaactg tctacaattc gaataagcaa taagggaaac    1980
cgtaaacgta aacgaaatct aaaccgaat gcaaacagtg aacaattatt aaatatagtg     2040
aaaagcatac agtaaatgca agtgaaaacc ccgaggcaaa ctatatacac gaaaccaagt    2100
aataaataaa tgattattaa actaaaaaaa aaaaaaaaa aaa                       2143
```

<210> SEQ ID NO 22
<211> LENGTH: 221
<212> TYPE: PRT
<213> ORGANISM: Mus musculus

<400> SEQUENCE: 22

```
Met Gly Asn Met Gln Glu Arg Pro Ser Glu Thr Ile Asp Arg Glu Arg
 1               5                  10                  15

Lys Arg Leu Val Glu Thr Leu Gln Ala Asp Ser Gly Leu Leu Leu Asp
            20                  25                  30

Ala Leu Val Ala Arg Gly Val Leu Thr Gly Pro Glu Tyr Glu Ala Leu
        35                  40                  45

Asp Ala Leu Pro Asp Ala Glu Arg Arg Val Arg Leu Leu Leu Leu
    50                  55                  60

Val Gln Ser Lys Gly Glu Ala Ala Cys Gln Glu Leu Leu Arg Cys Ala
 65                  70                  75                  80

Gln Gln Thr Val Ser Met Pro Asp Pro Ala Trp Asp Trp Gln His Val
                85                  90                  95

Gly Pro Gly Tyr Arg Asp Arg Ser Tyr Asp Pro Pro Cys Pro Gly His
            100                 105                 110

Trp Thr Pro Glu Ala Pro Ser Ser Gly Thr Thr Cys Pro Gly Leu Pro
        115                 120                 125

Arg Ala Ser Glu Glu Glu Ile Gly Gly Pro Glu Asp Ser Glu Ala
    130                 135                 140

Val Gln Pro Arg Thr Pro Glu Glu Pro Glu Leu Glu Ala Glu Ala Thr
145                 150                 155                 160

Lys Gly Asp Glu Pro Asp Leu Glu Gln Glu Met Glu Pro Glu Pro Glu
                165                 170                 175

Pro Glu Val Glu Pro Glu Pro Glu Pro Glu Pro Glu
            180                 185                 190

Pro Glu Pro Glu Pro Glu Pro Glu Pro Glu Arg Glu Pro Asp
        195                 200                 205

Phe Gln Glu Gly Asp Glu Ser Glu Gly Cys Glu Asn Thr
    210                 215                 220
```

<210> SEQ ID NO 23
<211> LENGTH: 416
<212> TYPE: PRT
<213> ORGANISM: Homo sapiens

<400> SEQUENCE: 23

```
Met Asp Glu Ala Asp Arg Arg Leu Leu Arg Arg Cys Arg Leu Arg Leu
 1               5                  10                  15
```

```
Val Glu Glu Leu Gln Val Asp Gln Leu Trp Asp Val Leu Leu Ser Arg
             20                  25                  30

Glu Leu Phe Arg Pro His Met Ile Glu Asp Ile Gln Arg Ala Gly Ser
         35                  40                  45

Gly Ser Arg Arg Asp Gln Ala Arg Gln Leu Ile Ile Asp Leu Glu Thr
     50                  55                  60

Arg Gly Ser Gln Ala Leu Pro Leu Phe Ile Ser Cys Leu Glu Asp Thr
 65                  70                  75                  80

Gly Gln Asp Met Leu Ala Ser Phe Leu Arg Thr Asn Arg Gln Ala Gly
                 85                  90                  95

Lys Leu Ser Lys Pro Thr Leu Glu Asn Leu Thr Pro Val Val Leu Arg
             100                 105                 110

Pro Glu Ile Arg Lys Pro Glu Val Leu Arg Pro Glu Thr Pro Arg Pro
         115                 120                 125

Val Asp Ile Gly Ser Gly Gly Phe Gly Asp Val Gly Ala Leu Glu Ser
     130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                 165                 170                 175

Leu Arg Thr Arg Thr Gly Ser Asn Ile Asp Cys Glu Lys Leu Arg Arg
             180                 185                 190

Arg Phe Ser Ser Leu His Phe Met Val Glu Val Lys Gly Asp Leu Thr
         195                 200                 205

Ala Lys Lys Met Val Leu Ala Leu Leu Glu Leu Ala Arg Gln Asp His
     210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                 245                 250                 255

Pro Val Ser Val Glu Lys Ile Val Asn Ile Phe Asn Gly Thr Ser Cys
             260                 265                 270

Pro Ser Leu Gly Gly Lys Pro Lys Leu Phe Phe Ile Gln Ala Cys Gly
         275                 280                 285

Gly Glu Gln Lys Asp His Gly Phe Glu Val Ala Ser Thr Ser Pro Glu
     290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                 325                 330                 335

Thr Pro Ser Asp Ile Phe Val Ser Tyr Ser Thr Phe Pro Gly Phe Val
             340                 345                 350

Ser Trp Arg Asp Pro Lys Ser Gly Ser Trp Tyr Val Glu Thr Leu Asp
         355                 360                 365

Asp Ile Phe Glu Gln Trp Ala His Ser Glu Asp Leu Gln Ser Leu Leu
     370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                 405                 410                 415

<210> SEQ ID NO 24
<211> LENGTH: 272
<212> TYPE: PRT
```

<213> ORGANISM: Homo sapiens

<400> SEQUENCE: 24

```
Met Ala Ala Asp Arg Gly Arg Gly Val Cys Gly Met His His His
 1               5                  10                  15

Thr Lys Lys Asn Arg Val Val Ala Lys Ser His Lys Asp Thr Met Arg
                 20                  25                  30

Ala Lys Val Gly Ser Ser Asn Val Asn Lys Arg Gly Ala Asp Ala Cys
             35                  40                  45

Ala Arg Thr Lys Gly His Asp Met Thr Thr Ser Gly His Val Ser Cys
 50                  55                  60

Asp Tyr Asp Ser Val Cys Ser Cys Tyr Lys Lys Arg Ser Thr Asp Thr
 65                  70                  75                  80

Val His Ser Asp Asn Lys Asp Gly Val Cys Val Lys Cys Thr Tyr Thr
                 85                  90                  95

His Ala Tyr Arg Ser Arg Arg Gly Ala Val Ser Asn Val His Thr Gly
            100                 105                 110

Lys Arg Ser Gly Gly Asp Val Asp His Ser Thr Val Thr Lys Gly Tyr
            115                 120                 125

Asp Val His Val Cys Asp Thr Ala Met Lys Asn Ala Ala His Arg Val
130                 135                 140

Thr Asp Ser Cys Val Ala Ser His Gly Val Gly Ala Tyr Gly Val Asp
145                 150                 155                 160

Gly Lys Val Asp Asn Ala Asn Cys Ser Asn Lys Lys Met Ala Cys Arg
                165                 170                 175

Gly Asp Thr Asp Arg Gly Val Asp Asp Gly Lys Asn His Ala Gly Ser
            180                 185                 190

Gly Cys Ser Asp Ala Gly Lys Lys Lys Met Arg Thr Arg Ser Asp Met
            195                 200                 205

Cys Gly Tyr Ala Cys Lys Gly Thr Ala Ala Met Arg Asn Thr Lys Arg
            210                 215                 220

Gly Ser Trp Tyr Ala Ala Val Ser Arg Ala Cys Asp Met His Val Ala
225                 230                 235                 240

Asp Met Val Lys Val Asn Ala Lys Asp Arg Gly Tyr Ala Gly Thr His
                245                 250                 255

Arg Cys Lys Met Ser Tyr Cys Ser Thr Cys Arg His Tyr Gly His Thr
                260                 265                 270
```

<210> SEQ ID NO 25
<211> LENGTH: 199
<212> TYPE: PRT
<213> ORGANISM: Homo sapiens

<400> SEQUENCE: 25

```
Met Glu Ala Arg Asp Lys Gln Val Leu Arg Ser Leu Arg Leu Glu Leu
 1               5                  10                  15

Gly Ala Glu Val Leu Val Glu Gly Leu Val Leu Gln Tyr Leu Tyr Gln
                 20                  25                  30

Glu Gly Ile Leu Thr Glu Asn His Ile Gln Glu Ile Asn Ala Gln Thr
             35                  40                  45

Thr Gly Leu Arg Lys Thr Met Leu Leu Leu Asp Ile Leu Pro Ser Arg
 50                  55                  60

Gly Pro Lys Ala Phe Asp Thr Phe Leu Asp Ser Leu Gln Glu Phe Pro
 65                  70                  75                  80

Trp Val Arg Glu Lys Leu Lys Lys Ala Arg Glu Glu Ala Met Thr Asp
```

```
                         85                     90                     95
Leu Pro Ala Gly Asp Arg Leu Thr Gly Ile Pro Ser His Ile Leu Asn
                100                     105                    110

Ser Ser Pro Ser Asp Arg Gln Ile Asn Gln Leu Ala Gln Arg Leu Gly
        115                     120                    125

Pro Glu Trp Glu Pro Met Val Leu Ser Leu Gly Leu Ser Gln Thr Asp
    130                     135                    140

Ile Tyr Arg Cys Lys Ala Asn His Pro His Asn Val Gln Ser Gln Val
145                     150                    155                    160

Val Glu Ala Phe Ile Arg Trp Arg Gln Arg Phe Gly Lys Gln Ala Thr
                165                     170                    175

Phe Gln Ser Leu His Asn Gly Leu Arg Ala Val Glu Val Asp Pro Ser
            180                     185                    190

Leu Leu Leu His Met Leu Glu
            195

<210> SEQ ID NO 26
<211> LENGTH: 1194
<212> TYPE: PRT
<213> ORGANISM: Homo sapiens

<400> SEQUENCE: 26

Met Asp Ala Lys Ala Arg Asn Cys Leu Leu Gln His Arg Glu Ala Leu
  1               5                  10                     15

Glu Lys Asp Ile Lys Thr Ser Tyr Ile Met Asp His Met Ile Ser Asp
                 20                     25                     30

Gly Phe Leu Thr Ile Ser Glu Glu Lys Val Arg Asn Glu Pro Thr
             35                     40                     45

Gln Gln Gln Arg Ala Ala Met Leu Ile Lys Met Ile Leu Lys Lys Asp
     50                     55                     60

Asn Asp Ser Tyr Val Ser Phe Tyr Asn Ala Leu His Glu Gly Tyr
 65                     70                     75                     80

Lys Asp Leu Ala Ala Leu Leu His Asp Gly Ile Pro Val Val Ser Ser
                85                     90                     95

Ser Ser Val Arg Thr Val Leu Cys Glu Gly Val Pro Gln Arg Pro
                100                    105                    110

Val Val Phe Val Thr Arg Lys Lys Leu Val Asn Ala Ile Gln Gln Lys
            115                    120                    125

Leu Ser Lys Leu Lys Gly Glu Pro Gly Trp Val Thr Ile His Gly Met
    130                    135                    140

Ala Gly Cys Gly Lys Ser Val Leu Ala Ala Glu Ala Val Arg Asp His
145                    150                    155                    160

Ser Leu Leu Glu Gly Cys Phe Pro Gly Gly Val His Trp Val Ser Val
                165                    170                    175

Gly Lys Gln Asp Lys Ser Gly Leu Leu Met Lys Leu Gln Asn Leu Cys
            180                    185                    190

Thr Arg Leu Asp Gln Asp Glu Ser Phe Ser Gln Arg Leu Pro Leu Asn
        195                    200                    205

Ile Glu Glu Ala Lys Asp Arg Leu Arg Ile Leu Met Leu Arg Lys His
    210                    215                    220

Pro Arg Ser Leu Leu Ile Leu Asp Asp Val Trp Asp Ser Trp Val Leu
225                    230                    235                    240

Lys Ala Phe Asp Ser Gln Cys Gln Ile Leu Leu Thr Thr Arg Asp Lys
                245                    250                    255
```

```
Ser Val Thr Asp Ser Val Met Gly Pro Lys Tyr Val Pro Val Glu
            260                 265                 270

Ser Ser Leu Gly Lys Glu Lys Gly Leu Glu Ile Leu Ser Leu Phe Val
        275                 280                 285

Asn Met Lys Lys Ala Asp Leu Pro Glu Gln Ala His Ser Ile Ile Lys
        290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Tyr Asp Tyr Glu Ala
            340                 345                 350

Leu Asp Glu Ala Met Ser Ile Ser Val Glu Met Leu Arg Glu Asp Ile
            355                 360                 365

Lys Asp Tyr Tyr Thr Asp Leu Ser Ile Leu Gln Lys Asp Val Lys Val
            370                 375                 380

Pro Thr Lys Val Leu Cys Ile Leu Trp Asp Met Glu Thr Glu Val
385                 390                 395                 400

Glu Asp Ile Leu Gln Glu Phe Val Asn Lys Ser Leu Leu Phe Cys Asp
                405                 410                 415

Arg Asn Gly Lys Ser Phe Arg Tyr Tyr Leu His Asp Leu Gln Val Asp
            420                 425                 430

Phe Leu Thr Glu Lys Asn Cys Ser Gln Leu Gln Asp Leu His Lys Lys
        435                 440                 445

Ile Ile Thr Gln Phe Gln Arg Tyr His Gln Pro His Thr Leu Ser Pro
    450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
                485                 490                 495

Asp Trp Ile Lys Ala Lys Thr Glu Leu Val Gly Pro Ala His Leu Ile
            500                 505                 510

His Glu Phe Val Glu Tyr Arg His Ile Leu Asp Glu Lys Asp Cys Ala
            515                 520                 525

Val Ser Glu Asn Phe Gln Glu Phe Leu Ser Leu Asn Gly His Leu Leu
    530                 535                 540

Gly Arg Gln Pro Phe Pro Asn Ile Val Gln Leu Gly Leu Cys Glu Pro
545                 550                 555                 560

Glu Thr Ser Glu Val Tyr Gln Gln Ala Lys Leu Gln Ala Lys Gln Glu
                565                 570                 575

Val Asp Asn Gly Met Leu Tyr Leu Glu Trp Ile Asn Lys Lys Asn Ile
            580                 585                 590

Thr Asn Leu Ser Arg Leu Val Val Arg Pro His Thr Asp Ala Val Tyr
        595                 600                 605

His Ala Cys Phe Ser Glu Asp Gly Gln Arg Ile Ala Ser Cys Gly Ala
        610                 615                 620

Asp Lys Thr Leu Gln Val Phe Lys Ala Glu Thr Gly Glu Lys Leu Leu
625                 630                 635                 640

Glu Ile Lys Ala His Glu Asp Glu Val Leu Cys Cys Ala Phe Ser Thr
                645                 650                 655

Asp Asp Arg Phe Ile Ala Thr Cys Ser Val Asp Lys Lys Val Lys Ile
            660                 665                 670

Trp Asn Ser Met Thr Gly Glu Leu Val His Thr Tyr Asp Glu His Ser
```

-continued

```
                675                 680                 685
Glu Gln Val Asn Cys Cys His Phe Thr Asn Ser Ser His His Leu Leu
        690                 695                 700

Leu Ala Thr Gly Ser Ser Asp Cys Phe Leu Lys Leu Trp Asp Leu Asn
705                 710                 715                 720

Gln Lys Glu Cys Arg Asn Thr Met Phe Gly His Thr Asn Ser Val Asn
                725                 730                 735

His Cys Arg Phe Ser Pro Asp Lys Leu Leu Ala Ser Cys Ser Ala
            740                 745                 750

Asp Gly Thr Leu Lys Leu Trp Asp Ala Thr Ser Ala Asn Glu Arg Lys
                755                 760                 765

Ser Ile Asn Val Lys Gln Phe Phe Leu Asn Leu Glu Asp Pro Gln Glu
    770                 775                 780

Asp Met Glu Val Ile Val Lys Cys Cys Ser Trp Ser Ala Asp Gly Ala
785                 790                 795                 800

Arg Ile Met Val Ala Ala Lys Asn Lys Ile Phe Leu Trp Asn Thr Asp
                805                 810                 815

Ser Arg Ser Lys Val Ala Asp Cys Arg Gly His Leu Ser Trp Val His
            820                 825                 830

Gly Val Met Phe Ser Pro Asp Gly Ser Ser Phe Leu Thr Ser Ser Asp
        835                 840                 845

Asp Gln Thr Ile Arg Leu Trp Glu Thr Lys Lys Val Cys Lys Asn Ser
850                 855                 860

Ala Val Met Leu Lys Gln Glu Val Asp Val Val Phe Gln Glu Asn Glu
865                 870                 875                 880

Val Met Val Leu Ala Val Asp His Ile Arg Arg Leu Gln Leu Ile Asn
                885                 890                 895

Gly Arg Thr Gly Gln Ile Asp Tyr Leu Thr Glu Ala Gln Val Ser Cys
            900                 905                 910

Cys Cys Leu Ser Pro His Leu Gln Tyr Ile Ala Phe Gly Asp Glu Asn
        915                 920                 925

Gly Ala Ile Glu Ile Leu Glu Leu Val Asn Asn Arg Ile Phe Gln Ser
    930                 935                 940

Arg Phe Gln His Lys Lys Thr Val Trp His Ile Gln Phe Thr Ala Asp
945                 950                 955                 960

Glu Lys Thr Leu Ile Ser Ser Ser Asp Asp Ala Glu Ile Gln Val Trp
                965                 970                 975

Asn Trp Gln Leu Asp Lys Cys Ile Phe Leu Arg Gly His Gln Glu Thr
            980                 985                 990

Val Lys Asp Phe Arg Leu Leu Lys Asn Ser Arg Leu Leu Ser Trp Ser
        995                 1000                1005

Phe Asp Gly Thr Val Lys Val Trp Asn Ile Ile Thr Gly Asn Lys Glu
    1010                1015                1020

Lys Asp Phe Val Cys His Gln Gly Thr Val Leu Ser Cys Asp Ile Ser
1025                1030                1035                1040

His Asp Ala Thr Lys Phe Ser Ser Thr Ser Ala Asp Lys Thr Ala Lys
                1045                1050                1055

Ile Trp Ser Phe Asp Leu Leu Leu Pro Leu His Glu Leu Arg Gly His
            1060                1065                1070

Asn Gly Cys Val Arg Cys Ser Ala Phe Ser Val Asp Ser Thr Leu Leu
        1075                1080                1085

Ala Thr Gly Asp Asp Asn Gly Glu Ile Arg Ile Trp Asn Val Ser Asn
    1090                1095                1100
```

```
Gly Glu Leu Leu His Leu Cys Ala Pro Leu Ser Glu Glu Gly Ala Ala
1105                1110                1115                1120

Thr His Gly Gly Trp Val Thr Asp Leu Cys Phe Ser Pro Asp Gly Lys
                1125                1130                1135

Met Leu Ile Ser Ala Gly Gly Tyr Ile Lys Trp Trp Asn Val Val Thr
                1140                1145                1150

Gly Glu Ser Ser Gln Thr Phe Tyr Thr Asn Gly Thr Asn Leu Lys Lys
                1155                1160                1165

Ile His Val Ser Pro Asp Phe Lys Thr Tyr Val Thr Val Asp Asn Leu
        1170                1175                1180

Gly Ile Leu Tyr Ile Leu Gln Thr Leu Glu
1185                1190

<210> SEQ ID NO 27
<211> LENGTH: 540
<212> TYPE: PRT
<213> ORGANISM: Homo sapiens

<400> SEQUENCE: 27

Met Asn Gly Glu Ala Ile Cys Ser Ala Leu Pro Thr Ile Pro Tyr His
 1               5                  10                  15

Lys Leu Ala Asp Leu Arg Tyr Leu Ser Arg Gly Ala Ser Gly Thr Val
            20                  25                  30

Ser Ser Ala Arg His Ala Asp Trp Arg Val Gln Val Ala Val Lys His
        35                  40                  45

Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
```

-continued

```
                 275                 280                 285

Glu Leu Glu Pro Val Leu Arg Thr Phe Glu Glu Ile Thr Phe Leu Glu
            290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
                325                 330                 335

Val Asn His Gly Pro Gln Glu Ser Cys Gly Ser Ser Gln Leu His
            340                 345                 350

Glu Asn Ser Gly Ser Pro Glu Thr Ser Arg Ser Leu Pro Ala Pro Gln
            355                 360                 365

Asp Asn Asp Phe Leu Ser Arg Lys Ala Gln Asp Cys Tyr Phe Met Lys
370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Thr Pro Cys Ser Ser
                405                 410                 415

Ala Ile Ile Asn Pro Leu Ser Thr Ala Gly Asn Ser Glu Arg Leu Gln
            420                 425                 430

Pro Gly Ile Ala Gln Gln Trp Ile Gln Ser Lys Arg Glu Asp Ile Val
            435                 440                 445

Asn Gln Met Thr Glu Ala Cys Leu Asn Gln Ser Leu Asp Ala Leu Leu
450                 455                 460

Ser Arg Asp Leu Ile Met Lys Glu Asp Tyr Glu Leu Val Ser Thr Lys
465                 470                 475                 480

Pro Thr Arg Thr Ser Lys Val Arg Gln Leu Leu Asp Thr Thr Asp Ile
                485                 490                 495

Gln Gly Glu Glu Phe Ala Lys Val Ile Val Gln Lys Leu Lys Asp Asn
            500                 505                 510

Lys Gln Met Gly Leu Gln Pro Tyr Pro Glu Ile Leu Val Val Ser Arg
            515                 520                 525

Ser Pro Ser Leu Asn Leu Leu Gln Asn Lys Ser Met
530                 535                 540

<210> SEQ ID NO 28
<211> LENGTH: 656
<212> TYPE: PRT
<213> ORGANISM: Mus musculus

<400> SEQUENCE: 28

Met Gln Pro Asp Met Ser Leu Asp Asn Ile Lys Met Ala Ser Ser Asp
 1               5                  10                  15

Leu Leu Glu Lys Thr Asp Leu Asp Ser Gly Gly Phe Gly Lys Val Ser
            20                  25                  30

Leu Cys Tyr His Arg Ser His Gly Phe Val Ile Leu Lys Lys Val Tyr
        35                  40                  45

Thr Gly Pro Asn Arg Ala Glu Tyr Asn Glu Val Leu Leu Glu Glu Gly
    50                  55                  60

Lys Met Met His Arg Leu Arg His Ser Arg Val Val Lys Leu Leu Gly
65                  70                  75                  80

Ile Ile Ile Glu Glu Gly Asn Tyr Ser Leu Val Met Glu Tyr Met Glu
                85                  90                  95

Lys Gly Asn Leu Met His Val Leu Lys Thr Gln Ile Asp Val Pro Leu
            100                 105                 110
```

-continued

```
Ser Leu Lys Gly Arg Ile Ile Val Glu Ala Ile Glu Gly Met Cys Tyr
            115                 120                 125
Leu His Asp Lys Gly Val Ile His Lys Asp Leu Lys Pro Glu Asn Ile
    130                 135                 140
Leu Val Asp Arg Asp Phe His Ile Lys Ile Ala Asp Leu Gly Val Ala
145                 150                 155                 160
Ser Phe Lys Thr Trp Ser Lys Leu Thr Lys Glu Lys Asp Asn Lys Gln
                165                 170                 175
Lys Glu Val Ser Ser Thr Thr Lys Lys Asn Asn Gly Gly Thr Leu Tyr
            180                 185                 190
Tyr Met Ala Pro Glu His Leu Asn Asp Ile Asn Ala Lys Pro Thr Glu
        195                 200                 205
Lys Ser Asp Val Tyr Ser Phe Gly Ile Val Leu Trp Ala Ile Phe Ala
    210                 215                 220
Lys Lys Glu Pro Tyr Glu Asn Val Ile Cys Thr Glu Gln Phe Val Ile
225                 230                 235                 240
Cys Ile Lys Ser Gly Asn Arg Pro Asn Val Glu Glu Ile Leu Glu Tyr
                245                 250                 255
Cys Pro Arg Glu Ile Ile Ser Leu Met Glu Arg Cys Trp Gln Ala Ile
            260                 265                 270
Pro Glu Asp Arg Pro Thr Phe Leu Gly Ile Glu Glu Phe Arg Pro
        275                 280                 285
Phe Tyr Leu Ser His Phe Glu Glu Tyr Val Glu Glu Asp Val Ala Ser
    290                 295                 300
Leu Lys Lys Glu Tyr Pro Asp Gln Ser Pro Val Leu Gln Arg Met Phe
305                 310                 315                 320
Ser Leu Gln His Asp Cys Val Pro Leu Pro Pro Ser Arg Ser Asn Ser
                325                 330                 335
Glu Gln Pro Gly Ser Leu His Ser Ser Gln Gly Leu Gln Met Gly Pro
            340                 345                 350
Val Glu Glu Ser Trp Phe Ser Ser Ser Pro Glu Tyr Pro Gln Asp Glu
        355                 360                 365
Asn Asp Arg Ser Val Gln Ala Lys Leu Gln Glu Glu Ala Ser Tyr His
    370                 375                 380
Ala Phe Gly Ile Phe Ala Glu Lys Gln Thr Lys Pro Gln Pro Arg Gln
385                 390                 395                 400
Asn Glu Ala Tyr Asn Arg Glu Glu Arg Lys Arg Arg Val Ser His
                405                 410                 415
Asp Pro Phe Ala Gln Gln Arg Ala Arg Glu Asn Ile Lys Ser Ala Gly
            420                 425                 430
Ala Arg Gly His Ser Asp Pro Ser Thr Thr Ser Arg Gly Ile Ala Val
        435                 440                 445
Gln Gln Leu Ser Trp Pro Ala Thr Gln Thr Val Trp Asn Asn Gly Leu
    450                 455                 460
Tyr Asn Gln His Gly Phe Gly Thr Thr Gly Thr Gly Val Trp Tyr Pro
465                 470                 475                 480
Pro Asn Leu Ser Gln Met Tyr Ser Thr Tyr Lys Thr Pro Val Pro Glu
                485                 490                 495
Thr Asn Ile Pro Gly Ser Thr Pro Thr Met Pro Tyr Phe Ser Gly Pro
            500                 505                 510
Val Ala Asp Asp Leu Ile Lys Tyr Thr Ile Phe Asn Ser Ser Gly Ile
        515                 520                 525
Gln Ile Gly Asn His Asn Tyr Met Asp Val Gly Leu Asn Ser Gln Pro
```

```
                530             535             540
Pro Asn Asn Thr Cys Lys Glu Glu Ser Thr Ser Arg His Gln Ala Ile
545                 550                 555                 560

Phe Asp Asn Thr Thr Ser Leu Thr Asp Glu His Leu Asn Pro Ile Arg
                565                 570                 575

Glu Asn Leu Gly Arg Gln Trp Lys Asn Cys Ala Arg Lys Leu Gly Phe
            580                 585                 590

Thr Glu Ser Gln Ile Asp Glu Ile Asp His Asp Tyr Glu Arg Asp Gly
        595                 600                 605

Leu Lys Glu Lys Val Tyr Gln Met Leu Gln Lys Trp Leu Met Arg Glu
610                 615                 620

Gly Thr Lys Gly Ala Thr Val Gly Lys Leu Ala Gln Ala Leu His Gln
625                 630                 635                 640

Cys Cys Arg Ile Asp Leu Leu Asn His Leu Ile Arg Ala Ser Gln Ser
                645                 650                 655
```

<210> SEQ ID NO 29
<211> LENGTH: 618
<212> TYPE: PRT
<213> ORGANISM: Homo sapiens

<400> SEQUENCE: 29

```
Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255
```

-continued

```
Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
            275                 280                 285

Gln Leu Ala Ser Ala Gly Phe Tyr Val Gly Arg Asn Asp Asp Val
    290                 295                 300

Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
                340                 345                 350

Pro His Leu Leu Glu Gln Leu Leu Ser Thr Ser Asp Thr Thr Gly Glu
            355                 360                 365

Glu Asn Ala Asp Pro Pro Ile Ile His Phe Gly Pro Gly Glu Ser Ser
    370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
                420                 425                 430

Ala Leu Leu Asn Ala Glu Asp Glu Lys Arg Glu Glu Lys Glu Lys
                435                 440                 445

Gln Ala Glu Glu Met Ala Ser Asp Asp Leu Ser Leu Ile Arg Lys Asn
    450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
                500                 505                 510

Ile Leu Val Lys Gly Asn Ala Ala Asn Ile Phe Lys Asn Cys Leu
    515                 520                 525

Lys Glu Ile Asp Ser Thr Leu Tyr Lys Asn Leu Phe Val Asp Lys Asn
            530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
            580                 585                 590

Gln Glu Cys Ala Pro Ser Leu Arg Lys Cys Pro Ile Cys Arg Gly Ile
    595                 600                 605

Ile Lys Gly Thr Val Arg Thr Phe Leu Ser
    610                 615

<210> SEQ ID NO 30
<211> LENGTH: 404
<212> TYPE: PRT
<213> ORGANISM: Homo sapiens

<400> SEQUENCE: 30

Met Ala Asp Lys Val Leu Lys Glu Lys Arg Lys Leu Phe Ile Arg Ser
1               5                   10                  15
```

```
Met Gly Glu Gly Thr Ile Asn Gly Leu Leu Asp Glu Leu Leu Gln Thr
            20                  25                  30
Arg Val Leu Asn Lys Glu Glu Met Glu Lys Val Lys Arg Glu Asn Ala
        35                  40                  45
Thr Val Met Asp Lys Thr Arg Ala Leu Ile Asp Ser Val Ile Pro Lys
    50                  55                  60
Gly Ala Gln Ala Cys Gln Ile Cys Ile Thr Tyr Ile Cys Glu Glu Asp
65                  70                  75                  80
Ser Tyr Leu Ala Gly Thr Leu Gly Leu Ser Ala Asp Gln Thr Ser Gly
                85                  90                  95
Asn Tyr Leu Asn Met Gln Asp Ser Gln Gly Val Leu Ser Ser Phe Pro
            100                 105                 110
Ala Pro Gln Ala Val Gln Asp Asn Pro Ala Met Pro Thr Ser Ser Gly
        115                 120                 125
Ser Glu Gly Asn Val Lys Leu Cys Ser Leu Glu Glu Ala Gln Arg Ile
    130                 135                 140
Trp Lys Gln Lys Ser Ala Glu Ile Tyr Pro Ile Met Asp Lys Ser Ser
145                 150                 155                 160
Arg Thr Arg Leu Ala Leu Ile Ile Cys Asn Glu Glu Phe Asp Ser Ile
                165                 170                 175
Pro Arg Arg Thr Gly Ala Glu Val Asp Ile Thr Gly Met Thr Met Leu
            180                 185                 190
Leu Gln Asn Leu Gly Tyr Ser Val Asp Val Lys Lys Asn Leu Thr Ala
        195                 200                 205
Ser Asp Met Thr Thr Glu Leu Glu Ala Phe Ala His Arg Pro Glu His
    210                 215                 220
Lys Thr Ser Asp Ser Thr Phe Leu Val Phe Met Ser His Gly Ile Arg
225                 230                 235                 240
Glu Gly Ile Cys Gly Lys Lys His Ser Glu Gln Val Pro Asp Ile Leu
                245                 250                 255
Gln Leu Asn Ala Ile Phe Asn Met Leu Asn Thr Lys Asn Cys Pro Ser
            260                 265                 270
Leu Lys Asp Lys Pro Lys Val Ile Ile Ile Gln Ala Cys Arg Gly Asp
        275                 280                 285
Ser Pro Gly Val Val Trp Phe Lys Asp Ser Val Gly Val Ser Gly Asn
    290                 295                 300
Leu Ser Leu Pro Thr Thr Glu Glu Phe Glu Asp Asp Ala Ile Lys Lys
305                 310                 315                 320
Ala His Ile Glu Lys Asp Phe Ile Ala Phe Cys Ser Ser Thr Pro Asp
                325                 330                 335
Asn Val Ser Trp Arg His Pro Thr Met Gly Ser Val Phe Ile Gly Arg
            340                 345                 350
Leu Ile Glu His Met Gln Glu Tyr Ala Cys Ser Cys Asp Val Glu Glu
        355                 360                 365
Ile Phe Arg Lys Val Arg Phe Ser Phe Glu Gln Pro Asp Gly Arg Ala
    370                 375                 380
Gln Met Pro Thr Thr Glu Arg Val Thr Leu Thr Arg Cys Phe Tyr Leu
385                 390                 395                 400
Phe Pro Gly His

<210> SEQ ID NO 31
<211> LENGTH: 239
<212> TYPE: PRT
```

<213> ORGANISM: Mus musculus

<400> SEQUENCE: 31

Met Asp Tyr Ala Met Lys Ser Leu Ser Leu Leu Tyr Pro Arg Ser Leu
1               5                   10                  15

Ser Arg His Val Ala Val Ser Thr Ala Val Val Thr Gln Gln Leu Val
            20                  25                  30

Ser Lys Pro Ser Arg Glu Thr Pro Arg Ala Arg Pro Cys Arg Val Ser
        35                  40                  45

Thr Ala Asp Arg Lys Val Arg Lys Gly Ile Met Ala His Ser Leu Glu
    50                  55                  60

Asp Leu Leu Asn Lys Val Gln Asp Ile Leu Lys Leu Lys Asp Lys Pro
65                  70                  75                  80

Phe Ser Leu Val Leu Glu Glu Asp Gly Thr Ile Val Glu Thr Glu Glu
                85                  90                  95

Tyr Phe Gln Ala Leu Ala Lys Asp Thr Met Phe Met Val Leu Leu Lys
            100                 105                 110

Gly Gln Lys Trp Lys Pro Pro Ser Glu Gln Arg Lys Lys Arg Ala Gln
        115                 120                 125

Leu Ala Leu Ser Gln Lys Pro Thr Lys Lys Ile Asp Val Ala Arg Val
130                 135                 140

Thr Phe Asp Leu Tyr Lys Leu Asn Pro Gln Asp Phe Ile Gly Cys Leu
145                 150                 155                 160

Asn Val Lys Ala Thr Leu Tyr Asp Thr Tyr Ser Leu Ser Tyr Asp Leu
                165                 170                 175

His Cys Tyr Lys Ala Lys Arg Ile Val Lys Glu Ile Val Arg Trp Thr
            180                 185                 190

Leu Phe Ser Met Gln Ala Thr Gly His Met Leu Leu Gly Thr Ser Ser
        195                 200                 205

Tyr Met Gln Gln Phe Leu Asp Ala Thr Glu Glu Gln Pro Ala Lys
    210                 215                 220

Ala Lys Pro Ser Ser Leu Leu Pro Ala Cys Leu Lys Met Leu Gln
225                 230                 235

<210> SEQ ID NO 32
<211> LENGTH: 331
<212> TYPE: PRT
<213> ORGANISM: Mus musculus

<400> SEQUENCE: 32

Met Glu Val Thr Gly Asp Ala Gly Val Pro Glu Ser Gly Glu Ile Arg
1               5                   10                  15

Thr Leu Lys Pro Cys Leu Leu Arg Arg Asn Tyr Ser Arg Glu Gln His
            20                  25                  30

Gly Val Ala Ala Ser Cys Leu Glu Asp Leu Arg Ser Lys Ala Cys Asp
        35                  40                  45

Ile Leu Ala Ile Asp Lys Ser Leu Thr Pro Val Thr Leu Val Leu Ala
    50                  55                  60

Glu Asp Gly Thr Ile Val Asp Asp Asp Tyr Phe Leu Cys Leu Pro
65                  70                  75                  80

Ser Asn Thr Lys Phe Val Ala Leu Ala Ser Asn Glu Lys Trp Ala Tyr
                85                  90                  95

Asn Asn Ser Asp Gly Gly Thr Ala Trp Ile Ser Gln Glu Ser Phe Asp
            100                 105                 110

Val Asp Glu Thr Asp Ser Gly Ala Gly Leu Lys Trp Lys Asn Val Ala

```
            115                 120                 125
Arg Gln Leu Lys Glu Asp Leu Ser Ser Ile Ile Leu Leu Ser Glu Glu
        130                 135                 140

Asp Leu Gln Met Leu Val Asp Ala Pro Cys Ser Asp Leu Ala Gln Glu
145                 150                 155                 160

Leu Arg Gln Ser Cys Ala Thr Val Gln Arg Leu Gln His Thr Leu Gln
                165                 170                 175

Gln Val Leu Asp Gln Arg Glu Glu Val Arg Gln Ser Lys Gln Leu Leu
            180                 185                 190

Gln Leu Tyr Leu Gln Ala Leu Glu Lys Glu Gly Ser Leu Leu Ser Lys
        195                 200                 205

Gln Glu Glu Ser Lys Ala Ala Phe Gly Glu Glu Val Asp Ala Val Asp
    210                 215                 220

Thr Gly Ile Ser Arg Glu Thr Ser Ser Asp Val Ala Leu Ala Ser His
225                 230                 235                 240

Ile Leu Thr Ala Leu Arg Glu Lys Gln Ala Pro Glu Leu Ser Leu Ser
                245                 250                 255

Ser Gln Asp Leu Glu Leu Val Thr Lys Glu Asp Pro Lys Ala Leu Ala
            260                 265                 270

Val Ala Leu Asn Trp Asp Ile Lys Lys Thr Glu Thr Val Gln Glu Ala
        275                 280                 285

Cys Glu Arg Glu Leu Ala Leu Arg Leu Gln Thr Gln Ser Leu His
    290                 295                 300

Ser Leu Arg Ser Ile Ser Ala Ser Lys Ala Ser Pro Pro Gly Asp Leu
305                 310                 315                 320

Gln Asn Pro Lys Arg Ala Arg Gln Asp Pro Thr
                325                 330

<210> SEQ ID NO 33
<211> LENGTH: 2040
<212> TYPE: DNA
<213> ORGANISM: Homo sapiens

<400> SEQUENCE: 33
agcgagcttg cagcctcacc gacgagtctc aactaaaagg gactcccgga gctaggggtg      60
gggactcggc ctcacacagt gagtgccggc tattggactt ttgtccagtg acagctgaga     120
caacaaggac cacgggagga ggtgtaggag agaagcgccg cgaacagcga tcgcccagca     180
ccaagtccgc ttccaggctt tcggtttctt tgcctccatc ttgggtgcgc cttcccggcg     240
tctaggggag cgaaggctga ggtggcagcg gcaggagagt ccggccgcga caggacgaac     300
tcccccactg gaaaggattc tgaaagaaat gaagtcagcc ctcagaaatg aagttgactg     360
cctgctggct ttcctgttga ctggcccgga gctgtactgc aagacccttg tgagcttccc     420
tagtctaaga gtaggatgtc tgctgaagtc atccatcagg ttgaagaagc acttgataca     480
gatgagaagg agatgctgct ctttttgtgc cgggatgttg ctatagatgt ggttccacct     540
aatgtcaggg accttctgga tattttacgg gaaagaggta agctgtctgt cggggacttg     600
gctgaactgc tctacagagt gaggcgattt gacctgctca acgtatcttg aagatggac     660 agaaaagctg tggagaccca cctgctcagg aaccctcacc ttgtttcgga ctatagagtg     720
ctgatggcag agattggtga ggatttggat aaatctgatg tgtcctcatt aattttcctc     780
atgaaggatt acatgggccg aggcaagata agcaaggaga gatttcttg ggaccttgtg      840 gttgagttgg agaaactaaa tctggttgcc ccagatcaac tggatttatt agaaaaatgc     900
```

-continued

```
ctaaagaaca tccacagaat agacctgaag acaaaaatcc agaagtacaa gcagtctgtt      960
caaggagcag ggacaagtta caggaatgtt ctccaagcag caatccaaaa gagtctcaag     1020
gatccttcaa ataacttcag gctccataat gggagaagta agaacaaag acttaaggaa      1080 cagcttggcg ctcaacaaga accagtgaag aaatccattc aggaatcaga agcttttttg    1140
cctcagagca tacctgaaga gagatacaag atgaagagca agcccctagg aatctgcctg    1200
ataatcgatt gcattggcaa tgagacagag cttcttcgag acaccttcac ttccctgggc    1260
tatgaagtcc agaaattctt gcatctcagt atgcatggta tatcccagat tcttggccaa    1320
tttgcctgta tgcccgagca ccgagactac gacagctttg tgtgtgtcct ggtgagccga    1380
ggaggctccc agagtgtgta tggtgtggat cagactcact cagggctccc cctgcatcac    1440
atcaggagga tgttcatggg agaatcatgc ccttatctag cagggaagcc aaagatgttt    1500
tttattcaga actatgtggt gtcagagggc ccagctggag acagcagcct ctggagggtg    1560
gatgggccag cgatgaagaa tgtggaattc agggctcaga agcgagggct gtgcacagtt    1620
caccgagaag ctgacttctt ctggagcctg tgtactgcgg acatgtccct gctggagcag    1680
tctcacagct caccatccct gtacctgcag tgcctctccc agaaactgag acaagaaaga    1740
aaacgcccac tcctggatct tcacattgaa ctcaatggct acatgtatga ttggaacagc    1800
agagtttctg ccaaggagaa atattatgtc tggctgcagc acactctgag aaagaaactt    1860
atcctctcct acacataaga aaccaaaagg ctgggcgtag tggctcacac ctgtaatccc    1920
agcactttgg gaggccaagg agggcagatc acttcaggtc aggagttcga gaccagcctg    1980
gccaacatgg taaacgctgt ccctagtaaa aatacaaaaa ttaaaaaaaa aaaaaaaaa     2040
```

<210> SEQ ID NO 34
<211> LENGTH: 480
<212> TYPE: PRT
<213> ORGANISM: Homo sapiens

<400> SEQUENCE: 34

```
Met Ser Ala Glu Val Ile His Gln Val Glu Ala Leu Asp Thr Asp
  1               5                  10                  15

Glu Lys Glu Met Leu Leu Phe Leu Cys Arg Asp Val Ala Ile Asp Val
                 20                  25                  30

Val Pro Pro Asn Val Arg Asp Leu Leu Asp Ile Leu Arg Glu Arg Gly
             35                  40                  45

Lys Leu Ser Val Gly Asp Leu Ala Glu Leu Leu Tyr Arg Val Arg Arg
         50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                     85                  90                  95

Met Ala Glu Ile Gly Glu Asp Leu Asp Lys Ser Asp Val Ser Ser Leu
                100                 105                 110

Ile Phe Leu Met Lys Asp Tyr Met Gly Arg Gly Lys Ile Ser Lys Glu
            115                 120                 125

Lys Ile Ser Trp Asp Leu Val Val Glu Leu Glu Lys Leu Asn Leu Val
        130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Leu Tyr Lys Gln Ser Val Gln
                165                 170                 175
```

-continued

```
Gly Ala Gly Thr Ser Tyr Arg Asn Val Leu Gln Ala Ala Ile Gln Lys
            180                 185                 190
Ser Leu Lys Asp Pro Ser Asn Asn Phe Arg Leu His Asn Gly Arg Ser
        195                 200                 205
Lys Glu Gln Arg Leu Lys Glu Gln Leu Gly Ala Gln Gln Glu Pro Val
    210                 215                 220
Lys Lys Ser Ile Gln Glu Ser Glu Ala Phe Leu Pro Gln Ser Ile Pro
225                 230                 235                 240
Glu Glu Arg Tyr Lys Met Lys Ser Lys Pro Leu Gly Ile Cys Leu Ile
                245                 250                 255
Ile Asp Cys Ile Gly Asn Glu Thr Glu Leu Leu Arg Asp Thr Phe Thr
            260                 265                 270
Ser Leu Gly Tyr Glu Val Gln Lys Phe Leu His Leu Ser Met His Gly
        275                 280                 285
Ile Ser Gln Ile Leu Gly Gln Phe Ala Cys Met Pro Glu His Arg Asp
    290                 295                 300
Tyr Asp Ser Phe Val Cys Val Leu Val Ser Arg Gly Gly Ser Gln Ser
305                 310                 315                 320
Val Tyr Gly Val Asp Gln Thr His Ser Gly Leu Pro Leu His His Ile
                325                 330                 335
Arg Arg Met Phe Met Gly Glu Ser Cys Pro Tyr Leu Ala Gly Lys Pro
            340                 345                 350
Lys Met Phe Phe Ile Gln Asn Tyr Val Val Ser Glu Gly Pro Ala Gly
        355                 360                 365
Asp Ser Ser Leu Trp Arg Val Asp Gly Pro Ala Met Lys Asn Val Glu
    370                 375                 380
Phe Arg Ala Gln Lys Arg Gly Leu Cys Thr Val His Arg Glu Ala Asp
385                 390                 395                 400
Phe Phe Trp Ser Leu Cys Thr Ala Asp Met Ser Leu Leu Glu Gln Ser
                405                 410                 415
His Ser Ser Pro Ser Leu Tyr Leu Gln Cys Leu Ser Gln Lys Leu Arg
            420                 425                 430
Gln Glu Arg Lys Arg Pro Leu Leu Asp Leu His Ile Glu Leu Asn Gly
        435                 440                 445
Tyr Met Tyr Asp Trp Asn Ser Arg Val Ser Ala Lys Glu Lys Tyr Tyr
    450                 455                 460
Val Trp Leu Gln His Thr Leu Arg Lys Lys Leu Ile Leu Ser Tyr Thr
465                 470                 475                 480

<210> SEQ ID NO 35
<211> LENGTH: 1679
<212> TYPE: DNA
<213> ORGANISM: Homo sapiens

<400> SEQUENCE: 35
gctgctccga gctccgcgtc gcgtcgcgta gattcgcgtc gccgtcgacc tcagaggcgg      60
ggccggtaag cgctacggtt tgacccccga gtccctctgt tcccgaaggg gcggccgtct     120
ttctcccgac ccgctccgcc tcctctcctt cttcccatt acccggaggc cgaagccccc      180
agccagggcg gggcggcgca gcccgagctc ccggaccccgg aagaagcgcc atctcccgcc    240
tccaccatgg agcccaccgc accgtccctc accgaggagg acctcactga agtgaagaag     300
gacgccttag aaaatttacg tgtatacctg tgtgagaaaa tcatagctga gagacatttt     360
gatcatctac gtgcaaaaaa aatactcagt agagaagaca ctgaagaaat ttcttgtcga     420
```

-continued

```
acatcaagta gaaaaagggc tggaaaattg ttagactact tacaggaaaa cccaaaaggt    480
ctggacaccc ttgttgaatc tattcggcga gaaaaacac agaacttcct gatacagaag    540
attacagatg aagtgctgaa acttagaaat ataaaactag aacatctgaa aggactaaaa    600
tgtagcagtt gtgaaccttt tccagatgga gccacgaaca acctctccag atcaaattca    660
gatgagagta atttctctga aaaactgagg gcatccactg tcatgtacca tccagaagga    720
gaatccagca cgacgcccct ttttttctact aattcttctc tgaatttgcc tgttctagaa    780
gtaggcagaa ctgaaaatac catcttctct tcaactacac ttcccagacc tggggaccca    840
ggggctcctc ctttgccacc agatctacag ttagaagaag aaggaacttg tgcaaactct    900
agtgagatgt ttcttccctt aagatcacgt actgtttcac gacaatagac actttattgc    960
cttttaattt ttaatgatga caaaaaatgt tttaaagaat atgacttttt ataaaatggc   1020
tgtaatcatt tgtttacatt tgatgcatgt cttttaaaat gcaatgtaag catactttgt   1080
aaataggatt tttagaatta aaaaagcata cttctaggat agctaactgt aaatcatgtt   1140
gatcatgtac tttttagtaa tttctttttt tccttttttaa ggtctttcag tactttttta   1200
aatattttct attttaagac tgattttaat agggaatata tctctatttg agaatagacc   1260
cttactagga agaacgtttt ttcctcagtg catttgtgct agaaattttc aagagtctaa   1320
tagtcttgcc agtcattcag cagcaaattt tcagcattaa gctgttcctg ttcagtaata   1380
aaaccggtca ctgatgggaa aactgccaat atagaaaaat aaaaatctct tttccactcc   1440
attgtcgtat aggcatgtaa acagcctctt tttgatactg gaggaacact tgatggagtg   1500
tgagccacct aagatctcgg tttgccaaaa ttcatttcta attaaccttta ctaattatac   1560 tactttgtta ggattttcac attcttggct taatcatttt cattcctaaa gaaaatatc   1620 ttggcctaaa cctcagttat tacatgtaat ttgatgaggt atttggtatt tgttccntt   1679
```

<210> SEQ ID NO 36
<211> LENGTH: 233
<212> TYPE: PRT
<213> ORGANISM: Homo sapiens

<400> SEQUENCE: 36

```
Met Glu Pro Thr Ala Pro Ser Leu Thr Glu Glu Asp Leu Thr Glu Val
 1               5                  10                  15

Lys Lys Asp Ala Leu Glu Asn Leu Arg Val Tyr Leu Cys Glu Lys Ile
                20                  25                  30

Ile Ala Glu Arg His Phe Asp His Leu Arg Ala Lys Lys Ile Leu Ser
            35                  40                  45

Arg Glu Asp Thr Glu Glu Ile Ser Cys Arg Thr Ser Ser Arg Lys Arg
        50                  55                  60

Ala Gly Lys Leu Leu Asp Tyr Leu Gln Glu Asn Pro Lys Gly Leu Asp
 65                  70                  75                  80

Thr Leu Val Glu Ser Ile Arg Arg Glu Lys Thr Gln Asn Phe Leu Ile
                 85                  90                  95

Gln Lys Ile Thr Asp Glu Val Leu Lys Leu Arg Asn Ile Lys Leu Glu
            100                 105                 110

His Leu Lys Gly Leu Lys Cys Ser Ser Cys Glu Pro Phe Pro Asp Gly
        115                 120                 125

Ala Thr Asn Asn Leu Ser Arg Ser Asn Ser Asp Glu Ser Asn Phe Ser
    130                 135                 140

Glu Lys Leu Arg Ala Ser Thr Val Met Tyr His Pro Glu Gly Glu Ser
145                 150                 155                 160
```

```
Ser Thr Thr Pro Phe Phe Ser Thr Asn Ser Leu Asn Leu Pro Val
                165                 170                 175

Leu Glu Val Gly Arg Thr Glu Asn Thr Ile Phe Ser Ser Thr Thr Leu
            180                 185                 190

Pro Arg Pro Gly Asp Pro Gly Ala Pro Pro Leu Pro Pro Asp Leu Gln
        195                 200                 205

Leu Glu Glu Glu Gly Thr Cys Ala Asn Ser Ser Glu Met Phe Leu Pro
    210                 215                 220

Leu Arg Ser Arg Thr Val Ser Arg Gln
225                 230
```

<210> SEQ ID NO 37
<211> LENGTH: 1782
<212> TYPE: DNA
<213> ORGANISM: Mus musculus

<400> SEQUENCE: 37

| | | | | | |
|---|---|---|---|---|---|
| cacagcctga | ttcccggagg | cccgagccct | tagtctgggc | ggggtggcgc | gggccggaag | 60 |
| gacgccatcc | cggcctgggc | catggaggct | cccgcaccgt | ccctcacgga | ggaggatttg | 120 |
| actgaagtga | agaaggacgc | tttagagaat | ttacgtgttt | acctgtgtga | gaaaatcata | 180 |
| gctgagagac | attttgatca | tctacgtgca | aaaaaaatac | taagtagaga | agacacagaa | 240 |
| gaaatttctt | gccgaacttc | aagtagaaaa | cgggctggga | agttgttaga | ctacttacag | 300 |
| gagaacccca | ggggcctgga | caccctggtg | aatccatcc | gcagggagaa | aacacagagc | 360 |
| ttcctgattc | agaagataac | ggatgaggtg | ctaaagcttc | ggaatataaa | actggagcac | 420 |
| ctcaaaggcc | tgaagtgcag | cagctgtgag | ccctttgcag | ccggagccac | caacaacctc | 480 |
| tctaggtgca | attccgatga | gagcaatctc | tctgagaaac | agagagcatc | cactgtcatg | 540 |
| taccacccgg | agggagagtc | cagcacggct | cccttcttct | ctatggcgtc | gtccctgaac | 600 |
| ttgccagtcc | tggaagttgg | caggactgaa | aacagcagct | tctcttcagc | cactcttcct | 660 |
| cgacctgggg | accctgggc | tccccctttg | ccccagacc | ttcggttgga | agaggggga | 720 |
| agttgtggaa | actcaagtga | gatgtttctc | cccttacggt | cacgggctct | ttcacgccaa | 780 |
| tgatacatca | ccgcctagtt | gttttactag | tgatgcaaaa | tgctgtgaag | gaggccatct | 840 |
| ttctatacaa | accacggtga | caggtcactc | acattcgatg | cgtgccttta | aaatcagtgt | 900 |
| acacattctc | tgtaaatagg | atttgttagg | gtaaagaagc | gctctgggc | ggcgtggtgt | 960 |
| aaatcatggt | ggtcgtgact | tttccataat | gtcctttctt | ttttattatt | tttaggtgtt | 1020 |
| tgcgtatttt | gaacttttca | taagattaat | tttatcggaa | tatttctcaa | tttgagaaaa | 1080 |
| caacttgtgg | attgggaata | atgttttag | cacatttatg | ctacaaattt | tcagtctgat | 1140 |
| tgttttcccc | actgatctgg | cagtatattt | tagcagtaag | ctgttgtgtt | tcaggaaagc | 1200 |
| tggacacggg | aaagctgccg | acacactcag | cagtgtccca | ctccttagtt | ctgagaagcc | 1260 |
| gtcgggttct | gaggagacac | ctggtggcac | tgagcctggt | gacctcagtg | ggccaaaatt | 1320 |
| tgttttatac | tcaccctgcc | agcgtgagtg | tcttactttc | acaggccttg | tgtcctcagt | 1380 |
| cttatcttaa | aggatgttat | cttggcaggg | catcacttgt | aattaatgga | tgatacttgt | 1440 |
| aattgactaa | agtcctcgct | ctgagccgtt | tgttctggct | ccgagagcgc | tgacatgtga | 1500 |
| agcatggtga | gcagcgaggg | aactgacagg | atgtggccgt | ggccagtgtg | gctttagtgt | 1560 |
| ttgcatcagg | cagccaccag | ctccatccgt | gttcttactg | ctttacaaag | tttgactaac | 1620 |
| tttacacatt | ttaaaaatgc | tgattgtctt | cgtttaaatt | ataattttac | ctatttcttg | 1680 |

-continued

```
acatctaact cctattcatt tctattattt aaaaattaag aaatgaaaat ttgctattaa    1740
caataaagtt tttttaatgt aaaaaaaaaa aaaaaaaaaa aa                      1782
```

<210> SEQ ID NO 38
<211> LENGTH: 233
<212> TYPE: PRT
<213> ORGANISM: Mus musculus

<400> SEQUENCE: 38

```
Met Glu Ala Pro Ala Pro Ser Leu Thr Glu Glu Asp Leu Thr Glu Val
 1               5                  10                  15

Lys Lys Asp Ala Leu Glu Asn Leu Arg Val Tyr Leu Cys Glu Lys Ile
            20                  25                  30

Ile Ala Glu Arg His Phe Asp His Leu Arg Ala Lys Lys Ile Leu Ser
        35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Arg Gly Leu Asp
65                  70                  75                  80

Thr Leu Val Glu Ser Ile Arg Arg Glu Lys Thr Gln Ser Phe Leu Ile
                85                  90                  95

Gln Lys Ile Thr Asp Glu Val Leu Lys Leu Arg Asn Ile Lys Leu Glu
            100                 105                 110

His Leu Lys Gly Leu Lys Cys Ser Ser Cys Glu Pro Phe Ala Ala Gly
        115                 120                 125

Ala Thr Asn Asn Leu Ser Arg Cys Asn Ser Asp Glu Ser Asn Leu Ser
    130                 135                 140

Glu Lys Gln Arg Ala Ser Thr Val Met Tyr His Pro Glu Gly Glu Ser
145                 150                 155                 160

Ser Thr Ala Pro Phe Phe Ser Met Ala Ser Ser Leu Asn Leu Pro Val
                165                 170                 175

Leu Glu Val Gly Arg Thr Glu Asn Ser Ser Phe Ser Ser Ala Thr Leu
            180                 185                 190

Pro Arg Pro Gly Asp Pro Gly Ala Pro Pro Phe Pro Pro Asp Leu Arg
        195                 200                 205

Leu Glu Glu Gly Gly Ser Cys Gly Asn Ser Ser Glu Met Phe Leu Pro
    210                 215                 220

Leu Arg Ser Arg Ala Leu Ser Arg Gln
225                 230
```